US007582423B2

(12) United States Patent
Padgett et al.

(10) Patent No.: US 7,582,423 B2
(45) **Date of Patent: *Sep. 1, 2009**

(54) POPULATION OF POLYNUCLEOTIDE SEQUENCE VARIANTS

(75) Inventors: Hal S. Padgett, Vacaville, CA (US); John A. Lindbo, Vacaville, CA (US); Wayne P. Fitzmaurice, Vacaville, CA (US)

(73) Assignee: Novici Biotech LLC, Vacaville, CA (US)

( * ) Notice: Subject to any disclaimer, the term of this patent is extended or adjusted under 35 U.S.C. 154(b) by 326 days.

This patent is subject to a terminal disclaimer.

(21) Appl. No.: 10/280,913

(22) Filed: Oct. 25, 2002

(65) Prior Publication Data

US 2004/0110130 A1 Jun. 10, 2004

Related U.S. Application Data

(63) Continuation-in-part of application No. 10/066,390, filed on Feb. 1, 2002.

(60) Provisional application No. 60/402,342, filed on Aug. 8, 2002, provisional application No. 60/268,785, filed on Feb. 14, 2001, provisional application No. 60/266,386, filed on Feb. 2, 2001.

(51) Int. Cl.

| | |
|---|---|
| ***C12Q 1/68*** | (2006.01) |
| ***C12P 19/34*** | (2006.01) |
| *C07H 21/02* | (2006.01) |
| *C07H 21/04* | (2006.01) |

(52) U.S. Cl. .......................... 435/6; 435/91.2; 536/23.1

(58) Field of Classification Search ....................... None
See application file for complete search history.

(56) References Cited

U.S. PATENT DOCUMENTS

| | | | | |
|---|---|---|---|---|
| 4,994,368 | A | 2/1991 | Goodman et al. | |
| 5,459,039 | A | 10/1995 | Modrich et al. | |
| 5,556,747 | A | 9/1996 | Kumar | |
| 5,679,522 | A | 10/1997 | Modrich et al. | |
| 5,683,877 | A | 11/1997 | Lu-Chang et al. | |
| 5,723,323 | A | 3/1998 | Kauffman et al. | |
| 5,795,747 | A | 8/1998 | Henco et al. | |
| 5,861,482 | A | 1/1999 | Modrich et al. | |
| 5,869,245 | A | 2/1999 | Yeung et al. | |
| 5,922,539 | A | 7/1999 | Modrich et al. | |
| 6,057,103 | A | 5/2000 | Short | |
| 6,165,793 | A | 12/2000 | Stemmer | |
| 6,391,557 | B1 | 5/2002 | Yeung | |
| 6,537,746 | B2 | 3/2003 | Arnold et al. | |
| 6,783,941 | B2 | 8/2004 | Vind | |
| 6,821,758 | B1 | 11/2004 | Koltermann | |
| 6,846,655 | B1 | 1/2005 | Wagner et al. | |
| 2002/0045175 | A1 | 4/2002 | Wang et al. | |
| 2003/0017477 | A1 | 1/2003 | Vind | |
| 2004/0048268 | A1 | 3/2004 | Delcourt et al. | |
| 2004/0091886 | A1 * | 5/2004 | Moore et al. | 435/6 |

FOREIGN PATENT DOCUMENTS

| | | |
|---|---|---|
| DE | 4112440 | 10/1992 |
| DE | 19953854 | 6/2001 |
| FR | 2789696 | 8/2000 |
| WO | WO 92/18645 | 10/1992 |
| WO | WO 96/40902 | 12/1996 |
| WO | WO 97/37011 | 10/1997 |
| WO | WO 97/46701 | 12/1997 |
| WO | WO 99/28451 | 6/1999 |
| WO | WO 99/29902 | 6/1999 |
| WO | WO 00/71730 | 11/2000 |
| WO | WO 01/34835 | 5/2001 |
| WO | WO 01/62974 | 8/2001 |
| WO | WO 02/24953 A1 | 3/2002 |

OTHER PUBLICATIONS

Singer, M. et al. ("Genes and Genomes", University Science Books, p. 280, 1991).*

Kumagai, M.H. et al. "Rapid, high-level expression of biologically active alpha-trichosantin in transfected plants by an RNA viral vector", PNAS USA, pp. 427-430 (1993).*

Kunkel, T. A. et al., "Efficient Site-Directed Mutagenesis Using Uracil-Containing DNA", Methods in Enzymology, vol. 204, pp. 125-139 (1991).*

Jendrisiak, J. et al.,"In Vitro Insertion of Transposon Containing an *E.coli* Origin of Replication Facilitates Rapid Recovery, Propagation and Sequencing of Circular DNA Molecules from Heterologous Organisms", EPICENTRE Forum, vol. 9, pp. 14, 15 (2002).*

EasyXpress NMR Protein Synthesis Kit, downloaded Jul. 25, 2006 from www1.qiagen.com/Products/Protein/Expression/EasyXpress/EasyExpressNMRProteinSynthesisKits.aspx.*

Google search for the term "in vitro", Dec. 27, 2006.*

Cooper, D.L. et al., J. Biol. Chem., vol. 268, pp. 11823-11829 (1993).*

Parikh, S. S. et al., Structure, vol. 5, pp. 1543-1550 (1997).*

Biswas and Hsieh, "Identification and characterization of a thermostable MutS homolog from *Thermus aquaticus*", *J. Biol. Chem.* (1996) 271(9):5040-5048.

Kraemer and Digiovanna, "Topical enzyme therapy for skin diseases?", *J. Am. Acad. Dermatol.* (2002) 46:463-6.

O'Grady, et al., "DNA repair in thermophiles: investigation of DNA-binding activities in *Thermus aquaticus*", *Biochem. Soc. Tranactions* (1997) 25:319-22.

(Continued)

*Primary Examiner*—Teresa E Strzelecka
(74) *Attorney, Agent, or Firm*—Wayne P. Fitzmaurice

(57) ABSTRACT

We describe here an in vitro method of redistributing sequence variations between non-identical polynucleotide sequences, by making a heteroduplex polynucleotide from two non-identical polynucleotides; introducing a nick in one strand at or near a base pair mismatch site; removing mismatched base(s) from the mismatch site where the nick occurred; and using the opposite strand as template to replace the removed base(s) with bases that complement base(s) in the first strand. By this method, information is transferred from one strand to the other at sites of mismatch.

17 Claims, 18 Drawing Sheets

OTHER PUBLICATIONS

Sugahara, et al., "Crystal structure of a repair enzyme of oxidatively damaged DNA, MutM (Fpg), from an extreme thermophile, *Thermus thermophilus* HB8", *EMBO J* (2000) 19(15):3857-3869.
Wang, "Creating hybrid genes by homologous recombination", *Disease Markers* (2000) 16:3-13.
Birkenkamp and Kemper, "In vitro processing of heteroduplex loops and mismatches by Endonuclease VII", *DNA Research*, 1995, vol. 2, pp. 9-14.
Abastado, et al., "Processing of complex heteroduplexes in *Escherichia coli* and *Cos*-1 monkey cells", *Proc. Natl. Acad. Sci. USA*, Sep. 1984, vol. 81, pp. 5792-5796.
Cami, et al., "Correction of complex heteroduplexes made of mouse H-2 gene sequences in *Escherichia coli* K-12", *Proc. Natl. Acad. Sci. USA*, Jan. 1984, vol. 81, pp. 503-507.
Chang, et al., "Recombination following transformation of *Escherichia coli* by heteroduplex plasmid DNA molecules", *Gene*, 1984, vol. 29, pp. 255-261, Elsevier.
Cotton, "Slowly but surely towards better scanning for mutations", *TIG*, Feb. 1997, vol. 13, No. 2, pp. 43-46, Elsevier Science Ltd.
Joyce, "Directed Molecular Evolution", *Scientific American*, Dec. 1992, pp. 90-97.
Kulinski, et al., "CEL I Enzymatic Mutation Detection Assay", *Biotechniques*, Jul. 2000, vol. 29, pp. 44-48.
Lahue, et al., "Requirement for d(GATC) sequences in *Escherichia coli mutHLS* mismatch correction", *Proc. Natl. Acad. Sci. USA*, Mar. 1987, vol. 84, pp. 1482-1486.
Modrich, "Strand-specific Mismatch Repair in Mammalian Cells", *The Journal of Biological Chemistry*, Oct. 3, 1997, vol. 272, No. 4, pp. 24727-24730, The American Society of for Biochemistry and Molecular Biology, Inc., Bethesda, MD.
Oleykowski, et al., "Mutation detection using a novel plant endonuclease", *Nucleic Acids Research*, 1998, vol. 26, No. 20, pp. 4597-4602, Oxford University Press, United Kingdom.
Oleykowski, et al., "Incision at Nucleotide Insertions/Deletions and Base Pair Mismatches by the SP Nuclease of Spinach", *Biochemistry*, 1999, vol. 38, pp. 2200-2205, American Chemical Society, Columbus, OH.
Robertson, "Directed evolution patent could have major impact", *Nature Biotechnology*, May 1998, vol. 16, p. 411.
Solaro, et al., "Endonuclease VII of Phage T4 Triggers Mismatch Correction in Vitro", *J. Mol. Biol.*, 1993, vol. 230, pp. 868-877, Academic Press Limited.
Volkov, et al., "Random Chimeragenesis by Heteroduplex Recombination", *Methods in Enzymology*, 2000, vol. 328, pp. 456-463, Academic Press.
Volkov, et al., "Recombination and chimeragenesis by in vitro heteroduplex formation and in vivo repair", *Nucleic Acids Research*, 1999, vol. 27, No. 18, pp. e18 (i-vi), Oxford Univeristy Press.
Yang, et al., "Purification, Cloning, and Characterization of the CEL I Nuclease", *Biochemistry*, 2000, vol. 39, pp. 3533-3541, American Chemical Society.
Fishel, R. and R. Kolodner, Gene conversion in *Escherichia coli*: the recF pathway for resolution of heteroduplex DNA. J Bacteriol, 1989. 171(6): p. 3046-52.
Fishel, R.A. and R. Kolodner, An *Escherichia coli* cell-free system that catalyzes the repair of symmetrically methylated heteroduplex DNA. Cold Spring Harb Symp Quant Biol, 1984. 49: p. 603-9.
Glaser, P.M., et al., DNA mismatch repair detected in human cell extracts. Mol Cell Biol, 1987. 7(1): p. 218-24.
Paabo, S., D.M. Irwin, and A.C. Wilson, DNA damage promotes jumping between templates during enzymatic amplification. J Biol Chem, 1990. 265(8): p. 4718-21.
Su, S.S., et al., Mispair specificity of methyl-directed DNA mismatch correction in vitro. J Biol Chem, 1988. 263(14): p. 6829-35.
Sung, W.L., et al., Simultaneous synthesis of human-, mouse- and chimeric epidermal growth factor genes via 'hybrid gene synthesis' approach. Nucleic Acids Res, 1986. 14(15): p. 6159-68.
Weber, H. and C. Weissmann, Formation of genes coding for hybrid proteins by recombination between related, cloned genes in *E. coli.* Nucleic Acids Res, 1983. 11(16): p. 5661-9.
Google search for the term "in vivo", Apr. 19, 2007.
Borts, R.H. and Haber, J.E., "Meiotic Recombination in Yeast: Alteration by Multiple Heterozygosities", Science 237 (1987) 1459-1465.
Wagner et al., "Involvement of *Escherichia coli* Mismatch Repair in DNA Replication and Recombination", Cold Spring Harb Symp Quant Biol 49 (1984) 611-615.
Doutriaux et al., "Mismatch-stimulated Killing", Proc Natl Acad Sci USA 83 (1986) 2576-2578.

* cited by examiner

FIG. 2A

| | | |
|---|---|---|
| X | 5'-A G A T C A A T T G-3' | 1+ |
| | 3'-T C T A G T T A A C-5' | 2- |
| Y | 5'-A G A C C G A T T G-3' | 3+ |
| | 3'-T C T G G C T A A C-5' | 4- |

FIG. 2B

| Possible Strand Combinations | Possible +/- Strand Combinations | Partially Complementary Populations |
|---|---|---|
| 1+/2- | ✓ | |
| 1+/3+ | | |
| 1+/4- | ✓ | ✓ |
| 2-/3+ | ✓ | ✓ |
| 2-/4- | | |
| 3+/4- | ✓ | |

FIG. 3 atggcaacga ccaagacgag cgggatggcg ctggctttgc tcctcgtcgc cgccctggcc
gtgggagctg cggcctgggg gaaagagggc catcgcctca cttgtatggt cgccgagccc
tttctaagct ctgaatccaa gcaagctgtg gaggagcttc tctctggaag agatctcccg
gacttgtgtt catgggccga tcagattcga agatcgtata agtttagatg gactggtcct
ttgcactaca tcgatactcc agacaacctc tgcacctatg actatgatcg tgactgccac
gattcccatg ggaagaagga cgtgtgtgtc gctggtggga tcaacaatta ctcgtcgcag
ctggaaacgt ttctagattc agagagctcg tcgtataact tgaccgaggc gctgctcttc
ctggctcact ttgtcgggga tatacaccag cccttgcacg tagcatttac gagtgatgcc
ggaggcaatg gcgtgcacgt ccgctggttt ggacgaaagg ccaacttgca tcacgtctgg
gatacagaat ttatttctag agccaatcgt gtgtactacc acgacatttc caagatgctc
cggaacatta ccaggagcat aactaagaag aatttcaata gttggagcag atgtaagact
gatccggcgg cttgtattga tagttatgcg acagaaagta tagatgcttc ttgcaactgg
gcatacaaag acgcacccga cggaagctct ctagatgatg attacttctc ttcacgcctt
ccaattgttg agcagcgtct tgctcaaggg ggcgtcaggc tggcgtcaat actcaacagg
atttttggag gagcaaagtc gaacaggtcc agtcgctcaa gcatgtag

FIG. 4

Met Ala Thr Thr Lys Thr Ser Gly Met Ala Leu Ala Leu Leu Leu Val

Ala Ala Leu Ala Val Gly Ala Ala Ala Trp Gly Lys Glu Gly His Arg

Leu Thr Cys Met Val Ala Glu Pro Phe Leu Ser Ser Glu Ser Lys Gln

Ala Val Glu Glu Leu Leu Ser Gly Arg Asp Leu Pro Asp Leu Cys Ser

Trp Ala Asp Gln Ile Arg Arg Ser Tyr Lys Phe Arg Trp Thr Gly Pro

Leu His Tyr Ile Asp Thr Pro Asp Asn Leu Cys Thr Tyr Asp Tyr Asp

Arg Asp Cys His Asp Ser His Gly Lys Lys Asp Val Cys Val Ala Gly

Gly Ile Asn Asn Tyr Ser Ser Gln Leu Glu Thr Phe Leu Asp Ser Glu

Ser Ser Ser Tyr Asn Leu Thr Glu Ala Leu Leu Phe Leu Ala His Phe

Val Gly Asp Ile His Gln Pro Leu His Val Ala Phe Thr Ser Asp Ala

Gly Gly Asn Gly Val His Val Arg Trp Phe Gly Arg Lys Ala Asn Leu

His His Val Trp Asp Thr Glu Phe Ile Ser Arg Ala Asn Arg Val Tyr

Tyr His Asp Ile Ser Lys Met Leu Arg Asn Ile Thr Arg Ser Ile Thr

Lys Lys Asn Phe Asn Ser Trp Ser Arg Cys Lys Thr Asp Pro Ala Ala

Cys Ile Asp Ser Tyr Ala Thr Glu Ser Ile Asp Ala Ser Cys Asn Trp

Ala Tyr Lys Asp Ala Pro Asp Gly Ser Ser Leu Asp Asp Asp Tyr Phe

Ser Ser Arg Leu Pro Ile Val Glu Gln Arg Leu Ala Gln Gly Gly Val

Arg Leu Ala Ser Ile Leu Asn Arg Ile Phe Gly Gly Ala Lys Ser Asn

Arg Ser Ser Arg Ser Ser Met

FIG. 5 gtggcacttt tcggggaaat gtgcgcggaa cccctatttg tttatttttc taaatacatt caaatatgta
tccgctcatg agacaataac cctgataaat gcttcaataa tattgaaaaa ggaagagtat gagtattcaa
catttccgtg tcgcccttat tccctttttt gcggcatttt gccttcctgt ttttgctcac ccagaaacgc
tggtgaaagt aaaagatgct gaagatcagt tgggtgcacg agtgggttac atcgaactgg atctcaacag
cggtaagatc cttgagagtt ttcgccccga agaacgtttt ccaatgatga gcacttttaa agttctgcta
tgtggcgcgg tattatcccg tattgacgcc gggcaagagc aactcggtcg ccgcatacac tattctcaga
atgacttggt tgagtactca ccagtcacag aaaagcatct tacggatggc atgacagtaa gagaattatg
cagtgctgcc ataaccatga gtgataacac tgcggccaac ttacttctga caacgatcgg aggaccgaag
gagctaaccg cttttttgca caacatgggg gatcatgtaa ctcgccttga tcgttgggaa ccggagctga
atgaagccat accaaacgac gagcgtgaca ccacgatgcc tgtagcaatg gcaacaacgt tgcgcaaact
attaactggc gaactactta ctctagcttc ccggcaacaa ttaatagact ggatggaggc ggataaagtt
gcaggaccac ttctgcgctc ggcccttccg gctggctggt ttattgctga taaatctgga gccggtgagc
gtgggtctcg cggtatcatt gcagcactgg ggccagatgg taagccctcc cgtatcgtag ttatctacac
gacggggagt caggcaacta tggatgaacg aaatagacag atcgctgaga taggtgcctc actgattaag
cattggtaac tgtcagacca agtttactca tatatacttt agattgattt aaaacttcat ttttaattta
aaaggatcta ggtgaagatc ctttttgata atctcatgac caaaatccct taacgtgagt tttcgttcca
ctgagcgtca gaccccgtag aaaagatcaa aggatcttct tgagatcctt tttttctgcg cgtaatctgc
tgcttgcaaa caaaaaaacc accgctacca gcggtggttt gtttgccgga tcaagagcta ccaactcttt
ttccgaaggt aactggcttc agcagagcgc agataccaaa tactgtcctt ctagtgtagc cgtagttagg
ccaccacttc aagaactctg tagcaccgcc tacatacctc gctctgctaa tcctgttacc agtggctgct
gccagtggcg ataagtcgtg tcttaccggg ttggactcaa gacgatagtt accggataag gcgcagcggt
cgggctgaac ggggggttcg tgcacacagc ccagcttgga gcgaacgacc tacaccgaac tgagatacct
acagcgtgag ctatgagaaa gcgccacgct tcccgaaggg agaaaggcgg acaggtatcc ggtaagcggc
agggtcggaa caggagagcg cacgagggag cttccagggg gaaacgcctg gtatctttat agtcctgtcg
ggtttcgcca cctctgactt gagcgtcgat ttttgtgatg ctcgtcaggg gggcggagcc tatggaaaaa
cgccagcaac gcggcctttt tacggttcct ggccttttgc tggccttttg ctcacatgtt ctttcctgcg
ttatcccctg attctgtgga taaccgtatt accgcctttg agtgagctga taccgctcgc cgcagccgaa
cgaccgagcg cagcgagtca gtgagcgagg aagcggaaga gcgcccaata cgcaaaccgc ctctccccgc
gcgttggccg attcattaat gcagctggca cgacaggttt cccgactgga aagcgggcag tgagcgcaac
gcaattaatg tgagttagct cactcattag gcaccccagg ctttacactt tatgcttccg gctcgtatgt
tgtgtggaat tgtgagcgga taacaatttc acacaggaaa cagctatgac catgattacg ccaagcgcgc
aattaaccct cactaaaggg aacaaaagct gggtaccgat gagtaaagga gaagaacttt tcactggagt
tgtcccaatt cttgttgaat tagatggtga tgttaatggg cacaaatttt ctgtcagtgg agagggtgaa
ggtgatgcta catacggaaa gcttaccctt aaatttattt gcactactgg aaaactacct gttccatggc
caacacttgt cactactttc tcttatggtg ttcaatgctt ttcccgttat ccggatcata tgaaacggca
tgactttttc aagagtgcca tgcccgaagg ttatgtacag gaacgcacta tatctttcaa agatgacggg
aactacaaga cgcgtgctga agtcaagttt gaaggtgata cccttgttaa tcgtatcgag ttaaaaggta
ttgattttaa agaagatgga aacattctcg gacacaaact cgagtacaac tataactcac acaatgtata
catcacggca gacaaacaaa agaatggaat caaagctaac ttcaaaattc gccacaacat tgaagatgga
tccgttcaac tagcagacca ttatcaacaa aatactccaa ttggcgatgg ccctgtcctt ttaccagaca
accattacct gtcgacacaa tctgcccttt cgaaagatcc caacgaaaag cgtgaccaca tggtccttct
tgagtttgta actgctgctg ggattacaca tggcatggat gaactataca aataagaatt cctgcagccc
gggggatcca ctagttctag agcggccgcc accgcggtgg agctccaatt cgccctatag tgagtcgtat
tacgcgcgct cactggccgt cgttttacaa cgtcgtgact gggaaaaccc tggcgttacc caacttaatc
gccttgcagc acatccccct ttcgccagct ggcgtaatag cgaagaggcc cgcaccgatc gcccttccca
acagttgcgc agcctgaatg gcgaatggga cgcgccctgt agcggcgcat taagcgcggc gggtgtggtg
gttacgcgca gcgtgaccgc tacacttgcc agcgccctag cgcccgctcc tttcgctttc ttcccttcct
ttctcgccac gttcgccggc tttccccgtc aagctctaaa tcgggggctc cctttagggt tccgatttag
tgctttacgg cacctcgacc ccaaaaaact tgattagggt gatggttcac gtagtgggcc atcgccctga
tagacggttt ttcgcccttt gacgttggag tccacgttct ttaatagtgg actcttgttc caaactggaa
caacactcaa ccctatctcg gtctattctt ttgatttata agggattttg ccgatttcgg cctattggtt
aaaaaatgag ctgatttaac aaaaatttaa cgcgaatttt aacaaaatat taacgcttac aatttag

FIG. 6 atgtcttacg agcctaaagt gagcgacttc cttgctctta cgaaaaagga ggaaatttta
cccaaggctc ttacgaggtt aaagactgtc tctattagta ctaaggatgt tatatctgtt
aaggattctg agtccctgtg tgatatagat ttactagtta atgtgccatt agataagtat
agatatgtgg gtgttttagg tgttgttttt accggtgagt ggttagtgcc ggatttcgtt
aaaggtggag taacagtgag cgtgattgac aaacggcttg agaactccaa agagtgcata
attggtacgt acagagctgc tgcgaaagac aaaaggttcc agttcaagct ggttccaaat
tacttcgtgt ctgttgcaga tgccaagcga aaaccgtggc aagttcatgt gcgtattcaa
aatttaagga ttgaagctgg atggcaacct ctggccttag aggtggtttc tgttgctatg
gtcactaata acgtggttgt taagggtttg agagaaaagg tcatcgcagt gaatgatccg
aatgtcgaag gtttcgaagg cgtggttgac gatttcgtcg attcggtcgc agcattcaag
gcggttgaca ctttcagaaa gaaaaagaaa aggattggag gaaaggatgt aaataataat
aagtttagat atagaccgga gagatacgcc ggtcaggatt cgttaaatta taaagaagaa
aacgtcttac aacatcacga actcgaatca gtaccagtat ttcgcagcga cgtgggcaga
gcccacagcg atgctt

FIG. 7

```
atgtcaaagg ctattgtcaa gatcgatgaa ttcattaaat tatccaagtc tgaagaggtt
ttaccttctg cattcacaag aatgaagtcg gtcagagtct caacagtgga taagataatg
gccaaagaga atgacaatat ttccgaagta gatttactta agggtgttaa gttagttaaa
aatggttatg tttgtttagt aggtcttgtg gtgtcaggag agtggaattt acccgacaac
tgcagaggtg gtgtaagtat ctgtctgata gacaaacgta tgcaacgtca taacgaagct
actttaggtt cgtacactac caaagccagc aagaaaaact tttcgttcaa gcttataccg
aattactcga taacctctca agatgctgaa aggcgtcctt gggaagttat ggtaaatatt
cgtggtgtgg ctatgtccga aggttggtgt ccattatcct tagagttcgt ttctgtttgt
attgttcata aaaacaatgt tagaaagggt ctaagagaga aggtgactgc cgtgtccgaa
gacgacgcta tagaactcac agaagaggtt gttgatgagt ttatagaagc cgtaccgatg
gcgcgacgtt tgcagaactt gagaaaaccc aagtacaaca aagaaaaaga aaataaaaat
ttgaataata aaaatagtat aggagtttcc aaacctgtcg gtttggaaag aaataaagta
aggagtgtag ttagaaaagg ggttaggagt gatagtagtt taggtgtgac tgatatgagt
caggacggta gctcaagcga gatatcatcc gattcgttta ttt
```

FIG. 8 atggctgtta gtctcagaga tactgtcaaa attagcgagt tcattgatct ttcgaaacag
gatgagatac ttccggcatt catgactaag gtcaagagcg tcagaatatc gactgtggac
aagattatgg ctgttaagaa tgatagtctt tctgatgtag atttacttaa aggtgttaag
ttagttaaga atgggtacgt gtgcttagct ggtttggtag tgtctgggga gtggaatctc
ccggacaact gccgtggtgg tgtcagtgtt tgtattgtag ataagagaat gaaaaggagt
aaggaggcaa cgctgggtgc gtatcacgcc cctgcttgca aaaagaattt ttcctttaag
ctaatcccta attattcaat aacatccgag gatgctgaga agcacccatg gcaagtatta
gtgaatatca aaggagtggc tatggaagaa ggatactgtc ctttatcttt ggagttcgtt
tcaatttgtg tagtacataa aaataatgta agaaaaggtt tgagggaacg tattttgaga
gtaacagacg gctcgccaat tgaactcact gaaaaagttg ttgaggagtt catagatgaa
gtaccaatgg ctgtgaaact cgaaaggttc cggaaaacaa aaaagagagt ggtaggtaat
agtgttaata ataagaaaat aaataatagt ggtaagaaag gtttgaaagt tgaggaaatt
gaggataatg taagtgatga cgagtctatc gcgtcatcga gtacgtttt

FIG. 9 atggctctag ttgttaaagg taaggtaaat attaatgagt ttatcgatct gtcaaagtct
gagaaacttc tcccgtcgat gttcacgcct gtaaagagtg ttatggtttc aaaggttgat
aagattatgg tccatgaaaa tgaatcattg tctgaagtaa atctcttaaa aggtgtaaaa
cttatagaag gtgggtatgt ttgcttagtt ggtcttgttg tgtccggtga gtggaattta
ccagataatt gccgtggtgg tgtgagtgtc tgcatggttg acaagagaat ggaaagagcg
gacgaagcca cactggggtc atattacact gctgctgcta aaaagcggtt tcagtttaaa
gtggtcccaa attacggtat tactacaaag gatgcagaaa agaacatatg gcaagttcat
gtgcgtattc aaaatttaag gattgaagct ggatggcaac ctctggcctt agaggtggtt
tctgttgcta tggtcactaa taacgtggtt gttaagggtt tgagagaaaa ggtcatcgca
gtgaatgatc cgaatgtcga aggtttcgaa ggcgtggttg acgatttcgt cgattcggtc
gcagcattca aggcggttga cactttcaga aagaaaaaga aaaggattgg aggaaaggat
gtaaataata ataagtttag atatagaccg gagagatacg ccggtcagga ttcgttaaat
tataaagaag aaaacgtctt acaacatcac gaactcgaat cagtaccagt atttcgcagc
gacgtgggca gagcccacag cgatgctt

FIG. 10

```
atgtcttacg agcctaaagt gagcgacttc cttgctctta cgaaaaagga ggaaatttta
cccaaggctc ttacgaggtt aaagactgtc tctattagta ctaaggatgt tatatctgtt
aaggattctg agtccctgtg tgatatagat ttactagtta atgtgccatt agataagtat
agatatgtgg gtgttttagg tgttgttttt accggtgagt ggaatttacc agataattgc
cgtggtggtg tgagtgtctg catggttgac aagagaatgg aaagagcgga cgaagccaca
ctggggtcat attacactgc tgctgcgaaa gacaaaaggt tccagttcaa gctggttcca
aattacttcg tgtctgttgc agatgccaag cgaaaaccgt ggcaagttca tgtgcgtatt
caaaatttaa ggattgaagc tggatggcaa cctctggcct tagaggtggt ttctgttgct
atggtcacta ataacgtggt tgttaagggt ttgagagaaa aggtcatcgc agtgaatgat
ccgaatgtcg aaggtttcga aggcgtggtt gacgatttcg tcgattcggt cgcagcattc
aaggcggttg acactttcag aaagaaaaag aaaaggattg gaggaaagga tgtaaataat
aataagttta gatatagacc ggagagatac gccggtcagg attcgttaaa ttataaagaa
gaaaacgtct tacaacatca cgaactcgaa tcagtaccag tatttcgcag cgacgtgggc
agagcccaca gcgatgctt
```

FIG. 11 aaataaacga atcggatgat atctcgcttg agctaccgtc ctgactcata tcagtcacac
ctaaactact atcactccta acccctttc taactacact ccttacttta tttctttcca
aaccgacagg tttggaaact cctatactat ttttattatt caaattttta ttttcttttt
ctttgttgta cttgggtttt ctcaagttct gcaaacgtcg cgccatcggt acggcttcta
taaactcatc aacaacctct tctgtgagtt ctatagcgtc gtcttcggac acggcagtca
ccttctctct tagacccttt ctaacattgt ttttatgaac aatacaaaca gaaacgaact
ctaaggataa tggacaccaa ccttcggaca tagccacacc acgaatattt accataactt
cccaaggacg cctttcagca tcttgagagg ttatcgagta attcggtata agcttgaacg
aaaagttttt cttgctggct ttggtagtgt acgaacctaa agtagcttcg ttatgacgtt
gcatacgttt gtctatcaga cagatactta caccacctct gcagttgtcg ggtaaattcc
actctcctga caccacaaga cctactaaac aaacataacc accttctata agttttacac
cttttaagag atttacttca gacaatgatt cattctcttt ggccattatc ttatccactg
ttgagactct gaccgacttc attcttgtga atgcagaagg taaaacctct tcagacttgg
ataatttaat gaattcatcg atcttgacaa tagcctttga cat

FIG. 12

```
aatacgaatc agaatccgcg accgacgtct cggcttcatc ttcaatcaaa ttatcaaact
cttttt caac ttcatcaaaa cttttt ggtt taggccttcc gcctgaacgc cccttaccta
aattattatt attttt cgga cctctttttg aggatttggt tcgaaacttt gcgagtctaa
ccgacattgg aacattctcc atgaactcat caacaacctc ttctgtgagt tctatagcgt
cgtcttcgga cacggcagtc accttctctc ttagaccctt tctaacattg tttttatgaa
caatacaaac agaaacgaac tctaatgaca aagggcagta gcccgcactc attttt acat
ttttaatatt tactaagacc tgccatatgt tcttttctgc atcctttgta gtaataccgt
aatttgggac cactttaaac tgaaaccgct ttttagcagc agcagtgtaa tatgacccca
gtgtggcttc gtccgctctt tccattctct tgtcaaccat gcagacactc acaccaccac
ggcaattatc tggtaaattc cactctcctg acaccacaag acctactaaa caaacataac
cattttt aac taacttaaca cccttaagag atttacttcg gacaatgatt cattttcatg
gaccataatc ttatcaacct ttgaaaccat aacactcttt acaggcgtga atgcagaagg
taaaacctct tcagactttg acagatcgat aaactcatta atatttacct tacctttaac
aactagagcc at
```

FIG. 13

```
aatacgaatc agaatccgcg atagactcgt catcacttac attatcctca atttcctcaa
ctttcaaacc tttcttacca ctattattta ttttcttatt attaacacta ttacctacca
ctctcttttt tgttttccgg aacctttcga gtttcacagc cattggtact tcatctatga
actcatcaac aacttcttct gaaagttcca tgggtcctcc atcgttcaca ctcgttactt
tctccctcaa acccaatttt atattatttt tataaacaat acacacagac acaaattcta
aagataaagg gcagtatcct tcttccatag ccactccttt gatattcact aatacttgcc
atgggtgctt ttctgcatcc tcggatgtta ttgaataatt agggaccact ttaaactgaa
accgcttttt agcagcaggg gcgtgatacg cacccagcgt tgcctcctta ctcctttcca
ttctcttgtc aaccatgcag acactcacac caccacggca gttgtccggg agattccact
caccggacac aacaagacca actaagcaaa catacccacc ttctataagt tttacacctt
ttaagagatt tacttcagac aatgattcat tttcatggac cataatctta tcaacctttg
aaaccataac actctttaca ggcgtgaaca tcgacgggag aagtttctca gactttgaca
gatcgataaa ctcattaata tttaccttac ctttaacaac tagagccat
```

FIG. 14

```
aatacgaatc agaatccgcg accgacgtct cggcttcact tacattatcc tcaatttcct
caactttcaa aactttctta ccactattat ttattttctt attattaaca ctattaccta
ccactctctt ttttgttttc cggaaccttt cgagtttcac agccattggt acttcatcta
tgaactcatc aacaactttt tcagtgagtt caattggcga gccgtctgtt actctcaaaa
tacgttccct caaacccaat tttatattat ttttataaac aatacacaca gacacaaatt
ctaatgacaa agggcagtag cccgcactca tttttacatt tttaatattt actaagacct
gccatgggtg cttctcagca tcctcggatg ttattgaata attagggatt agcttaaagg
aaaaattctt tttgcaagca ggggcgtgat acgcacccag tgtggcttcg tccgctcttt
ccattctctt gtcaaccatg cagacactca caccaccacg gcagttgtcc gggagattcc
actcaccgga cacaacaaga ccaactaagc acacgtaccc attcttaact aacttaacac
ctttaagtaa atctacatca gacaatgatt cattttcatg gaccataatc ttatcaacct
ttgaaaccat aacactcttt acaggcgtga acatcgacgg gagaagtttc tcagactttg
acagatcgat aaactcgcta attttgacag tatctctgag actaacagcc at
```

FIG. 15 atggctctag ttgttaaagg aaaagtgaat attaatgagt ttatcgatct gtcaaagtct
gagaaacttc tcccgtcgat gttcacgcct gtaaagagtg ttatggtttc aaaggttgat
aagattatgg tccatgaaaa tgaatcattg tctgaagtaa atctcttaaa aggtgtaaaa
cttatagaag gtgggtatgt ttgcttagtt ggtcttgttg tgtccggtga gtggaattta
ccagataatt gccgtggtgg tgtgagtgtc tgcatggttg acaagagaat ggaaagagcg
gacgaagcca ctctcggatc ttactacaca gcagctgcaa agaaaagatt tcagttcaag
gtcgttccca attatgctat aaccacccag gacgcgatga aaaacgtctg gcaagtttta
gttaatatta gaaatgtgaa gatgtcagcg ggtttctgtc cgctttctct ggagtttgtg
tctgtgtgta ttgtttataa aaataatata aaattgggtt tgagggagaa agtaacgagt
gtgaacgatg gaggacccat ggaactttca gaagaagttg ttgatgagtt catggaagat
gtcccaatgt cggttagact cgcaaagttt cgatctcgaa ccggaaaaaa gagtgatgtc
cgcaaaggga aaaatagtag tagtgatcgg tcagtgccga acaagaacta tagaaatgtt
aaggattttg gaggaatgag ttttaaaaag aataatttaa tcgatgatga ttcggagacg
tcggtcgcgg attctgattc gtatt

FIG. 16

```
atggctctag ttgttaaagg aaaagtgaat atcaatgagt ttatcgacct gacaaagtct
gagaaacttc tcccgtcgat gtttacccct gtaaagagtg ttatggttcc aaagttgata
agattatggt tcatgagaat gagtcattgt caggggtgaa ccttcttaaa ggagttaagc
ttattgatag tggatacgtc tgtttagccg gtttggtcgt cacgggcgag tggaacttgc
ctgacaattg ccgtggtggt gtgagcgtgt gtctggtgga caagagaatg gaaagagcgg
acgaagccac actggggtca tattacactg ctgctgctaa aaagcggttt cagttcaagg
tcgttcccaa ttatgctata accacccagg atgcagaaaa gaacatatgg caggtcttag
taaatattaa aaatgtgaag atgagtgcgg gctactgccc tttgtcatta gaatttgtgt
cggtgtgtat tgtttataga aataatataa aattgggttt gagagagaaa gtaacgagtg
tgaacgatgg agggcccatg gaacttacag aagaagtcgt tgatgagttc atggaagatg
tccctatgtc gatcaggctt gcaaagtttc gatctcgaat cctcaaaaag agtgatgtcc
gcaaagggaa aaatagtagt agtgatcggt cagtgccgaa caagaactat agaaatgtta
aggattttgg aggaatgagt tttaaaaaga ataatttaat cgatgatgat tcggaggcta
ctgtcgcgga ttctgattcg tttt
```

FIG. 17 atggctctag ttgttaaagg aaaagtgaat atcaatgagt ttatcgacct gacaaaaatg
gagaagatct taccgtcgat gtttacccct gtaaagagtg ttatgtgttc caaagttgat
aaaataatgg ttcatgagaa tgagtcattg tcaggggtga accttcttaa aggagttaag
cttattgata gtggatacgt ctgtttagcc ggtttggtcg tcacgggcga gtggaacttg
cctgacaatt gcagaggagg tgtgagcgtg tgtctggtgg acaaaaggat ggaaagagcc
gacgaggcca ctctcggatc ttactacaca gcagctgcaa agaaaagatt tcagttcaag
gtcgttccca attatgctat aaccacccag gacgcgatga aaaacgtctg gcaagtttta
gttaatatta gaaatgtgaa gatgtcagcg ggtttctgtc cgctttctct ggagtttgtg
tcggtgtgta ttgtttatag aaataatata aaattaggtt tgagagagaa gattacaaac
gtgagagacg gagggcccat ggaacttaca gaagaagtcg ttgatgagtt catggaagat
gtccctatgt cgatcaggct tgcaaagttt cgatctcgaa ccggaaaaaa gagtgatgtc
cgcaaaggga aaaatagtag tagtgatcgg tcagtgccga acaagaacta tagaaatgtt
aaggattttg gaggaatgag ttttaaaaag aataatttaa tcgatgatga ttcggaggct
actgtcgccg aatcggattc gttttaa

FIG. 18 atggctctag ttgttaaagg taaggtaaat attaatgagt ttatcgatct gtcaaagtct
gagaaacttc tcccgtcgat gttcacgcct gtaaagagtg ttatggtttc aaaggttgat
aagattatgg tccatgaaaa tgaatcattg tctgaagtaa atctcttaaa aggtgtaaaa
cttatagaag gtgggtatgt ttgcttagtt ggtcttgttg tgtccggtga gtggaattta
ccagataatt gccgtggtgg tgtgagtgtc tgcatggttg acaagagaat ggaaagagcg
gacgaagcca cactggggtc atattacact gctgctgcta aaaagcggtt tcagtttaaa
gtggtcccaa attacggtat tactacaaag gatgcagaaa agaacatatg gcaggtctta
gtaaatatta aaaatgtaaa aatgagtgcg ggctactgcc ctttgtcatt agaatttgtg
tctgtgtgta ttgtttataa aaataatata aaattgggtt tgagggagaa agtaacgagt
gtgaacgatg gaggacccat ggaactttca gaagaagttg ttgatgagtt catggagaat
gttccaatgt cggttagact cgcaaagttt cgaaccaaat cctcaaaaag aggtccgaaa
aataataata atttaggtaa ggggcgttca ggcggaaggc ctaaaccaaa aagttttgat
gaagttgaaa aagagtttga taatttgatt gaagatgaag ccgagacgtc ggtcgcggat
tctgattcgt att

POPULATION OF POLYNUCLEOTIDE SEQUENCE VARIANTS

This application is a continuation-in-part of U.S. Provisional Application No. 60/402,342, filed Aug. 8, 2002; and U.S. application Ser. No. 10/066,390, filed Feb. 1, 2002, which claims priority to U.S. Provisional Application No. 60/268,785, filed Feb. 14, 2001 and U.S. Provisional Application No. 60/266,386, filed Feb. 2, 2001, and which are incorporated herein by reference.

FIELD OF THE INVENTION

The invention relates generally to molecular biology and more specifically to methods of generating populations of related nucleic acid molecules.

BACKGROUND INFORMATION

DNA shuffling is a powerful tool for obtaining recombinants between two or more DNA sequences to evolve them in an accelerated manner. The parental, or input, DNAs for the process of DNA shuffling are typically mutants or variants of a given gene that have some improved character over the wild-type. The products of DNA shuffling represent a pool of essentially random reassortments of gene sequences from the parental nucleic acids that can then be analyzed for additive or synergistic effects resulting from new sequence combinations.

Recursive sequence reassortment is analogous to an evolutionary process where only variants with suitable properties are allowed to contribute their genetic material to the production of the next generation. Optimized variants are generated through DNA shuffling-mediated sequence reassortment followed by testing for incremental improvements in performance. Additional cycles of reassortment and testing lead to the generation of genes that contain new combinations of the genetic improvements identified in previous rounds of the process. Reassorting and combining beneficial genetic changes allows an optimized sequence to arise without having to individually generate and screen all possible sequence combinations.

This differs sharply from random mutagenesis, where subsequent improvements to an already improved sequence result largely from serendipity. For example, in order to obtain a protein that has a desired set of enhanced properties, it may be necessary to identify a mutant that contains a combination of various beneficial mutations. If no process is available for combining these beneficial genetic changes, further random mutagenesis will be required. However, random mutagenesis requires repeated cycles of generating and screening large numbers of mutants, resulting in a process that is tedious and highly labor intensive. Moreover, the rate at which sequences incur mutations with undesirable effects increases with the information content of a sequence. Hence, as the information content, library size, and mutagenesis rate increase, the ratio of deleterious mutations to beneficial mutations will increase, increasingly masking the selection of further improvements. Lastly, some computer simulations have suggested that point mutagenesis alone may often be too gradual to allow the large-scale block changes that are required for continued and dramatic sequence evolution.

Error-prone PCR uses low-fidelity polymerization conditions to introduce a low level of point mutations randomly over a sequence. A limitation to this method, however, is that published error-prone PCR protocols suffer from a low processivity of the polymerase, making this approach inefficient at producing random mutagenesis in an average-sized gene.

In oligonucleotide-directed random mutagenesis, a short sequence is replaced with a synthetically mutagenized oligonucleotide. To generate combinations of distant mutations, different sites must be addressed simultaneously by different oligonucleotides. The limited library size that is obtained in this manner, relative to the library size required to saturate all sites, requires that many rounds of selection are required for optimization. Mutagenesis with synthetic oligonucleotides requires sequencing of individual clones after each selection round followed by grouping them into families, arbitrarily choosing a single family, and reducing it to a consensus motif. Such a motif is resynthesized and reinserted into a single gene followed by additional selection. This step creates a statistical bottleneck, is labor intensive, and is not practical for many rounds of mutagenesis.

For these reasons, error-prone PCR and oligonucleotide-directed mutagenesis can be used for mutagenesis protocols that require relatively few cycles of sequence alteration, such as for sequence fine-tuning, but are limited in their usefulness for procedures requiring numerous mutagenesis and selection cycles, especially on large gene sequences.

As discussed above, prior methods for producing improved gene products from randomly mutated genes are of limited utility. One recognized method for producing a randomly reasserted gene sequences uses enzymes to cleave a long nucleotide chain into shorter pieces. The cleaving agents are then separated from the genetic material, and the material is amplified in such a manner that the genetic material is allowed to reassemble as chains of polynucleotides, where their reassembly is either random or according to a specific order. The method requires several rounds of amplification to assemble variants of genes that were broken into random fragments. ((Stemmer, 1994a; Stemmer, 1994b), U.S. Pat. No. 5,605,793, U.S. Pat. No. 5,811,238, U.S. Pat. No. 5,830,721, U.S. Pat. No. 5,928,905, U.S. Pat. No. 6,096,548, U.S. Pat. No. 6,117,679, U.S. Pat. No. 6,165,793, U.S. Pat. No. 6,153,410). A variation of this method uses primers and limited polymerase extensions to generate the fragments prior to reassembly (U.S. Pat. No. 5,965,408, U.S. Pat. No. 6,159,687).

However, both methods have limitations. These methods suffer from being technically complex. This limits the applicability of these methods to facilities that have sufficiently experienced staffs. In addition there are complications that arise from the reassembly of molecules from fragments, including unintended mutagenesis and the increasing difficulty of the reassembly of large target molecules of increasing size, which limits the utility of these methods for reassembling long polynucleotide strands.

Another limitation of these methods of fragmentation and reassembly-based gene shuffling is encountered when the parental template polynucleotides are increasingly heterogeneous. In the annealing step of those processes, the small polynucleotide fragments depend upon stabilizing forces that result from base-pairing interactions to anneal properly. As the small regions of annealing have limited stabilizing forces due to their short length, annealing of highly complementary sequences is favored over more divergent sequences. In such instances these methods have a strong tendency to regenerate the parental template polynucleotides due to annealing of complementary single-strands from a particular parental template. Therefore, the parental templates essentially reassemble themselves creating a background of unchanged polynucleotides in the library that increases the difficulty of detecting recombinant molecules. This problem becomes increasingly severe as the parental templates become more heterogeneous, that is, as the percentage of sequence identity between the parental templates decreases. This outcome was demonstrated by Kikuchi, et al., (Gene 243:133-137, 2000) who attempted to generate recombinants between xylE and nahH using the methods of family shuffling reported by Patten et al., 1997; Crameri et al., 1998; Harayama, 1998; Kumamaru et al., 1998; Chang et al., 1999; Hansson et al., 1999). Kikuchi, et al., found that essentially no recombinants (<1%) were generated. They also disclosed a method to improve the formation of chimeric genes by fragmentation and reassembly of single-stranded DNAs. Using this method, they obtained chimeric genes at a rate of 14 percent, with the other 86 percent being parental sequences.

The characteristic of low-efficiency recovery of recombinants limits the utility of these methods for generating novel polynucleotides from parental templates with a lower percentage of sequence identity, that is, parental templates that are more diverse. Accordingly, there is a need for a method of generating gene sequences that addresses these needs.

The present invention provides a method that satisfies the aforementioned needs, and provides related advantages as well.

SUMMARY OF THE INVENTION

The present invention provides a method for reasserting mutations among related polynucleotides, in vitro, by forming heteroduplex molecules and then addressing the mismatches such that sequence information at sites of mismatch is transferred from one strand to the other. In one preferred embodiment, the mismatches are addressed by incubating the heteroduplex molecules in a reaction containing a mismatch nicking enzyme, a polymerase with a 3' to 5' proofreading activity in the presence of dNTPs, and a ligase. These respective activities act in concert such that, at a given site of mismatch, the heteroduplex is nicked, unpaired bases are excised from one of the strands, then replaced using the opposite strand as a template, and nicks are sealed. Output polynucleotides may be amplified before cloning, or cloned directly and tested for improved properties. Additional cycles of mismatch resolution reassortment and testing may lead to further improvement.

In one embodiment, an in vitro method of increasing homogeneity between two strands of the heteroduplex polynucleotide sequence, the method includes mixing the heteroduplex polynucleotide sequence with an effective amount of mismatch-directed strand cleavage activity, proofreading activity, and ligase activity; and allowing sufficient time for homogeneity between two strands of the heteroduplex polynucleotide sequence to result.

In another embodiment an in vitro method of increasing the number of complementary base pairs in a heteroduplex polynucleotide sequence where said heteroduplex polynucleotide sequence has at least two non-complementary nucleotide base pairs, the method includes mixing the heteroduplex polynucleotide sequence with an effective amount of mismatch-directed strand cleavage activity, proofreading activity, and ligase activity; and allowing sufficient time for a number of non-complementary nucleotide base pairs to be converted to complementary base pairs, wherein the homogeneity between the strands is increased by at least one complementary base pair.

In another embodiment an in vitro method of making a population of sequence variants from a heteroduplex polynucleotide sequence wherein said heteroduplex polynucleotide sequence has at least two non-complementary nucleotide base pairs, said method includes mixing copies of the heteroduplex polynucleotide sequence with an effective amount of mismatch-directed strand cleavage activity, proofreading activity, and ligase activity; and allowing sufficient time for a number of non-complementary nucleotide base pairs to be converted to complementary base pairs, wherein a diverse population of polynucleotide sequences results.

In another embodiment an in vitro method of obtaining a polynucleotide sequence encoding a desired functional property, includes preparing at least one heteroduplex polynucleotide sequence; mixing copies of the heteroduplex polynucleotide sequence with an effective amount of mismatch-directed strand cleavage activity, proofreading activity, and ligase activity; and allowing sufficient time for the percentage of complementarity between strands of the heteroduplex polynucleotide sequence to increase, wherein sequence diversity in the population is increased; and screening or selecting a population of variants for the desired functional property.

In another embodiment an in vitro method of obtaining a polynucleotide encoding a desired functional property, includes preparing at least one heteroduplex polynucleotide, mixing copies of the heteroduplex polynucleotide sequence with an effective amount of mismatch-directed strand cleavage activity, proofreading activity, and ligase activity, allowing sufficient time for some or all of the mismatched nucleotide base pairs in the heteroduplex polynucleotide sequence to be converted to complementary bases, wherein a diverse population of polynucleotide sequences results, screening or selecting for a population of variants having a desired functional property, denaturing said population of variants to obtain a population of single stranded polynucleotide sequences, annealing said population of single stranded polynucleotide sequences to form a diverse population heteroduplex polynucleotide sequences, mixing the heteroduplex polynucleotide sequence with an effective amount of mismatch-directed strand cleavage activity, proofreading activity, and ligase activity, allowing sufficient time for some or all of the mismatched nucleotide base pairs in the heteroduplex polynucleotide sequence to be converted to matched base pairs, wherein a diverse population of polynucleotide sequences results, and screening or selecting for a population of variants having a desired functional property. DNA can be converted to RNA prior to screening by transcription of the DNA. A ligase activity can be added to seal the strands after proofreading.

One of the advantages of this method is that the sequence is either circular or linear. This allows for shuffling of nearly unlimited sequence length. The variant polynucleotide sequences have different amounts of complementarity. We report increasing the complementarity in a polynucleotide heteroduplex between two polynucleotides with sequence homology as low as 47%.

This process can occur simultaneously at many sites and on either strand of a given heteroduplex DNA molecule. The result is a randomization of sequence differences among input strands to give a population of sequence variants that is more diverse than the population of starting sequences. In another embodiment, a method of identifying a reasserted DNA molecule encoding a protein with a desired functional property, includes providing at least one single-stranded uracil-containing DNA molecule, which single-stranded uracil-containing DNA molecule, or a complementary strand thereto, encodes a protein; providing one or a plurality of non-identical single-stranded DNA molecules capable of hybridizing to the single-stranded uracil-containing DNA molecule, wherein said DNA molecules encode at least one additional variant of the protein; contacting the single-stranded uracil-containing DNA molecule with at least one single-stranded DNA molecule of step (b), thereby producing an annealed DNA molecule; incubating the annealed DNA molecule with a mismatch endonuclease, proofreading polymerase and a ligase, thereby producing a sequence-reassorted DNA strand annealed to the uracil-containing DNA molecule; amplifying the reasserted DNA strand under conditions wherein the uracil-containing DNA molecule is not amplified, thereby producing a population of reasserted DNA molecules; and, screening or selecting the population of reasserted DNA molecules to identify those that encode a polypeptide having the desired functional property, thereby identifying one or more DNA molecules(s) that encode a polypeptide with the desired functional property. This process can also occur using an RNA molecule as a template.

BRIEF DESCRIPTION OF THE FIGURES

FIG. 2 depicts an exemplary partially complementary nucleic acid population of two molecules. FIG. 2A shows the sequence of two nucleic acid molecules "X" and "Y" having completely complementary top/bottom strands 1+/2− and 3+/4−, respectively. The positions of differing nucleotides between the nucleic acids X and Y are indicated (*). FIG. 2B shows possible combinations of single strands derived from nucleic acids X and Y after denaturing and annealing and indicates which of those combinations would comprise a partially complementary nucleic acid population of two.

FIG. 3 shows nucleic acid sequence for RES I endonuclease (SEQ ID NO: 16) as taught in Example 13.

FIG. 4 shows the corresponding amino acid sequence for RES I (SEQ ID NO: 34).

FIG. 5 shows the nucleic acid sequence for plasmid pBSC3BFP (SEQ ID NO: 32) as taught in Example 14.

FIG. 6 shows the nucleic acid sequence for the tobamovirus movement protein open reading frame of TMV-Cg (SEQ ID NO: 18) as taught in Example 15.

FIG. 7 shows the nucleic acid sequence for the tobamovirus movement protein open reading frame of TMV-Ob (SEQ ID NO: 19) as taught in Example 15.

FIG. 8 shows the nucleic acid sequence for the tobamovirus movement protein open reading frame of TMV-U2 (SEQ ID NO: 20) as taught in Example 15.

FIG. 9 shows a resultant clone from TMV-Cg and ToMv GRAMMR reaction (SEQ ID NO: 21) as taught in Example 15.

FIG. 10 shows a second resultant clone from a TMV-Cg and ToMv GRAMMR reaction (SEQ ID NO: 22) as taught in Example 15.

FIG. 11 shows a resultant clone from a TMV-Ob and ToMv GRAMMR reaction (SEQ ID NO: 23) as taught in Example 15.

FIG. 12 shows a second resultant clone from a TMV-Ob and ToMv GRAMMR reaction (SEQ ID NO: 24) as taught in Example 15.

FIG. 13 shows a resultant clone from a TMV-U2 and ToMv GRAMMR reaction (SEQ ID NO: 25) as taught in Example 15.

FIG. 14 shows a second resultant clone from a TMV-U2 and ToMv GRAMMR reaction (SEQ ID NO: 26) as taught in Example 15.

FIG. 15 shows a resultant clone from a TMV-U1 and ToMv GRAMMR reaction (SEQ ID NO: 27) as taught in Example 15.

FIG. 16 shows a second resultant clone from a TMV-U1 and ToMv GRAMMR reaction (SEQ ID NO: 28) as taught in Example 15.

FIG. 17 shows the nucleic acid sequence for the tobamovirus movement protein open reading frame of TMV (SEQ ID NO: 9) as taught in Example 15.

FIG. 18 shows the nucleic acid sequence for the tobamovirus movement protein open reading frame of ToMV (SEQ ID NO: 10) as taught in Example 15.

DEFINITIONS

Figure 1:
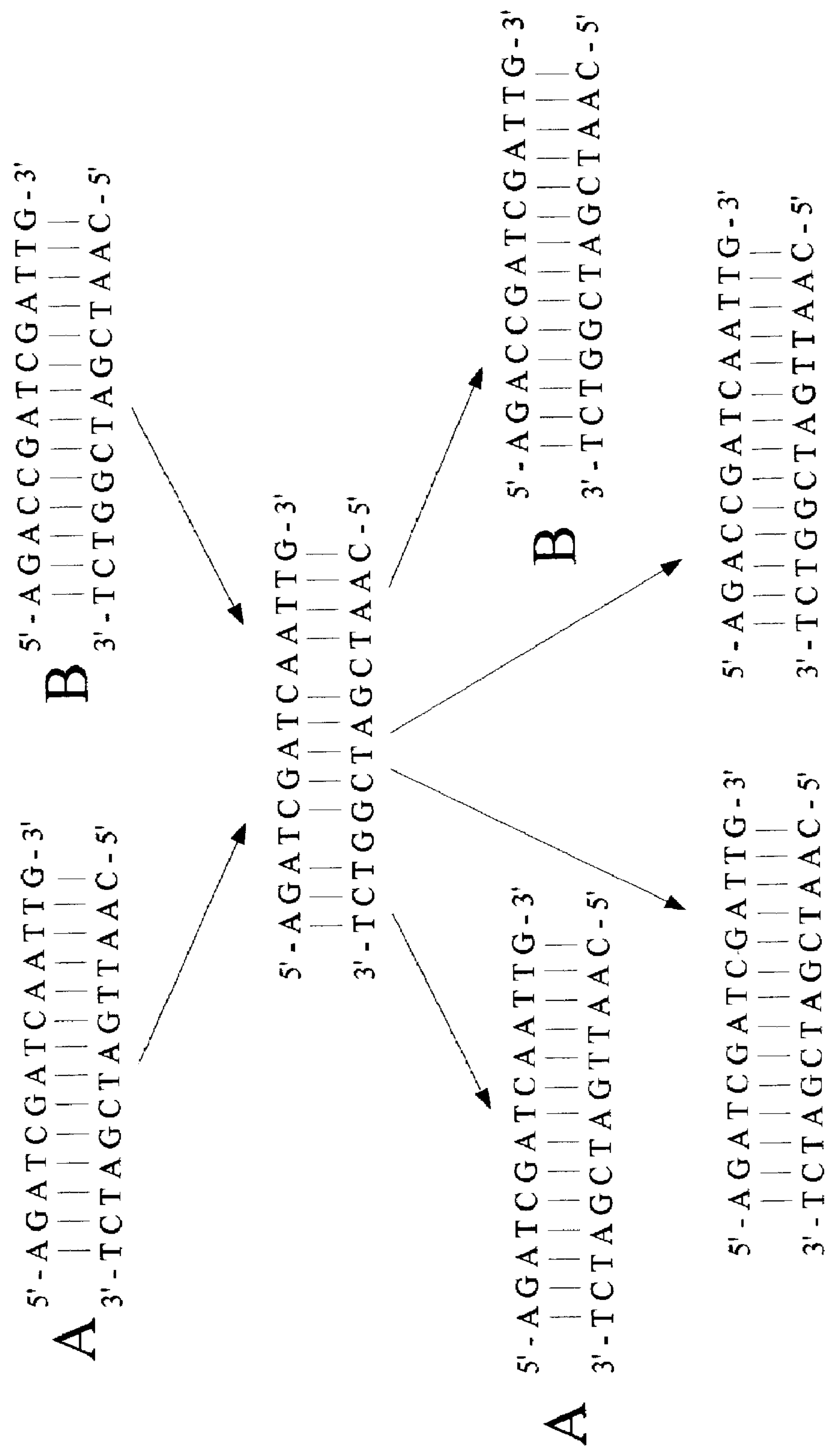
FIG. 1 depicts the process of Genetic Reassortment by Mismatch Resolution (GRAMMR). Reassortment is contemplated between two hypothetical polynucleotides differing at least two nucleotide positions. Annealing between the top strand of A and the bottom strand of B is shown which results in mismatches at the two positions. After the process of reassortment mismatch resolution, four distinct product polynucleotides are seen, the parental types A and B, and the reasserted products X and Y.

In order to provide a clear and consistent understanding of the specification and the claims, including the scope given herein to such terms, the following definitions are provided:

As used herein the term "amplification" refers to a process where the number of copies of a polynucleotide is increased.

As used herein the term "annealing" refers to the formation of at least partially double stranded nucleic acid by hybridization of at least partially complementary nucleotide sequences. A partially double stranded nucleic acid can be due to the hybridization of a smaller nucleic acid strand to a longer nucleic acid strand, where the smaller nucleic acid is 100% identical to a portion of the larger nucleic acid. A partially double stranded nucleic acid can also be due to the hybridization of two nucleic acid strands that do not share 100% identity but have sufficient homology to hybridize under a particular set of hybridization conditions.

As used herein the term "clamp" refers to a unique nucleotide sequence added to one end of a polynucleotide, such as by incorporation of the clamp sequence into a PCR primer. The clamp sequences are intended to allow amplification only of polynucleotides that arise from hybridization of strands from different parents (i.e., heteroduplex molecules) thereby ensuring the production of full-length hybrid products as described previously (Skarfstad, J. Bact, vol 182, No 11, P. 3008-3016).

As used herein the term "cleaving" means digesting the polynucleotide with enzymes or otherwise breaking phosphodiester bonds within the polynucleotide.

As used herein the term "complementary base pair" refers to the correspondence of DNA (or RNA) bases in the double helix such that adenine in one strand is opposite thymine (or uracil) in the other strand and cytosine in one strand is opposite guanine in the other.

As used herein the term "complementary to" is used herein to mean that the complementary sequence is identical to the reverse-complement of all or a portion of a reference polynucleotide sequence or that each nucleotide in one strand is able to form a base-pair with a nucleotide, or analog thereof in the opposite strand. For illustration, the nucleotide sequence "TATAC" is complementary to a reference sequence "GTATA".

As used herein the term "denaturing" or "denatured," when used in reference to nucleic acids, refers to the conversion of a double stranded nucleic acid to a single stranded nucleic acid. Methods of denaturing double stranded nucleic acids are well known to those skilled in the art, and include, for example, addition of agents that destabilize base-pairing, increasing temperature, decreasing salt, or combinations thereof. These factors are applied according to the complementarity of the strands, that is, whether the strands are 100% complementary or have one or more non-complementary nucleotides.

As used herein the term "desired functional property" means a phenotypic property, which include but are not limited to, encoding a polypeptide, promoting transcription of linked polynucleotides, binding a protein, improving the function of a viral vector, and the like, which can be selected or screened for. Polynucleotides with such desired functional properties, can be used in a number of ways, which include but are not limited to expression from a suitable plant, animal, fungal, yeast, or bacterial expression vector, integration to form a transgenic plant, animal or microorganism, expression of a ribozyme, and the like.

As used herein the term "DNA shuffling" is used herein to indicate reassortment of sequence information between substantially homologous but non-identical sequences.

As used herein, the term "effective amount" refers to the amount of an agent necessary for the agent to provide its desired activity. For the present invention, this determination is well within the knowledge of those of ordinary skill in the art.

As used herein the term "Genetic Reassortment by Mismatch Resolution (GRAMMR)" refers to a method for reasserting sequence variations among related polynucleotides by an in vitro method of redistributing sequence variations between non-identical polynucleotide sequences, by making a heteroduplex polynucleotide from two non-identical polynucleotides; introducing a nick in one strand at or near a base pair mismatch site; removing mismatched base(s) from the mismatch site where the nick occurred; and using the opposite strand as template to replace the removed base(s) with bases that complement base(s) in the first strand. By this method, information is transferred from one strand to the other at sites of mismatch.

Multiple sites in a partially complementary molecule can be addressed independently and simultaneously in this procss. The result is an increase in the percentage of complementary base pairs in the polynucleotide sequence.

One or more base pair mismatches between two strands of the heteroduplex polynucleotide sequence are resolved by an in vitro method of mixing the heteroduplex polynucleotide sequence with an effective amount of mismatch-directed strand cleavage activity, proofreading activity, and ligase activity to resolve one or more of the mismatches. By this method, information is transferred from one strand to the other at sites of a mismatch.

A mismatch can be the result of two non-complementary bases occurring opposite each other. A mismatch site can consist of a cluster of any number of unpaired nucleotides, including nucleotide base-pairs that are made unstable by neighboring mismatches. A mismatch can also be the result of one or more bases occurring on one strand that do not have a numerical opposite on the opposite strand. For example, at the site of a mismatch there might be 1 unpaired base on one strand and no unpaired bases on the other strand. This would result in a site of sequence length heterogeneity in which a single unpaired nucleotide is contained in one strand at that site. Depending on the strand that is initially nicked at this site of mismatch, the process of this invention would result in either the insertion of a single base relative to the shorter strand, or in the deletion of a single base relative to the strand that originally had the extra unpaired nucleotide. This principle of transfer of sequence length information from one strand to the other can apply to any site of mismatch where the number of mismatched bases on the two strands do not equal one-another.

Usually many copies of the heteroduplex polynucleotide are present in the reaction. In this situation, sequence information at a mismatch site might be templated from the top strand on one copy of the polynucleotide and from the bottom strand in another copy. Assuming a sufficient number of copies are available, if a single mismatch is present, then two output variants are possible. If two mismatch sites are present then 2 times 2 variants can result. If n mismatch sites are present, then at least 2 to the n power or $2^n$ genetic reassortments are possible by mismatch resolution. The possible result is at least $2^n$ variant polynucleotides. We say at least, because the exact mechanism is not fully understood. It can be speculated that for a mismatch site that is 2 or more bases in length, an individual event might template 1, 2 or more of the mismatched bases. If that is the case, then the result would be an increase in the probable number of variants.

As used herein, the term "GENEWARE" or "GENEWARE®" refers to a viral vector derived at least in part from a Tobamovirus and modified to contain an additional (usually heterologous) subgenomic promoter. A Tobamovirus found in nature, typically contains subgenomic promoters for the movement protein and the coat protein. GENEWARE® is a registered trademark of Large Scale Biology corporation.

As used herein the term "granularity" refers to the amount of a nucleic acid's sequence information from a given parental polynucleotide sequence that occurs as a contiguous sequence in a given progeny polynucleotide.

As used herein the term "template sequence" refers to a first single stranded polynucleotide sequence that is partially complementary to a second polynucleotide sequence such that treatment by GRAMMR results in transfer of genetic information from the template strand to the second strand.

The larger the units of sequence information transferred from a template strand, the higher the granularity. The smaller the blocks of sequence information transferred from the template strand, the lower or finer the granularity. Lower granularity indicates that a DNA shuffling or reassortment method is able to transfer smaller discrete blocks of genetic information from the template strand to the second strand. The advantage of a DNA shuffling or reassortment method with lower granularity is that it is able to resolve smaller nucleic acid sequences from others, and to transfer the sequence information. DNA shuffling or reassortment methods that return primarily high granularity are not readily able to resolve smaller nucleic acid sequences from others.

As used herein the term "heteroduplex polynucleotide" refers to a double stranded polynucleotide formed by annealing single strands, typically separate strands, where the strands are non-identical. A heteroduplex polynucleotide may have unpaired regions existing as single strand loops or bubbles. A heteroduplex polynucleotide region can also be formed by one single-strand polynucleotide wherein partial self-complementarity allows the formation of a stem-loop structure where the annealing portion of the strand is non-identical.

As used herein the term "heteroduplex DNA" refers to a double-stranded DNA formed by annealing single strands, typically separate strands), where the strands are non-identical. A heteroduplex DNA may have unpaired regions existing as single strand loops or bubbles. A heteroduplex DNA region can also be formed by one single-strand polynucleotide wherein partial self-complementarity allows the formation of a stem-loop structure where the annealing portion of the strand is non-identical.

As used herein the term "homologous" means that one single-stranded nucleic acid sequence may hybridize to an at least partially complementary single-stranded nucleic acid sequence. The degree of hybridization may depend on a number of factors including the amount of identity between the sequences and the hybridization conditions such as temperature and salt concentrations as discussed later.

Nucleic acids are "homologous" when they are derived, naturally or artificially, from a common ancestor sequence. During natural evolution, this occurs when two or more descendent sequences diverge from a parent sequence over time, i.e., due to mutation and natural selection. Under artificial conditions, divergence occurs, e.g., in one of two basic ways. First, a given sequence can be artificially recombined with another sequence, as occurs, e.g., during typical cloning, to produce a descendent nucleic acid, or a given sequence can be chemically modified, or otherwise manipulated to modify the resulting molecule. Alternatively, a nucleic acid can be synthesized de novo, by synthesizing a nucleic acid that varies in sequence from a selected parental nucleic acid sequence. When there is no explicit knowledge about the ancestry of two nucleic acids, homology is typically inferred by sequence comparison between two sequences. Where two nucleic acid sequences show sequence similarity over a significant portion of each of the nucleic acids, it is inferred that the two nucleic acids share a common ancestor. The precise level of sequence similarity that establishes homology varies in the art depending on a variety of factors.

For purposes of this disclosure, two nucleic acids are considered homologous where they share sufficient sequence identity to allow GRAMMR-mediated information transfer to occur between the two nucleic acid molecules.

As used herein the term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide.

As used herein the term "increase in percent complementarity" means that the percentage of complementary base-pairs in a heteroduplex molecule is made larger.

As used herein the term, "ligase" refers to an enzyme that establishes a phosphodiester bond between adjacent nucleotides in a nucleic acid.

As used herein the term "mismatch" refers to a base-pair that is unable to form normal base-pairing interactions (i.e., other than "A" with "T" (or "U"), or "G" with "C").

As used herein the term "mismatch resolution" refers to the conversion of a mismatched base-pair into a complementary base-pair.

As used herein the term "mutations" means changes in the sequence of a wild-type or reference nucleic acid sequence or changes in the sequence of a polypeptide. Such mutations can be point mutations such as transitions or transversions. The mutations can be deletions, insertions or duplications.

As used herein, the term "nucleic acid" or "nucleic acid molecule" means a polynucleotide such as deoxyribonucleic acid (DNA) or ribonucleic acid (RNA) and encompasses single-stranded and double-stranded nucleic acid as well as an oligonucleotide. Nucleic acids useful in the invention include genomic DNA, cDNA, mRNA, plasmids, cosmids, PCR products, and synthetic oligonucleotides, and can represent the sense strand, the anti-sense strand, or both. A nucleic acid generally incorporates the four naturally occurring nucleotides adenine, guanine, cytosine, and thymidine/uridine. An invention nucleic acid can also incorporate other naturally occurring or non-naturally occurring nucleotides, including derivatives thereof, so long as the nucleotide derivatives can be incorporated into a polynucleotide by a polymerase at an efficiency sufficient to generate a desired polynucleotide product.

As used herein the term a "parental nucleic acid" refers to a double stranded nucleic acid having a sequence that is 100% identical to an original single stranded nucleic acid in a starting population of partially complementary nucleic acids. Parental nucleic acids would include, for example in the illustration of FIG. 2, nucleic acids X and Y if partially complementary nucleic acid combinations 1+/4− or 2−/3+ were used as a starting population in an invention method.

As used herein the term, "partially complementary" refers to a nucleic acid having a substantially complementary sequence to another nucleic acid but that differs from the other nucleic acid by at least two or more nucleotides.

As used herein the term, "partially complementary nucleic acid population" refers to a population of nucleic acids comprising individual groups of nucleic acids having substantially complementary sequences but no nucleic acids belonging to a particular group having an exact complementary sequence for any other group of sequences in the population.

As used herein, any member of a partially complementary nucleic acid population differs from another nucleic acid of the population, or the complement thereto, by two or more nucleotides. As such, a partially complementary nucleic acid specifically excludes a population containing sequences that are exactly complementary, that is, a complementary sequence that has 100% complementarity. Therefore, each member of such a partially complementary nucleic acid population differs from other members of the population by two or more nucleotides, including both strands. One strand is designated the top strand, and its complement is designated the bottom strand.

As used herein the term, "top" strand refers to a polynucleotide read in the 5' to 3' direction and the "bottom" its complement. It is understood that, while a sequence is referred to as bottom or top strand, such a designation is intended to distinguish complementary strands since, in solution, there is no orientation that fixes a strand as a top or bottom strand.

For example, a population containing two nucleic acid members can be derived from two double stranded nucleic acids, with a potential of using any of the four strands to generate a single stranded partially complementary nucleic acid population. An example of potential combinations of strands of two nucleic acids that can be used to obtain a partially complementary nucleic acid population of the invention is shown in FIG. 2. The two nucleic acid sequences that are potential members of a partially complementary nucleic acid population are designated "X" (AGATCAATTG) and "Y" (AGACCGATTG) (FIG. 2A). The nucleic acid sequences differ at two positions (positions 4 and 6 indicated by "*"). The "top" strand of nucleic acids X and Y are designated "1+" and "3+," respectively, and the "bottom" strand of nucleic acids X and Y are designated "2−" and "4−," respectively.

FIG. 2B shows the possible combinations of the four nucleic acid strands. Of the six possible strand combinations, only the combination of 1+/2−, 1+/4−, 2−/3+, or 3+/4− comprise the required top and bottom strand of a partially complementary nucleic acid population. Of these top/bottom sequence combinations, only 1+/4− or 2−/3+ comprise an example of a partially complementary nucleic acid population of two different molecules because only these combinations have complementary sequences that differ by at least one nucleotide. The remaining combinations, 1+/2− and 2+/4−, contain exactly complementary sequences and therefore do not comprise a partially complementary nucleic acid population of the invention.

In the above described example of a population of two different molecules, a partially complementary population of nucleic acid molecules excluded combinations of strands that differ by one or more nucleotides but which are the same sense, for example, 1+/3+ or 2−/4−. However, it is understood that such a combination of same stranded nucleic acids can be included in a larger population, so long as the population contains at least one bottom strand and at least one top strand. For example, if a third nucleic acid "Z," with strands 5+ and 6− is included, the combinations 1+/3+/6− or 2−/4−/5+ would comprise a partially complementary nucleic acid population. Similarly, any number of nucleic acids and their corresponding top and bottom strands can be combined to generate a partially complementary nucleic acid population of the invention so long as the population contains at least one top strand and at least one bottom strand and so long as the population contains no members that are the exact complement.

The populations of nucleic acids of the invention can be about 3 or more, about 4 or more, about 5 or more, about 6 or more, about 7 or more, about 8 or more, about 9 or more, about 10 or more, about 12 or more, about 15 or more, about 20 or more, about 25 or more about 30 or more, about 40 or more, about 50 or more, about 75 or more, about 100 or more, about 150 or more, about 200 or more, about 250 or more, about 300 or more, about 350 or more, about 400 or more, about 450 or more, about 500 or more, or even about 1000 or more different nucleic acid molecules. A population can also contain about 2000 or more, about 5000 or more, about $1\times10^4$ or more, about $1\times10^5$ or more, about $1\times10^6$ or more, about $1\times10^7$ or more, or even about $1\times10^8$ or more different nucleic acids. One skilled in the art can readily determine a desirable population to include in invention methods depending on the nature of the desired reassortment experiment outcome and the available screening methods, as disclosed herein.

As used herein the term, a "polymerase" refers to an enzyme that catalyzes the formation of polymers of nucleotides, that is, polynucleotides in a template-directed fashion. A polymerase useful in the invention can be derived from any organism or source, including animal, plant, bacterial and viral polymerases. A polymerase can be a DNA polymerase, RNA polymerase, or a reverse transcriptase capable of transcribing RNA into DNA.

As used herein the term "proofreading" describes the property of an enzyme where a nucleotide, such as, a mismatched nucleotide, can be removed in a 3'-to-5' fashion and replaced by, typically, a base-paired nucleotide. In the case of addressing a loop caused by insertion or deletion, proofreading may involve only removal of the mismatched nucleotide(s) or only addition of base-paired nucleotide(s).

As used herein the term, a "recombinant" polynucleotide refers to a polynucleotide that comprises sequence information from at least two different polynucleotides.

As used herein the term "related polynucleotides" means that regions or areas of the polynucleotides are identical and regions or areas of the polynucleotides are non-identical.

As used herein the term DNA "reassortment" is used herein to indicate a redistribution of sequence variations between non-identical sequences.

As used herein the term "replicon" refers to a genetic unit of replication including a length of polynucleotide and its site for initiation of replication.

As used herein the term "sequence diversity" refers to the abundance of non-identical polynucleotides. The term "increasing sequence diversity in a population" means to increase the relative abundance of non-identical polynucleotides in a population.

As used herein the term "sequence variant" refers to a molecule (DNA, RNA polypeptide, and the like) with one or more sequence differences compared to a reference molecule. For example, the sum of the separate independent mismatch resolution events that occur throughout the heteroduplex molecule during the GRAMMR process results in reassortment of sequence information throughout that molecule. The sequence information will reassort in a variety of combinations to generate a complex library of "sequence variants".

As used herein the term "strand cleavage activity" or "cleavage" refers to the breaking of a phosphodiester bond in the backbone of the polynucleotide strand, as in forming a nick. Strand cleavage activity can be provided by an enzymatic agent. Such agents include, but are not limited to CEL I, RES I, T4 endonuclease VII, or T7 endonuclease I.

As used herein the term "Mismatch-directed strand cleavage" means strand cleavage activity by an agent that recognizes a site of a mismatched base pair, group of mismatched base pairs, or extrahelical base or bases on a heteroduplex polynucleotide sequence and cleaves one strand at the site of the mismatch.

As used herein the term "sufficient time" refers to the period of time necessary for a reaction or process to render a desired product. For the present invention, the determination of sufficient time is well within the knowledge of those of ordinary skill in the art. It is noted that "sufficient time" can vary widely, depending on the desires of the practitioner, without impacting on the functionality of the reaction, or the quality of the desired product.

As used herein the term "wild-type" means that a nucleic acid fragment does not contain any mutations. A "wild-type" protein means that the protein will be active at a level of activity found in nature and typically will be the amino acid sequence found in nature. In an aspect, the term "wild type" or "parental sequence" can indicate a starting or reference sequence prior to a manipulation of the invention.

In the polypeptide notation used herein, the left-hand direction is the amino terminal direction and the right-hand direction is the carboxy-terminal direction, in accordance with standard usage and convention. Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction.

DETAILED DESCRIPTION OF THE INVENTION

The present invention provides an in vitro method of making sequence variants from at least one heteroduplex polynucleotide wherein the heteroduplex has at least two non-complementary nucleotide base pairs, the method comprising: preparing at least one heteroduplex polynucleotide; combining said heteroduplex polynucleotide with an effective amount of an agent or agents with strand cleavage activity proofreading activity, and ligase activity; and allowing sufficient time for the percentage of complementarity to increase, wherein at least one or more variants are made.

Another aspect of the present invention is where the heteroduplex polynucleotides are circular, linear or a replicon.

Another aspect of the present invention is where the desired variants have different amounts of complementarity.

Another aspect of the present invention is where the strand cleavage activity, proofreading activity, and ligase activity is added sequentially, or concurrently.

Another aspect of the present invention provides the addition of ligase activity, provided by agents such as, T4 DNA ligase, *E. coli* DNA ligase, or Taq DNA ligase.

In another aspect of the present invention, the strand cleavage activity is provided by an enzyme, such as, CEL I, RES I, T4 endonuclease VII, or T7 endonuclease I.

In another aspect of the present invention, polymerase activity is provided by Pol beta.

In another aspect of the present invention, proofreading activity is provided T4 DNA polymerase or T7 DNA polymerase.

In another aspect of the present invention, the effective amount of strand cleavage activity, and proofreading activity and ligase activity are provided by RES I, T4 DNA polymerase, and *E. coli* DNA ligase.

In another aspect of the present invention, the effective amount of strand cleavage activity, and proofreading activity and ligase activity are provided by RES I, T7 DNA polymerase, and T4 DNA ligase.

Another embodiment of the present invention provides an in vitro method of increasing diversity in a population of sequences, comprising, preparing at least one heteroduplex polynucleotide; combining the heteroduplex polynucleotide with an effective amount of an agent or agents with proofreading activity, ligase activity and strand cleavage activity; and allowing sufficient time for the percentage of complementarity to increase, wherein diversity in the population is increased.

Another embodiment of the present invention provides a method of obtaining a polynucleotide encoding a desired functional property, comprising: preparing at least one heteroduplex polynucleotide; combining said heteroduplex polynucleotide with an effective amount of an agent or agents with proofreading activity, ligase activity and strand cleavage activity; allowing sufficient time for the percentage of complementarity between strands of the heteroduplex polynucleotide to increase, wherein diversity in the population is increased; and screening or selecting a population of variants for the desired functional property.

Another embodiment of the present invention provides a method of obtaining a polynucleotide encoding a desired functional property, comprising: preparing at least one heteroduplex polynucleotide; combining said heteroduplex polynucleotide with an effective amount of an agent or agents with proofreading activity, ligase activity and strand cleavage activity; allowing sufficient time for the percentage of complementarity between strands of the heteroduplex polynucleotide to increase, wherein diversity in the population is increased; converting DNA to RNA; and screening or selecting a population of ribonucleic acid variants for the desired functional property.

Yet another embodiment of the present invention provides a method of obtaining a polypeptide having a desired functional property, comprising: preparing at least one heteroduplex polynucleotide; combining said heteroduplex polynucleotide with an effective amount of an agent or agents with proofreading activity, ligase activity and strand cleavage activity; allowing sufficient time for the percentage of complementarity between strands of said heteroduplex polynucleotide to increase, converting said heteroduplex polynucleotide to RNA, and said RNA to a polypeptide; and screening or selecting a population of polypeptide variants for said desired functional property.

Still another embodiment of the present invention provides a method of obtaining a polynucleotide encoding a desired functional property, comprising: preparing at least one heteroduplex polynucleotide, where the heteroduplex is optionally, about 95%, 90%, 85%, 80%, 75%, 62%, 58% or 47% identical, and about 100 base pairs, 1000 base-pairs, 10,000 base-pairs, or 100,000 base-pairs or more in size; combining said heteroduplex polynucleotide with an effective amount of an agent or agents with proofreading activity, ligase activity and strand cleavage activity; allowing sufficient time for the percentage of complementarity between strands of the heteroduplex polynucleotide to increase, screening or selecting for a population of variants having a desired functional property; denaturing said population of variants to obtain single strand polynucleotides; annealing said single strand polynucleotides to form at least one second heteroduplex polynucleotide; combining said second heteroduplex polynucleotide with an effective amount of an agent or agents with proofreading activity, ligase activity and strand cleavage activity; and allowing sufficient time for the percentage of complementarity between strands of the heteroduplex polynucleotide to increase.

The present invention is directed to a method for generating an improved polynucleotide sequence or a population of improved polynucleotide sequences, typically in the form of amplified and/or cloned polynucleotides, whereby the improved polynucleotide sequence(s) possess at least one desired phenotypic characteristic (e.g., encodes a polypeptide, promotes transcription of linked polynucleotides, binds a protein, improves the function of a viral vector, and the like) which can be selected or screened for. Such desired polynucleotides can be used in a number of ways such as expression from a suitable plant, animal, fungal, yeast, or bacterial expression vector, integration to form a transgenic plant, animal or microorganism, expression of a ribozyme, and the like.

GRAMMR provides for resolution of mismatched base pairs on heteroduplex DNA strands in an in vitro reaction. This reaction begins with cleavage of one strand or the other at or near a mismatch followed by excision of mismatched bases from the cleaved strand and polymerization to fill in the resulting gap with nucleotides that are templated to the sequence of the other strand. The resulting nick can be sealed by ligation to rejoin the backbone. The sum of the separate independent mismatch resolution events that occur throughout the heteroduplex molecule will result in reassortment of sequence information throughout that molecule. The sequence information will reassort in a variety of combinations to generate a complex library of sequence variants.

In one embodiment of GRAMMR, a library of mutants is generated by any method known in the art such as mutagenic PCR, chemical mutagenesis, etc. followed by screening or selection for mutants with a desired property. The mutant DNAs are mixed, denatured to single strands, and allowed to anneal. Partially complementary strands that hybridize will have non-base-paired nucleotides at the sites of the mismatches. Treatment with CEL I (Oleykowski et al., 1998; Yang et al., 2000), or a similar mismatch-directed activity, such as RES I, will cause nicking of one or the other polynucleotide strand 3' of each mismatch. (In addition, CEL I or RES I can nick 3' of an insertion/deletion resulting in reassortment of insertions/deletions.) The presence of a polymerase containing a proofreading activity (e.g., T4 DNA Pol) will allow excision of the mismatch, and subsequent 5'-to-3' polymerase activity will fill in the gap using the other strand as a template. A polymerase that lacks 5'-3' exonuclease activity and strand-displacement activity will fill in the gap and will cease to polymerize when it reaches the 5' end of DNA located at the original CEL I cleavage site, thus re-synthesizing only short patches of sequence. DNA ligase (e.g., T4 DNA ligase or *E. coli* DNA ligase) can then seal the nick by restoring the phosphate backbone of the repaired strand. This process can occur simultaneously at many sites and on either strand of a given heteroduplex DNA molecule. The result is a randomization of sequence differences among input strands to give a population of sequence variants that is more diverse than the population of starting sequences. These output polynucleotides can be cloned directly into a suitable vector, or they can be amplified by PCR before cloning. Alternatively, the reaction can be carried out on heteroduplex regions within the context of a double-stranded circular plasmid molecule or other suitable replicon that can be directly introduced into the appropriate host following the GRAMMR reaction. In another alternative, the output polynucleotides can be transcribed into RNA polynucleotides and used directly, for example, by inoculation of a plant viral vector onto a plant, such as in the instance of a viral vector transcription plasmid. The resulting clones are subjected to a selection or a screen for improvements in a desired property. The overall process can then be repeated one or more times with the selected clones in an attempt to obtain additional improvements.

If the output polynucleotides are cloned directly, there is the possibility of incompletely resolved molecules persisting that, upon replication in the cloning host, could lead to two different plasmids in the same cell. These plasmids could potentially give rise to mixed-plasmid colonies. If it is desired to avoid such a possibility, the output polynucleotide molecules can be grown in the host to allow replication/resolution, the polynucleotides isolated and retransformed into new host cells.

In another embodiment, when sequence input from more than two parents per molecule is desired, the above procedure is performed in a cyclic manner before any cloning of output polynucleotides. After the GRAMMR reaction, the double stranded polynucleotides are denatured, allowed to anneal, and the mismatch resolution process is repeated. After a desired number of such cycles, the output polynucleotides can be cloned directly, introduced into a suitable vector, or they can be amplified by PCR before cloning. The resulting clones are subjected to a selection or a screen for improvements in a desired property.

In another embodiment, a "molecular backcross" is performed to help eliminate the background of deleterious mutations from the desired mutations. A pool of desired mutant DNAs can be hybridized to wild-type DNA to perform the method. Clones can be selected for improvement, pooled, and crossed back to wild-type again until there is no further significant change.

The efficiency of the process is improved by various methods of enriching the starting population for heteroduplex molecules, thus reducing the number of unaltered parental-type output molecules. The mismatched hybrids can be affinity purified using aptamers, dyes, or other agents that bind to mismatched DNA. A preferred embodiment is the use of MutS protein affinity matrix (Wagner et al., *Nucleic Acids Res.* 23(19):3944-3948 (1995); Su et al., *Proc. Natl. Acad. Sci. (U.S.A.),* 83:5057-5061(1986)) or mismatch-binding but non-cleaving mutants of phage T4 endonuclease VII (Golz and Kemper, *Nucleic Acids Research,* 1999; 27: e7).

In one embodiment, the procedure is modified so that the input polynucleotides consist of a single strand of each sequence variant. For example, single-stranded DNAs of opposite strandedness are produced from the different parent sequences by asymmetric PCR to generate partially complementary single-stranded molecules. Annealing of the strands with one-another to make heteroduplex is performed as described in Example 1. Alternatively, single-stranded DNAs can be generated by preferentially digesting one strand of each parental double-stranded DNA with Lambda exonuclease followed by annealing the remaining strands to one-another. In this embodiment, the annealing strands have no 100% complementary strand present with which to re-anneal. Hence, there is a lower background of unmodified polynucleotides, that is, "parental polynucleotides" among the output polynucleotides leading to a higher efficiency of reasserting sequence variations. This increased efficiency will be particularly valuable in situations where a screen rather than a selection is employed to test for the desired polynucleotides.

Another method for heteroduplex formation is to mix the double-stranded parent DNAs, denature to dissociate the strands, and allow the single-stranded DNAs to anneal to one-another to generate a population of heteroduplexes and parental homoduplexes. The heteroduplexes can then be selectively enriched by a heteroduplex capture method such as those described above using MutS or a non-cleaving T4 endonuclease VII mutant. Alternatively, the parental homoduplex molecules in the population may be cleaved by restriction enzymes that overlap with sites of mismatch such that they are not cleaved in the heteroduplex but are cleaved in the parental homoduplex molecules. Uncleaved heteroduplex DNA can then be isolated by size fractionation in an agarose gel as was performed to generate full-length plasmid on full-length plasmid heteroduplex DNA molecules as describe in Example 5. Nick-sealing in those full-length heteroduplexed plasmid molecules was then brought about by incubation with DNA ligase.

In another embodiment, the parental, or input, double-stranded polynucleotides are modified by the addition of "clamp" sequences. One input polynucleotide or pool of polynucleotides is amplified by PCR with the addition of a unique sequence in the 5' primer. The other input polynucleotide or pool is amplified by PCR with the addition of a unique sequence in the 3' primer. The clamp sequences can be designed to contain a unique restriction enzyme site for the 5' end of the gene of interest and another for the 3' end such that, at the step of cloning the products of the GRAMMR reaction, only products with the 5' clamp from the first polynucleotide (or pool) and the 3' end from the second polynucleotide (or pool) will have appropriate ends for cloning. Alternatively, the products of the GRAMMR reaction can be PCR amplified using the unique sequences of the 5' and 3' clamps to achieve a similar result. Hence, there is a lower background of unmodified polynucleotides, that is, "parental polynucleotides" among the output polynucleotide clones leading to a higher efficiency of reasserting sequence variations. This increased efficiency will be particularly valuable in situations where a screen rather than a selection is employed to test for the desired polynucleotides. Optionally, oligonucleotide primers can be added to the GRAMMR reaction that are complementary to the clamp primer sequences such that either parent can serve as the top strand, thus permitting both reciprocal heteroduplexes to participate in the mismatch-resolution reaction.

Another method for generating cyclic heteroduplexed polynucleotides is performed where parental double-stranded DNAs have terminal clamp sequences as described above where the single-stranded clamp sequences extending from one end of the heteroduplex are complementary to single-stranded clamp sequences extending from the other end of the heteroduplex. These complementary, single-stranded clamps are allowed to anneal, thereby circularizing the heteroduplexed DNA molecule. Parental homoduplexes that result from re-annealing of identical sequences have only one clamp sequence and therefore, no complementary single-stranded sequences at their termini with which circularization can occur. Additionally, a DNA polymerase and a DNA ligase can be used to fill-in any gaps in the circular molecules and to seal the nicks in the backbone, respectively, to result in the formation of a population of covalently closed circular heteroduplex molecules. As the covalently-closed circular heteroduplex molecules will not dissociate into their component strands if subjected to further denaturating conditions, the process of denaturation, circularization, and ligation can be repeated to convert more of the linear double-stranded parental duplexes into closed into closed circular heteroduplexes.

In another embodiment, a region of a single-stranded circular phagemid DNA can be hybridized to a related, but non-identical linear DNA, which can then be extended with a polymerase such as T7 DNA polymerase or T4 DNA polymerase plus T4 gene 32 protein, then ligated at the resulting nick to obtain a circular, double-stranded molecule with heteroduplexed regions at the sites of differences between the DNAs. GRAMMR can then be carried out on this molecule to obtain a library of sequence-reassorted molecules.

Alternately, two single-stranded circular phagemid DNAs of opposite strand polarity relative to the plasmid backbone, and parent gene sequences that are the target of the reassortment are annealed to one and other. A region of extensive mismatch will occur where the phage f1 origin sequences reside. Upon GRAMMR treatment, however, this region of extensive mismatch can revert to either parental type sequence restoring a functional f1 origin. These double-stranded molecules will also contain mismatch regions at the sites of differences between the strands encoding the parent genes of interest. GRAMMR can then be carried out on this molecule to obtain a library of sequence re-assorted molecule.

As discussed in the preceding paragraphs, the starting DNA or input DNA can be of any number of forms. For example, input DNA can be full-length, single stranded and of opposite sense, as is taught in Example 1. Alternatively, the input DNA can also be a fragment of the full-length strand. The input DNAs can be double-stranded, either one or both, or modified, such as by, methylation, phosphorothiolate linkages, peptide-nucleic acid, incorporation of uracil into the DNA, substitution of RNA in one or both strands, or the like. Either strand of a duplex can be continuous along both strands, discontinuous but contiguous, discontinuous-with overlaps, or discontinuous with gaps.

GRAMMR can also be applied to DNA fragmentation and reassembly-based DNA shuffling schemes. For instance, in methods where gene fragments are taken through cycles of denaturation, annealing, and extension in the course of gene reassembly, GRAMMR can be employed as an intermediate step.

In one such embodiment, the DNA from a gene, or pool of mutant genes is fragmented by enzymatic, mechanical or chemical means, and optionally a size range of said fragments is isolated by a means such as separation on an agarose gel. The starting polynucleotide, such as a wild-type, or a desired variant, or a pool thereof, is added to the fragments and the mixture is denatured and then allowed to anneal. The annealed polynucleotides are treated with a polymerase to fill in the single stranded gaps using the intact strand as a template. The resulting partially complementary double strands will have non-base-paired nucleotides at the sites of the mismatches. Treatment with CEL I (Oleykowski et al., 1998; Yang et al., 2000), or an agent with similar activity, such as RES I, will cause nicking of one or the other polynucleotide strand 3' of each mismatch. Addition of a polymerase containing a proofreading activity, such as T4 DNA Polymerase, will allow excision of the mismatch, and subsequent 5'-to-3' polymerase activity will fill in the gap using the other strand as a template. A DNA ligase, such as, T4 DNA Ligase, can then seal the nick by restoring the phosphate backbone of the repaired strand. The result is a randomization of sequence variation among input strands to give output strands with potentially improved properties. These output polynucleotides can be cloned directly into a suitable vector, or they can be amplified by PCR before cloning. The resulting clones are subjected to a selection or a screen for improvements in a desired property.

In one such embodiment, the DNA from a pool of mutant genes is fragmented by enzymatic, mechanical or chemical means, or fragments are generated by limited extension of random oligonucleotides annealed to parental templates (U.S. Pat. No. 5,965,408), and optionally a size range of said fragments is isolated by a means such as separation on an agarose gel. The mixture is denatured and then allowed to anneal. The annealed polynucleotides are optionally treated with a polymerase to fill in the single stranded gaps. The resulting partially complementary double-strand fragments will have non-base paired nucleotides at the sites of the mismatches. Treatment with CEL I (Oleykowski et al., 1998; Yang et al., 2000), or an agent with similar activity, such as RES I, will cause nicking of one or the other polynucleotide strand 3' of each mismatch. The activity of a polymerase containing a proofreading activity, such as T4 DNA Polymerase, will allow excision of the mismatch, and subsequent 5'-to-3' polymerase activity will fill in the gap using the other strand as a template. Optionally, DNA ligase, such as, T4 DNA Ligase, can then seal the nick by restoring the phosphate backbone of the repaired strand. The result is a randomization of sequence variation among input strands to give output strands with potentially improved properties. Subsequent rounds of denaturing, annealing, and GRAMMR allows gene reassembly. PCR can be used to amplify the desired portion of the reassembled gene. These PCR output polynucleotides can be cloned into a suitable vector. The resulting clones are subjected to a selection or a screen for the desired functional property.

Another embodiment of the present invention provides starting with a continuous scaffold strand to which fragments of another gene or genes anneal. The flaps and gaps are trimmed and filled as is described in Coco, et al., Nature Biotech 19 (01)354; U.S. Pat. No. 6,319,713, and GRAMMR is performed. In this process, GRAMMR would bring about further sequence reassortment by permitting transfer of sequence information between the template strand and the strand resulting from flap and gap trimming and ligation. This method provides the benefits of incorporating specific sequence patches into one continuous strand followed by GRAMMR of residues that mismatch with the scaffold. By annealing many fragments simultaneously to the same sequence or gene, many individual sites can be addressed simultaneously, thereby allowing reassortment of multiple sequences or genes at once. In the present embodiment, the scaffold is not necessarily degraded, rather the duplex can be directly cloned, or amplified by PCR prior to cloning. Exhaustive mismatch resolution will result in a perfectly duplexed DNA. Partial mismatch resolution will result in essentially two different reasserted products per duplex.

As can be appreciated from the present disclosure, GRAMMR can also be applied to a variety of methods that include the annealing of related DNAs as a step in their process. For example, many site-directed mutagenesis protocols call for the annealing of mutant-encoding DNA molecules to a circular DNA in single-stranded form, either phagemid or denatured plasmid. These DNAs are then extended with a polymerase, followed by treatment with ligase to seal the nick, with further manipulation to remove the parental sequence, leaving the desired mutation or mutations incorporated into the parental genetic background. Though these protocols are generally used to incorporate specific mutations into a particular DNA sequence, it is feasible that the GRAMMR reaction can be applied to the heteroduplexed molecules generated in such a process to reassort sequence variations between the two strands, thereby resulting in a diverse set of progeny with reasserted genetic variation.

Another embodiment provides for sequential rounds of reassortment on only a particular region of the DNA of interest. For example, DNA fragments are annealed to a circular single-strand phagemid DNA, and GRAMMR is performed. The fragments can be treated in order to prevent them from being physically incorporated into the output material. For example, they can be terminated at the 3' end with di-deoxy residues making them non-extendible. Multiple rounds of reassortment can be performed, but only modified molecules from the original input single stranded DNA clone will be recovered. The consequence will be that the DNA fragments used in this reassortment will contribute only sequence information to the final product and will not be physically integrated into the final recoverable product.

GRAMMR can be used for protein, peptide, or aptamer display methods to obtain recombination between library members that have been selected. As fragmentation of the input DNAs is not required for GRAMMR, it may be possible to reassort sequence information between very small stretches of sequence. For instance, DNAs encoding small peptides or RNA aptamers that have been selected for a particular property such as target binding can be reasserted. For annealing to occur between the selected DNA molecules, some level of sequence homology should be shared between the molecules, such as at the 5' and 3' regions of the coding sequence, in regions of the randomized sequence segment that bear similarity because of similar binding activities, or through the biasing of codon wobble-base identity to a particular set of defaults.

Manipulation of the reaction temperature at which GRAMMR is conducted can be useful. For example, lower temperatures will help to stabilize heteroduplexes allowing GRAMMR to be performed on more highly mismatched substrates. Likewise, additives that affect base-pairing between strands, such as salts, PEG, formamide, etc, can be used to alter the stability of the heteroduplex in the GRAMMR reaction, thereby affecting the outcome of the reaction.

Another embodiment provides for zonal mutagenesis by GRAMMR, that is, random or semi-random mutations at, and in the immediate vicinity of, mismatched residues using nucleotide analogues that have multiple base-pairing potential. This provides for concentration of essentially random mutagenesis at a particular point of interest, and adds another benefit to the present invention. Groups of genes that are similar, but have slightly different functions from one-another, for example, many enzymes, will exhibit moderate sequence differences from one-another in regions that will be operative for their own particular activities. These activities, can include substrate preference, binding partners, regulatory sites, or the like. Gene sequences that govern these functions should be heterogeneous within the population of related genes. Since it is known that the specificity of such function is associated with these amino acids and their neighbors, GRAMMR mutagenesis, in addition to reasserting sequence information between genes, may also be used to direct random mutagenesis to these regions to evolve their function, while not disturbing other sequences, such as structural framework, invariant residues, and other such important sites, that are potentially less tolerant to randomization.

Different enzymes with distinct functions will not differ just in the operative regions, such as active sites and regulatory sites. They are likely to have other differences from one another that arise through genetic drift. Further randomization in the locales of such changes might therefore be considered neutral, minimally important, or deleterious to the outcome of a mutagenesis experiment. In order to direct the random mutagenesis away from such inconsequential sites, and toward sites that might present a better result for random mutagenesis, such as the active site of an enzyme, the codon usage bias of the genes could be manipulated to decrease or increase the overall level of nucleotide complementarity in those regions. If regions of greater complementarity are less susceptible to GRAMMR than regions of lesser complementarity, then the degree of GRAMMER-directed zonal random mutagenesis at a given site can be modulated.

In any DNA shuffling experiment, it is desirable to minimize the proportion of non-shuffled, or parental, DNAs that are obtained within the population of shuffled progeny. Numerous approaches may be used to accomplish this. In a plasmid-on-plasmid DNA shuffling format, where the genes to be shuffled are present on separate, but otherwise identical plasmids, each plasmid is linearized at one or another different unique restriction sites that are present. After removal of the restriction endonucleases, the linearized DNAs are mixed, melted apart, and allowed to anneal so that populations of heteroduplex DNA form that are either nicked, closed circular heteroduplex molecules, or are double stranded and linear homoduplexes. It is the population of circular double-stranded heteroduplex DNA molecules that represents the desired substrate for the GRAMMR reaction. One can either enrich this desired population by gel fractionation or use one or a number of methods that do not require physical separation of this population, but rather, discourages the recovery of non-shuffled parental molecules. Several such methods are listed below.

First, after GRAMMR reaction of the mixed population of linear parental homoduplex and circular double-stranded heteroduplex, transformation of *E. coli* is generally performed. Since circular DNA is vastly more efficient at transforming *E. coli* than its linearized counterpart, the parental homoduplexes can be strongly discriminated against at this step by preventing their circularization into transformation-competent molecules. The use of *E. coli* DNA ligase as the ligase component of the GRAMMR reaction will serve to prevent recircularization of parental homoduplex, as it more efficiently seals nicks than joins short cohesive termini that result from restriction endonuclease cleavage. Additionally, this enzyme very inefficiently ligates blunt ends. As a result of using this strategy, the progeny resulting from transformation of *E. coli* with the GRAMMR reaction are depleted of non-shuffled parental genes and enriched for molecules that entered the GRAMMR reaction as heteroduplex substrates.

Another method for excluding parental gene contamination from the population of GRAMMR output molecules is to position the plasmid linearization sites within a selectable marker. The sites should be of sufficient distance from one another to allow annealing to take place between staggered ends of a heteroduplex, and should either have overhangs that can be filled-in or trimmed off, or cause a deletion of sequence upon cleavage. As above, the plasmids containing the genes to be shuffled are linearized at one or other of the sites. After removal of the restriction endonucleases, the linearized DNAs are mixed, melted, and allowed to anneal. The resulting sample is made up of a mixture of circular heteroduplexes and of linear homoduplexes. This sample can then be treated with a proofreading polymerase such as T4 DNA polymerase in the presence of dNTPs. The circular homoduplexes should be unaffected, whereas the linear parental homoduplexes will have been blunted at their termini, effectively adding or deleting bases to the sequence of the selectable marker if that molecule becomes recircularized at any point in the GRAMMR reaction or after transformation into *E. coli*. If the addition or deletion of these sequences results in disruption of the function of the selectable marker, then the resulting molecules will not be recovered under appropriate selection.

Another method one can use to prevent unshuffled parental contamination of the shuffled library is to dephosphorylate the linearized DNAs prior to melting and annealing. Linear homoduplex molecules will be rendered unable to ligate into circular molecules whereas circular heteroduplexes will simply contain a single nick in each strand, but will still remain circular, and thus competent for efficient transformation into *E. coli*.

Another method one can use to prevent unshuffled parental contamination of the shuffled library is to digest with enzymes whose recognition sites are overlapped by mismatches in the heteroduplexed molecules. Digestion of the parental homoduplexes at those sites will render the resulting molecules linear so that they may be subject to any of the treatments described above to reduce parental contamination. The resulting molecules may also be made smaller, facilitating separation from the intact circular heteroduplex molecules.

If, in addition to excluding unshuffled parental molecules from a shuffling experiment, one desires to prevent shuffling between any two or more genes of a population of two or more parent genes, the same principles described above can be applied.

In the current invention the random reassortment occurs in an in vitro DNA mismatch-resolution reaction. This method does not require any steps of "gene reassembly" that serve as the foundation for the earlier mutation reassortment ("shuffling") methods. Instead, it is based upon the ability of a reconstituted or artificial DNA mismatch resolving system to transmit sequence variations from one or more strands of DNA into another DNA strand by hybridization and mismatch resolution in vitro.

In general, standard techniques of recombinant DNA technology are described in various publications, e.g., (Ausubel, 1987; Ausubel, 1999; Sambrook et al., 1989), each of which is incorporated herein in their entirety by reference. Polynucleotide modifying enzymes were used according to the manufacturers recommendations. If desired, PCR amplimers for amplifying a predetermined DNA sequence may be chosen at the discretion of the practitioner.

It is noted that each of the activities taught in the present invention that are involved in the GRAMMR reaction can be interchanged with a functional equivalent agent with similar activity, and that such changes are within the scope of the present invention. For instance, as was indicated in Example 2, Taq DNA ligase could substitute for T4 DNA ligase. Other ligases can be substituted as well, such as *E. coli* DNA ligase. Likewise, as shown in Example 8, T7 DNA polymerase can be substituted for T4 DNA polymerase. Other enzymes with appropriate proofreading activity can function in place of any of these enzymes for the proofreading activity needed for the GRAMMR reaction. In a similar way, any polymerase with functionally equivalent activity to those demonstrated to work for GRAMMR can be used for substitution.

Strand cleavage may be brought about in a number of ways. In addition to CEL I, a number of functionally equivalent, and potentially similar activities found in extracts from a variety of plant species (Oleykowski, Nucleic Acids Res 1998;26: 4597-602) may be used. Other mismatch-directed endonucleases such as T4 endonuclease VII, T7 endonuclease I, and SP nuclease (Oleykowski, Biochemistry 1999; 38: 2200-5) may be used. Another particularly useful mismatch-directed endonuclease is RES I.

Another embodiment to the present invention is directed to recombinant plant viral nucleic acids and recombinant viruses which are stable for maintenance and transcription or expression of non-native (foreign) nucleic acid sequences and which are capable of systemically transcribing or expressing such foreign sequences in the host plant. More specifically, recombinant plant viral nucleic acids according to the present invention comprise a native plant viral subgenomic promoter, at least one non-native plant viral subgenomic promoter, a plant viral coat protein coding sequence, and optionally, at least one non-native, nucleic acid sequence.

The present invention provides nucleic acid molecules comprising a nucleic acid sequence which include SEQ ID NO:01, SEQ ID NO:02, SEQ ID NO:03, or SEQ ID NO:04, useful as vectors or plasmids for the expression of CEL I endonuclease. The nucleic acid molecules of SEQ ID NO:03, and SEQ ID NO:04 are CEL I open reading frames contained within SEQ ID NO:01 and SEQ ID NO:02, respectively. The preparation and use of the nucleic acid molecules of SEQ ID NO:01, SEQ ID NO:02, SEQ ID NO:03 and SEQ ID NO:04, are further taught in Example 12 herein. The present invention also provides nucleic acid molecules comprising the nucleic acid sequence of FIG. 3 (SEQ ID NO:16), useful as vectors or plasmids for the expression of RES I endonuclease.

The present invention further provides a plant cell comprising a vector or plasmid comprising of a nucleic acid sequence selected from the group consisting of SEQ ID NO:01, SEQ ID NO:02, SEQ ID NO:03, SEQ ID NO:04, or FIG. 3 (SEQ ID NO:16) where the plant cell is a host cell, or production cell.

The present invention also provides a recombinant plant viral nucleic acid comprising of at least one sub-genomic promoter capable of transcribing or expressing CEL I or RES I endonuclease in a plant cell, wherein the plant cell is a host cell, or production cell.

The present invention also provides a process for expressing CEL I or RES I endonuclease using a recombinant plant viral nucleic acid comprising of a nucleic acid sequence selected from the group consisting of SEQ ID NO:01, SEQ ID NO:02, SEQ ID NO:03, SEQ ID NO:04, or FIG. 3 (SEQ ID NO:16).

In another embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a fusion protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In another embodiment, a recombinant plant viral nucleic acid is provided as in the first embodiment except that the native coat protein coding sequence is placed adjacent one of the non-native coat protein subgenomic promoters instead of a non-native coat protein coding sequence.

In yet another embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In another embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) in the host to produce the desired product.

As used herein, the term "host" refers to a cell, tissue or organism capable of replicating a vector or plant viral nucleic acid and which is capable of being infected by a virus containing the viral vector or plant viral nucleic acid. This term is intended to include prokaryotic and eukaryotic cells, organs, tissues or organisms, where appropriate.

As used herein, the term "infection" refers to the ability of a virus to transfer its nucleic acid to a host or introduce viral nucleic acid into a host, wherein the viral nucleic acid is replicated, viral proteins are synthesized, and new viral particles assembled. In this context, the terms "transmissible" and "infective" are used interchangeably herein.

As used herein, the term "non-native" refers to any RNA sequence that promotes production of subgenomic mRNA including, but not limited to, 1) plant viral promoters such as ORSV and brome mosaic virus, 2) viral promoters from other organisms such as human Sindbis viral promoter, and 3) synthetic promoters.

As used herein, the term "phenotypic trait" refers to an observable property resulting from the expression of a gene.

As used herein, the term "plant cell" refers to the structural and physiological unit of plants, consisting of a protoplast and the cell wall.

As used herein, the term "plant organ" refers to a distinct and visibly differentiated part of a plant, such as root, stem, leaf or embryo.

As used herein, the term "plant tissue" refers to any tissue of a plant in planta or in culture. This term is intended to include a whole plant, plant cell, plant organ, protoplast, cell culture, or any group of plant cells organized into a structural and functional unit.

As used herein, the term "production cell" refers to a cell, tissue or organism capable of replicating a vector or a viral vector, but which is not necessarily a host to the virus. This term is intended to include prokaryotic and eukaryotic cells, organs, tissues or organisms, such as bacteria, yeast, fungus and plant tissue.

As used herein, the term "promoter" refers to the 5' -flanking, non-coding sequence adjacent a coding sequence which is involved in the initiation of transcription of the coding sequence.

As used herein, the term "protoplast" refers to an isolated plant cell without cell walls, having the potency for regeneration into cell culture or a whole plant.

As used herein, the term "recombinant plant viral nucleic acid" refers to plant viral nucleic acid, which has been modified to contain non-native nucleic acid sequences.

As used herein, the term "recombinant plant virus" refers to a plant virus containing the recombinant plant viral nucleic acid.

As used herein, the term "subgenomic promoter" refers to a promoter of a subgenomic mRNA of a viral nucleic acid.

As used herein, the term "substantial sequence homology" refers to nucleotide sequences that are substantially functionally equivalent to one another. Nucleotide differences between such sequences having substantial sequence homology will be de minimus in affecting function of the gene products or an RNA coded for by such sequence.

As used herein, the term "transcription" refers to production of an RNA molecule by RNA polymerase as a complementary copy of a DNA sequence.

As used herein, the term "vector" refers to a self-replicating DNA molecule which transfers a DNA segment between cells.

As used herein, the term "virus" refers to an infectious agent composed of a nucleic acid encapsidated in a protein. A virus may be a mono-, di-, tri- or multi-partite virus, as described above.

The present invention provides for the infection of a plant host by a recombinant plant virus containing recombinant plant viral nucleic acid or by the recombinant plant viral nucleic acid which contains one or more non-native nucleic acid sequences which are transcribed or expressed in the infected tissues of the plant host. The product of the coding sequences may be recovered from the plant or cause a phenotypic trait in the plant.

The first step in achieving any of the features of the invention is to modify the nucleotide sequences of the plant viral nucleotide sequence by known conventional techniques such that one or more non-native subgenomic promoters are inserted into the plant viral nucleic acid without destroying the biological function of the plant viral nucleic acid. The subgenomic promoters are capable of transcribing or expressing adjacent nucleic acid sequences in a plant host infected by the recombinant plant viral nucleic acid or recombinant plant virus. The native coat protein coding sequence may be deleted in two embodiments, placed under the control of a non-native subgenomic promoter in a second embodiment, or retained in a further embodiment. If it is deleted or otherwise inactivated, a non-native coat protein gene is inserted under control of one of the non-native subgenomic promoters, or optionally under control of the native coat protein gene subgenomic promoter. The non-native coat protein is capable of encapsidating the recombinant plant viral nucleic acid to produce a recombinant plant virus. Thus, the recombinant plant viral nucleic acid contains a coat protein coding sequence, which may be native or a normative coat protein coding sequence, under control of one of the native or non-native subgenomic promoters. The coat protein is involved in the systemic infection of the plant host.

Some of the viruses which meet this requirement, and are therefore suitable, include viruses from the tobacco mosaic virus group such as Tobacco Mosaic virus (TMV), Cowpea Mosaic virus (CMV), Alfalfa Mosaic virus (AMV), Cucumber Green Mottle Mosaic virus watermelon strain (CGMMV-W) and Oat Mosaic virus (OMV) and viruses from the brome mosaic virus group such as Brome Mosaic virus (MBV), broad bean mottle virus and cowpea chlorotic mottle virus. Additional suitable viruses include Rice Necrosis virus (RNV), and geminiviruses such as tomato golden mosaic virus (TGMV), Cassaya latent virus (CLV) and maize streak virus (MSV).

Another embodiment of the present invention is a recombinant plant viral nucleic acid, which further comprises one or more non-native nucleic acid sequences capable of being transcribed in the plant host. The non-native nucleic acid sequence is placed adjacent one or the non-native viral subgenomic promoters and/or the native coat protein gene promoter depending on the particular embodiment used. The non-native nucleic acid is inserted by conventional techniques, or the non-native nucleic acid sequence can be inserted into or adjacent the native coat protein coding sequence such that a fusion protein is produced. The non-native nucleic acid sequence, which is transcribed, may be transcribed as an RNA capable of regulating the expression of a phenotypic trait by an anti-sense mechanism. Alternatively, the non-native nucleic acid sequence in the recombinant plant viral nucleic acid may be transcribed and translated in the plant host, to produce a phenotypic trait. The non-native nucleic acid sequence(s) may also code for the expression of more than one phenotypic trait. The recombinant plant viral nucleic acid containing the non-native nucleic acid sequence is constructed using conventional techniques such that non-native nucleic acid sequence(s) are in proper orientation to whichever viral subgenomic promoter is utilized.

CEL I is a Mismatch Endonuclease

CEL I is a mismatch endonuclease isolated from celery. The use of CEL I in a diagnostic method for the detection of mutations in targeted polynucleotide sequences, in particular, those associated with cancer, is disclosed in U.S. Pat. No. 5,869,245. Methods of isolating and preparing CEL I are also disclosed in this patent. However, there is no disclosure in this patent relating to the use of CEL I in DNA sequence reassortment.

Nucleic acid molecules that encode CEL I are disclosed in PCT Application Publication No. WO 01/62974 A1. As with U.S. Pat. No. 5,869,245, the use of CEL I in a diagnostic method for the detection of mutations in targeted polynucleotide sequences associated with cancer is disclosed. Also similarly, there is no disclosure relating to the use of CEL I in DNA sequence reassortment.

RES I is a Mismatch Endonuclease

The use of RES I mismatch endonuclease is contemplated in diagnostic methods for the detection of mutations in targeted polynucleotide sequences, in particular, those associated with cancer. Examples of some of these types of diagnostic methods are disclosed in U.S. Pat. No. 5,869,245, Sokurenko, et al., and Del Tito, et al.

The reactivity of Endonuclease VII of phage T4 with DNA-loops of eight, four, or one nucleotide, or any of 8 possible base mismatches in vitro is disclosed in "Endonuclease VII of Phage T4 Triggers Mismatch Correction in Vitro" Solaro, et al., J Mol Biol 230(93)868. The publication reports a mechanism where Endonuclease VII introduces double stranded breaks by creating nicks and counternicks within six nucleotides 3' of the mispairing. The publication discloses that a time delay between the occurrence of the first nick and the counternick was sufficient to allow the 3'-5' exonuclease activity of gp43 to remove the mispairing and its polymerase activity to fill in the gap before the occurrence of the counternick. Nucleotides are erased from the first nick, which is located 3' of the mismatch on either strand and stops 5' of the mismatch at the first stable base-pair. The polymerase activity proceeds in the 5' to 3' direction towards the initial nick, which is sealed by DNA ligase. As a result, very short repair tracks of 3 to 4 nucleotides extend across the site of the former mismatch. The publication concludes with a discussion regarding the various activities Endonuclease VII may have within phage T4. However, the publication does not disclose any practical utility for Endonuclease VII outside of phage T4, and there is no disclosure regarding its applicability in DNA reassortment.

A method for creating libraries of chimeric DNA sequences in vivo in *Escherichia coli* is disclosed in *Nucleic Acids Research,* 1999, Vol 27, No. 18, e18, Volkov, A. A., Shao, Z., and Arnold, F. H. The method uses a heteroduplex formed in vitro to transform *E. coli* where repair of regions of non-identity in the heteroduplex creates a library of new, recombined sequences composed of elements of each parent. Although the publication discloses the use of this method as a convenient addition to existing DNA recombination methods, that is, DNA shuffling, the disclosed method is limited to the in vivo environment of *E. coli*. The publication states that there is more than one mechanism available for mismatch repair in *E. coli*, and that the 'long patch' repair mechanism, which utilizes the MutS/L/H enzyme system, was probably responsible for the heteroduplex repair.

The following non-limiting examples are provided to illustrate the present invention.

EXAMPLE 1

Cleavage of Mismatched DNA Substrate by CEL I

This example teaches the preparation of CEL I enzyme and its use in the cleavage of mismatched DNA substrate.

CEL I enzyme was prepared from celery stalks using the homogenization, ammonium sulfate, and Concanavalin A-Sepharose protocol described by Yang et al. (*Biochemistry,* 39:3533-3541 (2000), incorporated herein by reference. A 1.5 kg sample of chilled celery stalks was homogenized with a juice extractor. One liter of juice was collected, adjusted to 100 mM Tris-HCL, pH 7.7 with 100 micromolar phenylmethylsulfonyl fluoride (PMSF), and filtered through two layers of miracloth. Solid $(NH_4)_2SO_4$ was slowly added to 25% saturation while stirring on ice. After 30 minutes, the suspension was centrifuged at 27,000g for 1.5 hours at 4° C. The supernatants were collected and adjusted with solid $(NH_4)_2SO_4$ to 80% saturation while stirring on ice followed by centrifugation at 27,000 g for 2 hours. The pellets were resuspended in buffer B (0.1 M Tris-HCL, pH 7.7, 0.5 M KCl, 100 micromolar PMSF) and dialyzed against the same buffer.

Conconavalin A (ConA) Sepharose affinity chromatography was performed by first incubating the dialyzed sample with 2 ml of ConA resin overnight with gentle agitation. The ConA resin was then packed into a 0.5 cm diameter column and washed with several column volumes of buffer B. Elution was performed using 0.3 M alpha-methyl-mannoside in buffer B. Fractions were collected in 1 ml aliquots. Fractions were assayed for mismatch cleavage activity on a radiolabeled mismatch substrate by incubating 0.1 microliter of each fraction with the mismatched probe in buffer D (20 mM Tris-HCL, pH 7.4, 25 mM KCL, 10 MM $MgCl_2$) for 30 minutes at 45° C. as described by Oleykowski et al. (Nucleic Acids Research 26: 4597-4602 (1998), incorporated herein by reference. Reaction products were visualized by separation on 10% TBE-PAGE gels containing 7% urea (Invitrogen), followed by autoradiography. Aliquots of the CEL I fractions having mismatch cleavage activity were stored frozen at −20° C. A series of five-fold dilutions of CEL I fraction #5 were then analyzed for mismatch cleavage of radiolabeled mismatch substrate. Reactions were performed either in buffer D, New England BioLabs (NEB) T4 DNA ligase buffer (50 mM Tris-HCL, pH 7.5, 10 mM $MgCl_2$, 10 mM dithiothreitol (DTT), 1 mM ATP, 25 microgram/ml BSA), or Gibco/BRL T4 DNA ligase buffer (50 mM Tris-HCL, pH 7.6, 10 MM $MgCl_2$, 1 mM DTT, 1 mM ATP, 5%(w/v) polyethylene glycol-8000). Reaction products were visualized as above. Cleavage activity in buffer D and in NEB T4 DNA ligase buffer were found to be roughly equivalent, whereas cleavage in the PEG-containing Gibco/BRL ligase buffer was enhanced by five to ten-fold compared to the other buffers.

Additional analysis of CEL I activity was carried out using defined heteroduplex DNAs from two different Green Fluorescent Protein (GFP) genes as substrate. This GFP heteroduplex substrate was prepared by annealing single stranded DNAs corresponding to cycle 3 GFP (SEQ ID NO: 30) on the sense strand and wild-type GFP (SEQ ID NO: 29) on the antisense strand. The single-stranded DNAs had been synthesized by asymmetric PCR and isolated by agarose gel electrophoresis. After annealing by heating to 90° C. and cooling to room-temperature in the presence of 1× NEB restriction enzyme buffer 2 (10 mM Tris-HCL, pH 7.9, 10 mM $MgCl_2$, 50 mM NaCl, 1 mM dithiothreitol), the heteroduplex DNA was isolated by agarose gel electrophoresis followed by excision of the heterduplex band and extraction using Qiaquick DNA spin columns. A total of twenty eight mismatches, one or two nucleotides in length, occur throughout the length of the heteroduplex molecule. The distribution of the mismatches ranges from small clusters of several mismatches separated by one or two nucleotides to mismatches separated by more than thirty base pairs on either side.

A series of three-fold dilutions of CEL I in 1× NEB T4 DNA ligase buffer were prepared and one microliter aliquots of each were incubated in two separate series of 10 microliter reactions, each containing as substrate either 0.5 microgram of a supercoiled plasmid preparation or one hundred nanograms of the cycle3/wild-type GFP heteroduplex. All reactions took place in 1× NEB T4 DNA ligase buffer. Reactions were incubated at 45° C. for 30 minutes and run on 1.5% TBE-agarose gel in the presence of ethidium bromide.

Treatment of the supercoiled plasmid preparation with increasing amounts of CEL I resulted in the conversion of supercoiled DNA to nicked circular, then linear molecules, and then to smaller fragments of DNA of random size. Treatment of the mismatched GFP substrate with the CEL I preparation resulted in the digestion of the full-length heteroduplex into laddered DNA bands which are likely to represent cleavage on opposite DNA strands in the vicinity of clusters of mismatches. Further digestion resulted in the conversion of the mismatched GFP substrate to smaller DNAs that may represent a limit digest of the heteroduplex DNA by the CEL I preparation.

EXAMPLE 2

Conservation of Full Length GFP Gene with Mismatch Resolution Cocktails

This example teaches various mismatch resolution cocktails that conserve the full length GFP Gene.

Mismatched GFP substrate was treated with various concentrations of CEL I in the presence of cocktails of enzymes that together constitute a synthetic mismatch resolution system. The enzymes used were CEL I, T4 DNA polymerase, Taq DNA polymerase and T4 DNA ligase. CEL I activity should nick the heteroduplex 3' of mismatched bases. T4 DNA polymerase contains 3'-5' proofreading activity for excision of the mismatched base from the nicked heteroduplex. T4 DNA polymerase and Taq DNA polymerase contain DNA polymerase capable of filling the gap. T4 DNA ligase seals the nick in the repaired molecule. Taq DNA polymerase also has 5' flap-ase activity.

Matrix experiments were performed to identify the reaction conditions that would serve to resolve mismatches in the GFP heteroduplex substrate. In one experiment, cycle 3/wild-type GFP heteroduplex was incubated in a matrix format with serial dilutions of CEL I fraction number five (described above) at eight different concentrations. Each reaction contained 100 nanograms of heteroduplex substrate and 0.2 microliters of T4 DNA ligase (Gibco BRL) in 1× NEBT4 DNA ligase buffer and dNTPs at 250 micromolar each, in a reaction volume of 10 microliters. In all, the matrix contained 96 individual reactions. One full set of reactions was incubated at room temperature for 30 minutes while another full set was incubated at 37° C. for 30 minutes.

After incubation, PCR was used to amplify the GFP gene from each reaction. Aliquots from each PCR were then digested with HindIII and HpaI and electrophoresed on 3% agarose gels with ethidium bromide. Only cycle 3 GFP has a HindIII site and only wild-type encodes a HpaI site.

If DNA mismatch resolution occurred at either the HindIII or HpaI mismatched sites, then a proportion of the PCR product would be expected to contain both sites, yielding a novel band. The band was observed in all samples, including the negative control samples that had neither CEL I, nor T4 DNA polymerase, nor Taq DNA polymerase. The results suggested that a basal level of background recombination may have occurred at some point in the experiment other than in the GRAMMR reaction; possibly in the PCR step. PCR-mediated recombination is known to occur at some frequency between related sequences during amplification Paabo, et al., J Biol Chem 265(90)4718-4721.

In another experiment, 200 nanograms of cycle 3/wild-type GFP heteroduplex was treated with CEL I and T4 DNA polymerase in various concentrations along with 2.5 units of Taq DNA polymerase in the presence or absence of T4 DNA ligase (0.2 units; Gibco BRL). Each reaction contained 1× NEB T4 DNA ligase buffer with 0.05 mM each DNTP in a final volume of 20 microliters. Reactions were incubated for 30 minutes at 37° C. and 10 microliters were run on a 2% TBE-agarose gel in the presence of ethidium bromide. Results showed that in the presence of DNA ligase, but in the absence of T4 DNA polymerase, increasing amounts of CEL I caused greater degradation of the heteroduplexed DNA, but that this effect could be counteracted by increasing the amount of T4 DNA polymerase in the reaction. These results indicated that the various components of the complete reaction could act together to conserve the integrity of the full-length gene through DNA mismatch resolution.

Another matrix experiment was conducted to expand on these results and to identify additional conditions for DNA mismatch resolution for this synthetic system. 60 nanograms of cycle3/wild-type GFP heteroduplex were treated with CEL I and T4 DNA polymerase at various concentrations in the presence of 2.5 units of Taq DNA polymerase and 0.2 units of T4 DNA ligase in 1× NEB T4 DNA ligase buffer containing 0.5 mM of each dNTP in a reaction volume of 10 microliters. Each set of reactions was incubated for 1 hour at 20° C., 30° C., 37° C., or 45° C. All reactions were then run on a 1.5% TBE-agarose gels in the presence of ethidium bromide. The results showed that the GFP heteroduplex was cleaved into discrete fragments by the CEL I preparation alone. The success of DNA mismatch resolution was initially gauged by the degree to which the apparent full-length integrity of the GFP sequence was maintained by the other components of the mismatch resolution system in the presence of CEL I. Conditions of enzyme concentration and temperature were identified that conserved a high proportion of the DNA as full-length molecules in this assay. Namely, one microliter of the CEL I fraction five preparation (described in Example 1) with one microliter (1 unit) of the T4 DNA polymerase in the presence of the other reaction components which were held constant in the experiment. It was found that as the reaction temperature increased, the degradative activity of CEL I increased accordingly. Furthermore, it was shown that the other components of the repair reaction acted to conserve the integrity of the full-length DNA at 20° C., 30° C., and 37° C., but was remarkably less efficient at conserving the full-length DNA at 45°C. From these results, we concluded that under these experimental conditions, incubation at 45° C. was not optimal for the process of GRAMMR, and that incubation at 20° C., 30° C., and 37° C. were permissible.

EXAMPLE 3

Restoration of Restriction Sitesto GFP Heteroduplex DNA after DNA Mismatch Resolution (GRAMMR)

This experiment teaches the operability of genetic reassortment by DNA mismatch resolution (GRAMMR) by demonstrating the restoration of restriction sites.

The full-length products of a twenty-fold scale-up of the GRAMMR reaction, performed at 37° C. for one hour, using the optimal conditions found above (the 1× reaction contained sixty nanograms of heteroduplex DNA, one microliter of CEL I fraction five (described in Example 1), one unit T4 DNA polymerase in the presence of 2.5 units of Taq DNA polymerase and 0.2 units of T4 DNA ligase in 1× NEB T4 DNA ligase buffer containing 0.5 mM of each DNTP in a reaction volume of 10 microliters) were gel-isolated and subjected to restriction analysis by endonucleases whose recognition sites overlap with mismatches in the GFP heteroduplex, thereby rendering those sites in the DNA resistant to restriction enzyme cleavage. The enzymes used were BamHI, HindIII, HpaI, and XhoI. Negative controls consisted of untreated GFP heteroduplex. Positive controls consisted of Cycle 3 or wild type GFP sequences, individually. All controls were digested with the same enzymes as the product of the DNA mismatch resolution reaction. All samples were run on a 2% TBE-agarose gel in the presence of ethidium bromide.

After treatment with the mismatch resolution cocktail, a proportion of the DNA gained sensitivity to BamHI and XhoI restriction endonucleases, indicating that DNA mismatch resolution had occurred. The HpaI-cut samples could not be interpreted since a low level of cleavage occurred in the negative control. The HindIII, BamHI and XhoI sites displayed different degrees of cleavage in the GRAMMR-treated samples. Restoration of the XhoI site was more extensive than that of the BamHI site, which was in turn, more extensive than restoration at HindIII site.

The extent to which cleavage occurs is indicative of the extent to which mismatches in the DNA have been resolved at that site. Differences in mismatch resolution efficiency may relate to the nature or density of mismatches present at those sites. For example, the XhoI site spans a three-mismatch cluster, whereas the BamHI site spans two mismatches and the HindIII site spans a single mismatch.

EXAMPLE 4

GRAMMR-treated GFP Genes

This example demonstrates that GRAMMR can reassort sequence variation between two gene sequences in a heteroduplex and that there are no significant differences in GRAMMR products that were directly cloned, or PCR amplified prior to cloning.

The GRAMMR-treated DNA molecules of Example 3 were subsequently either directly cloned by ligation into pCR-Blunt II-TOPO (Invitrogen), or amplified by PCR and ligated into pCR-Blunt II-TOPO according to the manufacturer's instructions, followed by transformation into *E. coli*. After picking individual colonies and growing in liquid culture, DNA was prepared and the sequences of the GFP inserts were determined. As negative controls, the untreated GFP heteroduplex substrate was either directly cloned or PCR amplified prior to cloning into the plasmid.

In GRAMMR, reassortment of sequence information results from a process of information transfer from one strand to the other. These sites of information transfer are analogous to crossover events that occur in recombination-based DNA shuffling methods. For the purposes of relating the results of these reassortment experiments, however, the GRAMMR output sequences are described in terms of crossovers. Sequences of twenty full-length GFP clones that were derived from the GRAMMR-treated GFP genes were analyzed. Four of these clones were derived from DNA that had been directly cloned into pZeroBlunt (Invitrogen) following GRAMMR reaction (no PCR amplification). The other sixteen sequences were cloned after PCR amplification. Analysis of these full-length GFP sequences revealed that all twenty sequences had undergone sequence reassortment having between one and ten crossovers per gene. A total of 99 crossovers were found in this set of genes, giving an average of about 5 crossovers per gene. With the distance between the first and last mismatches of about 590 nucleotides, an overall frequency of roughly one crossover per 120 base-pairs was calculated. Within this set of twenty clones, a total of seven point mutations had occurred within the sequences situated between the PCR primer sequences, yielding a mutation frequency of roughly 0.05%.

Thirty-five clones that had not been subjected to the GRAMMR reaction were sequenced. Of these controls, fourteen were derived from direct cloning and twenty-one were obtained after PCR amplification using the GFP heteroduplex as template. Of these thirty-five non-GRAMMR treated control clones, eight were recombinants, ranging from one to three crossovers, with most being single crossover events. A total of twenty-five point mutations had occurred within the sequences situated between the PCR primers, yielding a mutation frequency of roughly 0.1%.

No significant differences were observed between the GRAMMR-treated products that were either directly cloned or PCR amplified. Notably, though, in the non-GRAMMR-treated controls, the frequency of recombinants was higher in the PCR amplified DNAs than in the directly cloned DNAs. This higher frequency is consistent with results obtained by others in which a certain level of recombination was found to be caused by "jumping PCR." (Paabo, et al., DNA damage promotes jumping between templates during enzymatic amplification. J Biol Chem 265(90)4718-4721).

EXAMPLE 5

Heteroduplex Substrate Preparation for Plasmid-on-Plasmid Genetic Reassortment By DNA Mismatch Resolution (POP GRAMMR) of GFP Plasmids This example teaches that heteroduplex substrate for Genetic Reassortment by DNA Mismatch Resolution can be in the form of intact circular plasmids. Cycle 3-GFP and wild-type GFP heteroduplex molecules were prepared plasmid-on-plasmid (POP) format. In this format, the GFP sequences were reasserted within the context of a circular double-stranded plasmid vector backbone. This made possible the recovery of the reasserted product by direct transformation of *E. coli* using an aliquot of the GRAMMR reaction. Consequently, neither PCR amplification nor other additional manipulation of the GRAMMR-treated DNA was necessary to obtain reasserted clones.

Mismatched DNA substrate for POP-GRAMMR reactions was generated containing wild-type GFP (SEQ ID NO: 29) and Cycle 3 GFP (SEQ ID NO: 30), resulting in the two pBluescript-based plasmids, pBSWTGFβ (SEQ ID NO: 31) and pBSC3GFP (SEQ ID NO: 17), respectively. The GFPs were inserted between the KpnI and EcoRI sites of the pBluescript polylinker so that the only sequence differences between the two plasmids occurred at sites where the wild-type and Cycle 3 GFPs differ from one-another. Both plasmids were linearized by digestion of the plasmid backbone with SapI, cleaned up using a DNA spin-column, mixed, amended to 1× PCR buffer (Barnes, 1994; *PNAS,* 91, 2216-2220), heated in a boiling water bath for three minutes, and slow-cooled to room temperature to anneal the denatured DNA strands. Denaturing and annealing these DNAs led to a mixture of duplexes; the re-formation of parental duplexes, and the formation of heteroduplexes from the annealing of strands from each of the two input plasmids. Parental duplexes were deemed undesirable for GRAMMR and were removed by digestion with restriction enzymes that cut in one or the other parental duplex but not in the heteroduplexed molecules. PmlI and XhoI were chosen for this operation since PmlI cuts only in the wild-type GFP sequence and XhoI cuts only Cycle 3 GFP. After treatment with these enzymes, the products were resolved on an agarose gel. The full-length, uncut heteroduplex molecules were resolved from the PmlI- and XhoI-cut parental homoduplexes in an agarose gel and purified by excision of the band and purification with a DNA spin column.

The resulting population of heteroduplexed molecules was treated with DNA ligase to convert the linear DNA into circular, double-stranded DNA heteroduplexes. After confirmation by agarose gel-shift analysis, the circular double-stranded GFP heteroduplexed plasmid was used as substrate for GRAMMR reactions. Examples of the resulting clones are included as SEQ ID NO: 5, SEQ ID NO: 6, SEQ ID NO: 7, and SEQ ID NO: 8.

EXAMPLE 6

Exemplary Reaction Parameters for Genetic Reassortment by DNA Mismatch Resoluton

CEL I and T4 DNA Polymerase Concentrations Compared

The GRAMMR reaction involves the interaction of numerous enzymatic activities. Several parameters associated with the GRAMMR reaction were examined, such as CEL I concentration, T4 DNA polymerase concentration, reaction temperature, substitution of T4 DNA polymerase with T7 DNA polymerase, the presence of Taq DNA polymerase, and the source of the CEL I enzyme. A matrix of three different CEL I concentrations versus two concentrations of T4 DNA polymerase was set up to examine the limits of the in vitro DNA mismatch resolution reaction.

Twenty-one nanograms (21 ng) of the circular double-stranded heteroduplexed plasmid, prepared as described in example 5, was used as substrate in a series of ten microliter reactions containing 1× NEB ligase buffer, 0.5 mM each dNTP, 1.0 unit Taq DNA polymerase, 0.2 units T4 DNA ligase (Gibco/BRL), either 1.0 or 0.2 units T4 DNA polymerase, and either 0.3, 0.1, or 0.03 microliters of a CEL I preparation (fraction 5, described in Example 1). Six reactions representing all six combinations of the two T4 DNA polymerase concentrations with the three CEL I concentrations were prepared, split into equivalent sets of five microliters, and incubated at either 20 degrees C. or 37 degrees C. A control reaction containing no CEL I and 0.2 unit of T4 DNA polymerase with the other reaction components was prepared and incubated at 37 degrees C. After 30 minutes, one microliter aliquots of each reaction were transformed into competent DH5-alpha *E. coli* which were then plated on LB amp plates. Colonies were picked and cultured. Plasmid DNA was extracted and examined by restriction fragment length polymorphism analysis (RFLP) followed by sequence analysis of the GFP gene sequences. RFLP analysis was based on differences in several restriction enzyme recognition sites between the wild-type and Cycle 3 GFP genes. The RFLP results showed that throughout the CEL I/T4 DNA polymerase/temperature matrix, reassortment of restriction sites, that is GRAMMR, had occurred, and that no such reassortment had occurred in the zero CEL I control clones. DNA sequence analysis confirmed that reassortment had occurred in all of the CEL 1-containing samples. Sequencing also confirmed that the zero-CEL I controls were not reasserted, with the exception of a single clone of the 16 control clones, which had a single-base change from one gene sequence to the other, presumably resulting either from repair in *E. coli* or from random mutation. The sequences of several exemplary GRAMMR-output GFP clones are shown; all of which came from the reaction containing 0.3 microliters of the CEL I preparation and 1.0 unit of T4 DNA polymerase incubated at 37 degrees C. The parental wild-type and Cycle 3 GFP genes are shown first for reference.

EXAMPLE 7

Taq DNA Polymerase is Not Required for Genetic Reassortment by DNA Mismatch Resolution This experiment teaches that Taq DNA Polymerase does not dramatically, if at all, contribute or interfere with the functioning of GRAMMR. Taq DNA polymerase is reported to have a 5' flap-ase activity, and had been included in the teachings of the previous examples as a safeguard against the possible formation and persistence of undesirable 5' flaps in the heteroduplexed DNA undergoing the GRAMMR reaction.

GRAMMR reactions were set up, as in Example 6, with twenty-one nanograms of the circular double-stranded heteroduplexed GFP plasmid substrate in ten microliter reactions containing 1× NEB ligase buffer, 0.5 mM each dNTP, 0.2 units T4 DNA ligase, 1.0 unit T4 DNA polymerase, 1.0 microliter of a CEL I preparation (fraction 5, described in Example 1), and either 2.5 units, 0.5 units of Taq DNA polymerase, or no Taq DNA polymerase. After 30 minutes, one microliter aliquots of each reaction were transformed into competent DH5-alpha *E. coli* which were then plated on LB amp plates. Colonies were picked and cultured. Plasmid DNA was extracted and examined by RFLP analysis followed by sequence analysis of the GFP gene sequences. The RFLP results showed that reassortment of restriction sites, that is, GRAMMR, had occurred both in the presence and the absence of Taq DNA polymerase in the GRAMMR reaction. DNA sequence analysis confirmed these results. Therefore, the data shows that Taq DNA polymerase was unnecessary for GRAMMR.

EXAMPLE 8

Alternate Proofreading DNA Polymerases for Genetic Reassortment by DNA Mismatch Resolution This experiment teaches that Genetic Reassortment by DNA Mismatch Resolution is not limited to the use of T4 DNA polymerase, and that alternate DNA polymerases can be substituted for it.

Reactions were set up, as in Example 6, with twenty-one nanograms of the circular double-stranded heteroduplexed GFP plasmid substrate in ten microliter reactions containing 1× NEB ligase buffer, 0.5 mM each dNTP, 0.2 units T4 DNA ligase (Gibco/BRL), 10 units or 2 units of T7 DNA polymerase, 1.0 microliter of a CEL I preparation (fraction 5, described in Example 1), and 2.5 units of Taq DNA polymerase. After 30 minutes, one microliter aliquots of each reaction were transformed into competent DH5-alpha *E. coli* which were then plated on LB amp plates. Colonies were picked and cultured. Plasmid DNA was extracted and examined by RFLP analysis followed by sequence analysis of the GFP gene sequences. The RFLP results showed that reassortment of restriction sites, that is GRAMMR, had occurred in both T7 DNA polymerase-containing reactions. DNA sequence analysis confirmed these results. Therefore, the data shows that T7 DNA polymerase can substitute for T4 DNA polymerase for GRAMMR. In addition, it shows that individual components and functionalities can be broadly substituted in GRAMMR, while still obtaining similar results.

EXAMPLE 9

Use of Cloned CEL I in the GRAMMR Reaction

This example teaches that CEL I from a cloned source can be used in place of native CEL I enzyme purified from celery in Genetic Reassortment By DNA Mismatch Resolution without any noticeable change in results.

The cDNA of CEL I was cloned from celery RNA. The gene was inserted into a TMV viral vector and expressed. Transcripts of the construct were used to infect *Nicotiana benthamiana* plants. Infected tissue was harvested, and the CEL I enzyme was purified. The results of the GRAMMR reaction obtained using the purified enzyme were compared to those using CEL I purified from celery, and were found to be similar.

Reactions were set up using twenty-one nanograms of the circular double-stranded heteroduplexed GFP plasmid substrate, as described in Example 5, in ten microliters containing 1× NEB ligase buffer, 0.5 mM each dNTP, 0.2 units T4 DNA ligase (Gibco/BRL), 1 unit of T4 DNA polymerase, and either 1.0 microliter of CEL I purified from celery (fraction 5, described in Example 1), or 0.3 microliters of CEL I purified from a cloned source. After 30 minutes, one microliter aliquots of each reaction were transformed into competent DH5-alpha *E. coli* which were then plated on LB amp plates. Colonies were picked and cultured. Plasmid DNA was extracted and examined by RFLP analysis followed by sequence analysis of the GFP gene sequences. The RFLP results showed that reassortment of restriction sites, that is, GRAMMR had occurred in both celery-derived CEL I, as well as cloned CEL I-containing reactions. DNA sequence analysis confirmed these results. Therefore, the data shows CEL I from a cloned source can be used in lieu of CEL I from celery for GRAMMR. In addition, the data demonstrates that it is CEL I activity that is part of the GRAMMR reaction, rather than a coincidental effect resulting from the purifying steps used in extracting CEL I from celery.

EXAMPLE 10

Molecular Breeding of Tobamovirus 30K Genes in a Viral Vector

In the preceding examples, Genetic Reassortment by DNA Mismatch Resolution has been taught to be useful for reasserting sequences that are highly homologous, for example, wtGFP and Cycle 3 GFP are 96% identical. The present example teaches that GRAMMR can be used to reassort more divergent nucleic acid sequences, such as genes encoding tobamovirus movement protein genes.

Heteroduplexes of two tobamovirus movement protein (MP) genes that are approximately 75% identical were generated. The heteroduplex substrate was prepared by annealing partially-complementary single-stranded DNAs of opposite strandedness synthesized by asymmetric PCR; one strand encoding the movement protein gene from the tobacco mosaic virus U1 type strain (TMV-U1) (SEQ ID NO: 9), and the other strand encoding the movement protein gene from tomato mosaic virus (TOMV) (SEQ ID NO: 10). The sequences of the two partially complementary movement protein genes were flanked by 33 nucleotides of absolute complementarity to promote annealing of the DNAs at their termini and to facilitate PCR amplification and cloning. The annealing reaction took place by mixing 2.5 micrograms of each single-stranded DNA in a 150 microliter reaction containing 333 mM NaCl, 33 mM $MgCl_2$, 3.3 mM dithiothreitol, 166 mM Tris-HCl, pH 7, and incubating at 95° C. for one minute followed by slow cooling to room-temperature. GRAMMR was performed by incubating 5 microliters of the heteroduplex substrate in a 20 microliter reaction containing 1× NEB ligase buffer, 0.5 mM each dNTP, 0.4 units T4 DNA ligase (Gibco/BRL), 2.0 units of T4 DNA polymerase, and CEL I. The CEL I was from a cloned preparation and the amount that was used varied from 2 microliters of the prep, followed by five serial 3-fold dilutions. A seventh preparation with no CEL I was prepared, which served as a control.

After one hour at room-temperature, DNA was purified from the reactions using Strataprep spin DNA purification columns (Stratagene, LaJolla, Calif.) and used as templates for PCR reactions using primers designed to anneal to the flanking primer-binding sites of the two sequences. PCR products from each reaction were purified using Strataprep columns, digested with AvrII and PacI, and ligated into the movement protein slot of similarly-cut pGENEWARE®-MP-Avr-Pac. This plasmid contained a full-length infectious tobamovirus-GFP clone modified with AvrII and PacI sites flanking the movement protein gene to permit its replacement by other movement protein genes. After transformation of DH5-alpha *E. coli* and plating, colonies were picked, cultures grown, and DNA was extracted. The movement protein inserts were subjected to DNA sequence analysis from both directions and the sequence data confirmed that in the majority of inserts derived from the GRAMMR-treated material were reasserted sequences made up of both TMV-U1 and ToMV movement protein gene sequences. The DNA sequences of several exemplary GRAMMR output MP clones are shown as SEQ ID NO: 11, SEQ ID NO: 12, SEQ ID NO: 13, SEQ ID NO: 14, and SEQ ID NO: 15.

EXAMPLE 11

GRAMMR to Generate Improved Arsenate Detoxifying Bacteria

Arsenic detoxification is important for mining of arsenopyrite-containing gold ores and other uses, such as environmental remediation. Plasmid pGJ103, containing an arsenate detoxification operon (Ji and Silver, 1992)(Ji, G. and Silver, S., Regulation and expression of the arsenic resistance operon from *Staphylococcus aureus* plasmid pI258, J. Bacteriol. 174, 3684-3694 (1992), incorporated herein by reference), is obtained from Prof. Simon Silver (U. of Illinois, Chicago, Ill.). *E. coli* TG1 containing pGJ103, containing the pI258 ars operon cloned into pUC19, has a MIC (minimum inhibitory concentration) of 4 μg/ml on LB ampicillin agar plates. The ars operon is amplified by mutagenic PCR, cloned into pUC19, and transformed into *E. coli* TG1. Transformed cells are plated on a range of sodium arsenate concentrations (2, 4, 8, 16 mM). Colonies from the plates with the highest arsenate levels are picked. The colonies are grown in a mixed culture with appropriate arsenate selection. Plasmid DNA is isolated from the culture. The plasmid DNA is linearized by digestion with a restriction endonuclease that cuts once into the pUC19 plasmid backbone. The linearized plasmids are denatured by heating 10 min. at 94° C. The reaction is allowed to cool to promote annealing of the single strands. Partially complementary strands that hybridize have non-base paired nucleotides at the sites of the mismatches. Treatment with CEL I (purified by the method of Example 9) causes nicking of one or the other polynucleotide strand 3' of each mismatch. The presence of a polymerase containing a proofreading activity, such as T4 DNA polymerase allows excision of the mismatch, and subsequent 5'-to-3' polymerase activity fills in the gap using the other strand as a template. T4 DNA ligase then seals the nick by restoring the phosphate backbone of the repaired strand. The result is a randomization of mutations among input strands to give output strands with potentially improved properties. These output polynucleotides are transformed directly into *E. coli* TG1 and the cells are plated at higher arsenate levels; 8, 16, 32, 64 mM. Colonies are picked from the plates with the highest arsenate levels and another round of reassortment is performed as above except that resulting transformed cells are plated at 32, 64, 128, 256 mM arsenate. The process can then be repeated one or more times with the selected clones in an attempt to obtain additional improvements.

EXAMPLE 12

Cloning, Expression and Purification of CEL I Endonuclease

This example teaches the preparation of nucleic acid molecules that were used for expressing CEL I endonuclease from plants, identified herein as, p1177 MP4-CEL I Avr (SEQ ID NO: 1), and p1177 MP4-CEL I 6HIS (SEQ ID NO: 2). In particular, this example refers to disclosures taught in U.S. Pat. Nos. 5,316,931, 5,589,367, 5,866,785, and 5,889,190, incorporated herein by reference.

Celery RNA Extraction:

Celery was purchased from a local market. Small amounts of celery tissue (0.5 to 0.75 grams) were chopped, frozen in liquid nitrogen, and ground in a mortar and pestle in the presence of crushed glass. After addition of 400 microliters of Trizol and further grinding, 700 microliters of the extract were removed and kept on ice for five minutes. Two hundred microliters of chloroform were then added and the samples were centrifuged, left at room temperature for three minutes, and re-centrifuged at 15,000 g for 10 minutes. The aqueous layer was removed to a new tube and an equal volume of isopropanol was added. Tubes were inverted to mix and left at room temperature for 10 minutes followed by centrifugation at 15,000 g for ten minutes at 4° C. The pellet was washed twice in 400 microliters of 70% ethanol, once in 100% ethanol, air dried, and resuspended in 40 microliters of distilled water. One microliter of RNasin was added and 3.5 microliters was run on a 1% agarose gel to check the quality of the RNA prep (Gel picture). The remainder was stored at −70° C. until further use.

CEL I Gene Cloning and Expression by a Viral Vector:

The total RNA from celery was subjected to reverse transcription followed by PCR to amplify the cDNA encoding the CEL I gene sequence. In separate reactions, eleven microliters of the total celery RNA prep was mixed with one microliter (50 picomoles) of either CelI-Avr-R, CelI-6H-R, or with two microliters of oligo dT primer. CelI-Avr-R was used to prime cDNA and amplify the native CEL I sequence at the 3' end of the gene, while CelI-6H-R was used to add a sequence encoding linker peptide and a 6-His tag to the 3' terminus of the CEL I gene. The samples were heated to 70° C. for one minute and quick-chilled on ice prior to the addition of 4 microliters of 5× Superscript II buffer, two microliters of 0.1M DTT, 1 microliter of 10 mM each dNTP, and 1 microliter of Superscript II (Gibco/BRL) to each reaction. The reactions were incubated at 42° C. for one hour.

PCR amplification of the CEL I cDNA sequence was performed using the method of W. M. Barnes (*Proc Natl Acad. Sci*. USA, 1994 Mar. 15;91(6):2216-20) with a Taq-Pfu mixture or with Pfu alone. The RT reaction primed with CelI- Avr-R was used as template for a PCR using primers CelI-Pac-F (as the forward primer) paired with CelI-Avr-R (as the reverse primer). In other PCRs, the RT reaction that was primed with oligo dT was used as template for both of the above primer pairs. All PCR reactions were performed in 100 microliters with 30 cycles of annealing at 50° C. and two minutes of extension at 72° C. Aliquots of the resulting reactions were analyzed by agarose gel electrophoresis. Reactions in which Pfu was used as the sole polymerase showed no product. All reactions performed with the Taq/Pfu mixtures yielded product of the expected size. However, those amplified from cDNA primed with Cel I specific primer pairs gave more product than reactions amplified from cDNA primed with oligo-dT. DNAs from the PCR reactions that gave the most product were purified using a Zymoclean DNA spin column kit and digested with PacI and AvrII, gel-isolated, and ligated into PacI and AvrII-digested plasmid pRT130, a tobamovirus-based GENEWARE® vector. 2 microliters of each ligation were transformed into DH5α competent *E. coli* and cultured overnight on LB-amp agar plates. Colonies were picked and grown overnight in liquid culture, and plasmid DNA was isolated using a Qiagen plasmid prep kit. 12 clones from each construct were screened by digestion with PacI and AvrII and 11 of 12 of each set were positive for insert of the correct size. Ten of the clones for each construct were transcribed in-vitro and RNA was inoculated to *N. benthamiana* plants. In addition, the CEL I gene inserts in both sets of ten clones were subjected to sequence analysis. Several clones containing inserts encoding the native form of CEL I had sequence identical to the published CEL I sequence in WO 01/62974 A1. One clone containing an insert encoding CEL I fused to a 6-Histidine sequence was identical to the published CEL I sequence. One clone of each (pRT130-CEL I Avr-B3 and pRT130-CEL 6His-A9, respectively) was selected for further work. The CEL I-encoding sequences in these clones were subsequently transferred to another GENEWARE® vector. The sequences of these clones, p1177 MP4-CEL I Avr-B3, and p1177 MP4-CEL I 6His-A9 are provided as SEQ ID NO: 1 and SEQ ID NO: 2, respectively.

Assay of Cloned CEL I Activities:

To determine whether the GENEWARE® constructs containing Cel I sequences could produce active CEL I enzyme, samples of pRT130-CEL I Avr (SEQ ID NO: 1) and pRT130-CEL I 6His (SEQ ID NO: 2), and GFP-GENEWARE control-infected plants were harvested and homogenized in a small mortar and pestle in Tris-HCl at pH 8.0. Extracts were clarified and assayed for supercoiled DNA nicking activity. Each supercoiled DNA nicking assay was performed in a reaction containing 0.5 micrograms of a supercoiled plasmid prep of a pUC19-derivative in 1× NEB ligase buffer in a total volume of 10 microliters. The amounts of plant extract added to the reactions were 0.1 microliter, 0.01 microliter, or 0.001 microliter, incubated at 42° C. for 30 minutes, and run on a 1% TBE-agarose gel in the presence of ethidium bromide. Little or no nicking activity was detected in the GFP-GENEWARE control-infected plant extract whereas extracts from plants infected with the CEL I-GENEWARE constructs showed appreciable amounts of activity against the plasmid DNA substrate.

Additional activity assays were performed on extracts of plants inoculated with pRT130-CEL I Avr-B3 and pRT130-CEL I 6His-A9. In these assays, intracellular fluid was washed from infected leaves and assayed separately from material obtained from the remaining washed leaf tissues. Assays were performed as described above with the exception that the incubation was at 37° C. for one hour. Samples were run on a 1% TBE-agarose gel in the presence of ethidium bromide and photographed.

Purification of 6His-Tagged CEL I from Infected *N. benthamiana* Plants:

*N. benthamiana* plants were inoculated with RNA transcripts from pRT130-CEL I 6His-A9 at 20-21 days post-sowing. Tissues were harvested from 96 infected plants at 10 days post-inoculation and subjected to intracellular fluid washes. Briefly, infected leaf and stem material was vacuum infiltrated for 30 seconds twice with chilled infiltration buffer (50 mM phosphate pH 4 in the presence of 7 mM β-ME). Infiltrated tissues were blotted to adsorb excess buffer and secreted proteins were recovered by centrifugation at 2500× g for 20 min using basket rotor (Beckman). PMSF was added to the extracted intracellular fluid (IF) containing recombinant CEL_I to a final concentration of 1 mM, and incubated at 25° C. for 15 min with stirring. After addition of Imidazole (pH 6.0) and NaCl to the extract to the final concentration of 5 mM and 0.5 M respectively, IF was adjusted to pH 5.2 and filtered through 1.2μ Sartorius GF membrane (Whatman) to remove most of the Rubisco and green pigments. Immediately after clarification, pH was adjusted to 7.0 using concentrated NaOH solution and incubated on ice for 20 min to allow non-proteinaceous material to precipitate. IF was further clarified using 0.8μ or 0.65/0.45μ Sartorius GF (Whatman). Recombinant CEL I was purified from the clarified IF by metal chelating affinity chromatography using $Ni^{2+}$ Fast Flow Sepharose (Amersham Pharmacia Biotech, New Jersey) equilibrated with binding buffer (50 mM phosphate, 0.5 M NaCl; pH 7.0) containing 5 mM imidazole, with a linear velocity of 300 cm/hr. Unbound protein was washed with 20 mM imidazole/binding buffer, and CEL I was eluted from $Ni^{2+}$ Sepharose with a linear gradient of 20 to 400 M imidazole in the binding buffer. Fractions still containing imidazole were assayed for supercoiled DNA nicking activity as described above but were found to have negligible activity. The same fractions were then dialyzed against 0.1 M Tris-HCl, pH 8.0 in the presence of $ZnCl_2$ using 10 kD MWCOF dialysis tubing (Pierce) and assayed again. The supercoiled DNA nicking activity was restored after this dialysis.

IF and purified CEL-I protein were analyzed using Sodium Dodecyl Sulfate Polyacrylamide Gel Electrophoresis (SDS-PAGE) precast Tris-glycine gels (Invitrogen, Carlbad, Calif.) in the buffer system of Laemmli with a Xcell II Mini-Cell apparatus (Invitrogen, Carlsbad, Calif.). The protein bands were visualized by Coomassie brilliant blue and by silver staining. SDS-PAGE Gels were scanned and analyzed using Bio-Rad gel imager.

Mass Spectrometry of Purified CEL I:

The average molecular mass of the purified CEL I was determined by matrix-assisted laser/desorption ionization time-of-flight mass spectrometry (MALDI-TOF). An aliquot of CEL I was diluted 1:10 with 50% acetonitrile/water and mixed with sinapinic acid matrix (1:1 v/v) using a PE Biosystem DE-Pro mass spectrometer. The mass spectrometry was performed using an accelerating voltage of 25 kV and in the positive-linear ion mode.

Mass Spectrometry of Peptides Isolated from Purified CEL I:

CEL I was separated on SDS-PAGE on a 14% gel and stained with Coomassie brilliant blue. A single homogenous band was visible. This band was excised and de-stained completely. Protein was reduced in the presence of 10 mM DDT in 50% acetonitrile for 30 min at 37° C. and reduced sulfhydro groups were blocked in the presence of 28 mM iodoacetamide in 50% acetonitrile for 30 min at 24° C. in absence of light.

Gel pieces were washed with 50% acetonitrile and after partial dehydration, the excised CEL I band was macerated in a solution of high purity trypsin (Promega). The proteolytic digestion was allowed to continue at 37° C. for 16 h. The resulting peptides were eluted from gel pieces with a 50% acetonitrile and 0.1% tri-fluoro-acetic acid (TFA) concentrated in a SpeedVac. The peptides were analyzed by MALDI-TOF. Mixed tryptic digests were crystallized in a matrix of α-cyano-4-hydroxycinnamic acid and analyzed by using a PerSeptive Biosystem DE-STR MALDI-TOF mass spectrometer equipped with delayed extraction operated in the reflector-positive ion mode and accelerating voltage of 20 kV. Expected theoretical masses were calculated by MS-digest (Protein Prospector) or GPMAW program (Lighthouse Data, Odense, Denmark). For tandem mass spectrometry (nano electrospray ionization (ESI), peptide samples were diluted with 5% acetonitrile/0.1% formic acid and subjected to LC MS/MS, analyzed on a quadropole orthogonal time-of-flight mass spectrometry instrument (micromass, inc., Manchester, UK). The data were processed by Mslynx and database was searched by Sonar.

Virally expressed, recombinant CEL I was secreted to the IF. Clarified IF-extracted material was used to purify the His-tag CEL I activity. CEL I was purified using one step $Ni^{2+}$ affinity chromatography separation. A highly purified homogeneous single protein band was purified as determined by Coomassie stained SDS-PAGE and mass spectrometry. The size of mature proteins and percent glycosylation concur with what has been reported for the CEL I protein isolated from celery (Yang et al., 2000). The purified CEL I has an average molecular mass of 40 kD as determined by MALDI-TOF mass spectrometry, indicates 23.5% glycosylation by mass. CEL I has four potential glycosylation cites at amino acid positions 58, 116, 134, and 208. A mono-isotopic mass of 2152.6086 (2152.0068 Theoretical) Da corresponding to the mass of the peptide 107-125 (K)DMCVAGAIQN-FTSQLGHFR(H) (SEQ ID NO: 35) that was recovered by MALDI-TOF, indicates that asparagine 116 is not glycosylated. Together, these gel analyses and mass spectrometry data indicate that a significant fraction of the CEL I protein was recoverable, and that the protein was correctly processed in the *N. benthamiana* plant.

For subsequent experiments, the 6-His tagged CEL I gene was produced using p1177 MP4-CEL I 6His-A9. This clone was transcribed and inoculated onto *N. benthamiana* plants, which were harvested 8 days post infection. The plant material was combined with 2 volumes of extraction buffer (500 mM NaCl, 100 mM NaPi, 25 mM Tris pH 8.0, 7 mM Beta-mercaptoethanol, 2 mM PMSF) and vacuum infiltrated. Following buffer infiltration the tissue was macerated in a juice extractor, the resulting green juice adjusted to 4% w/v polyethyleneglycol, and let stand at 4° C. for one hour. The green juice was clarified by either centrifugation at low speed (3500× g) for 20 minutes or combined with perlite (2% w/v) and filtered through a 1.2 μm filter. The tagged CEL I can be selectively purified from the clarified green juice by metal affinity chromatography. The green juice was either combined with nickel-NTA resin, and batch binding of the CEL I performed, or purification was performed in column format, where the green juice was permitted to flow through a bed of nickel-NTA resin. For binding, the clarified green juice was adjusted to 10% w/v glycerol and 10 mM imidazole. Following binding the resin was washed extensively with wash buffer (330 mM NaCl, 100 mM NaPi, pH 8.0, 10 mM imidazole) and the bound CEL I enzyme eluted from the nickel-NTA resin in 2 resin-bed volumes of 1× phosphate-buffered saline (PBS) containing 400 mM imidazole. The CEL I preparation was subsequently dialyzed against 1×

PBS to remove the imidazole, assayed for activity, and stored at 4° C. or at −20° C. with or without glycerol until use.

EXAMPLE 13

Cloning, Expression and Use of Res I Endonuclease

This example teaches the construction of a cDNA library from *Selaginella lepidophylla*, the identification of a nucleic acid sequence from the library that encodes an endonuclease, and the expression of the new endonuclease, herein designated as "RES I."

RNA was extracted from tissues of the resurrection plant, *Selaginella lepidophylla*, using the Trizol method, and oligo-dT primed cDNA that was prepared using standand methodology. Resulting cDNAs were ligated into a GENEWARE®-based cloning vector and the ligation products were transformed into competent *E. coli* cells. Bacterial colonies containing GENEWARE® cDNA clones were picked at random and grown as liquid cultures prior to DNA prepping and determination of the cloned cDNA sequences. The sequence files for the cloned Selaginella cDNAs were loaded into a database which was then searched by BLAST analysis for sequences that had similarity to the DNA sequence of the CEL I gene. BLAST analysis was also performed on other DNA sequence databases containing sequences of cDNAs obtained from other species.

BLAST hits that showed some level of homology to the celery CEL I sequence were identified in libraries from several species and the corresponding GENEWARE®-cDNA clones were re-arrayed into a single set of GENEWARE®-cDNA clones. This set of cDNA clones was then transcribed in vitro to generate infectious GENEWARE® transcripts which were then inoculated onto leaves on *Nicotiana benthamiana* plants for expression analysis of the cDNA sequences encoded within the GENEWARE® viral genome. At seven days post-inoculation, leaf samples were taken from the infected plants and homogenized in two volumes of water. The extracts were then assayed for supercoiled DNA nicking and cleavage activity.

Each supercoiled DNA nicking assay was performed in a reaction containing 0.5 micrograms of a supercoiled plasmid prep of a pUC19-derivative in 1× NEB T4 DNA ligase buffer in a total volume of 10 microliters. The amounts of plant extract added to the reactions were 1 microliter, 0.33 microliter, or 0.011 microliter, incubated at 37° C. for 30 minutes, and run on a 1% TAE-agarose gel in the presence of Gelstar fluorescent DNA staining reagent. Little or no nicking activity was detected in uninfected plant extracts whereas only extracts from plants infected with GENEWARE® constructs containing cDNAs for a single gene from *Selaginella lepidophylla* showed appreciable amounts of activity against the plasmid DNA substrate.

The complete gene sequences of these clones were determined and PCR primers were designed to amplify the open reading frame minus any non-coding 5' and 3' sequences and to add a six histidine tail to the C-terminus of the encoded protein. The primers were then used to amplify the ORF from one of the active full-length *Selaginella* clones. The resulting PCR product was then cloned into the GENEWARE® vector pDN4 between the PacI and AvrII sites for expression in planta. The resulting clone, pLSB2225, which contains the RES I ORF (SEQ ID NO: 16), and which encodes the RES1 protein (SEQ ID NO: 34), was sequenced to confirm that the gene had been inserted correctly, and then transcribed in vitro followed by inoculation of the infectious transcripts onto *N. benthamiana* plants. Seven days post inoculation, infected plant extracts were made as above and assayed for supercoiled DNA nicking and digestion activity to confirm the activity of the cloned enzyme.

Each supercoiled DNA nicking assay was performed in a reaction containing 0.5 micrograms of a supercoiled plasmid prep of a pUC19-derivative in 1× NEB *E. coli* DNA ligase buffer in the presence of 50 mM KCl in a total volume of 10 microliters. The amounts of plant extract added to the reactions were 0.2 microliter, 0.04 microliter, 0.008 microliter, or 0.0016 microliter, incubated at 37° C. for 30 minutes, and run on a 0.8% TAE-agarose gel in the presence of Gelstar fluorescent DNA staining reagent. Little or no nicking activity was detected in uninfected plant extracts whereas extracts from plants infected with the GENEWARE®-*Selaginella* construct pLSB2225 showed appreciable amounts of activity against the plasmid DNA substrate.

After positive results were obtained in that assay, extracts of pLSB2225 infected plants were used in a GRAMMR reaction to test the ability of this enzyme to operate as a component of the mismatch resolution reaction in place of the GENEWARE®-produced CEL I enzyme.

EXAMPLE 14

Use of RES I in the GRAMMR Reaction

This example teaches that RES I can be used in place of native CEL I enzyme purified from celery in Genetic Reassortment By DNA Mismatch Resolution without any noticeable change in results.

GRAMMR was performed between the wild-type *Aequorea victoria* GFP gene (Prasher, et al., Gene111(92)229) in a pBS derivative (Stratagene, La Jolla, Calif.) encoded by pBSWTGFβ (SEQ ID NO:31) and a variant with mutations to increase fluorescence intensity in *E. coli*, and to alter the emission wavelength to blue light emission (Crameri, et al., Nat Biotechnol 14(96)315; Heim et al., PNAS91(94)12501; Yang, et al., J Biol Chem 273(98)8212). This variant gene, encoded by the plasmid pBSC3BFP, as shown in FIG. 5 (SEQ ID NO: 32), encodes a fluorescent protein that emits bright blue light when excited by longwave UV light.

The GRAMMR reactions were performed on GFP/c3BFP heteroduplexes in a circular, double-stranded plasmid DNA context. The circular, whole-plasmid heteroduplex DNA substrates were prepared by first linearizing pBSWTGFP (SEQ ID NO:31) and pBSC3BFP (FIG. 5, SEQ ID NO: 32) by digestion with Kpn I and NgoM IV, respectively, then purifying the digested DNA using DNA spin columns. Next, 200 nanograms of each of the two linearized plasmids were mixed and brought to 1× SSPE (180 nM NaCl, 10 mM $NaH_2PO_4$, 1 mM EDTA at pH 7.4) in a volume of 20 microliters. The mixture was then incubated at 95 degrees Celsius for 4 minutes, plunged into icewater where it remained for 10 minutes prior to incubation at 37 degrees Celsius. After 30 minutes, the annealed DNA sample was then transferred back to ice where it was held until use in GRAMMR reactions.

Two independent series of shuffling reactions were performed to compare CEL I with RES I in their abilities to facilitate sequence shuffling by GRAMMR. Each GRAMMR reaction contained 1 unit of T4 DNA polymerase, 2 units of *E. coli* DNA ligase, and 5 nanomoles of each dNTP in 1× NEB *E. coli* ligase buffer supplemented with KCl to 50 mM. Two separate enzyme dilution series were then performed. To each of two series of tubes containing aliquots of the above cocktail, one microliter aliquots of GENEWARE®-expressed CEL I or RES I extracts at dilutions of ⅓, ⅑, 1/27, 1/81, or 1/243 were added. An endonuclease-free control reaction was also prepared. To each of the reactions, one microliter aliquots containing 20 nanograms of the annealed DNA heteroduplex substrate were added and the reactions incubated at room temperature for one hour and on ice for 30 minutes prior to transformation into competent *E. coli.*

Green fluorescent protein (GFP) and blue fluorescent protein (BFP) could be visualized in the resulting colonies by long wave UV illumination. The parental wild-type GFP has dim green fluorescence, and the parental c3BFP gave bright blue fluorescence. In the genes encoding these fluorescent proteins, the sequences that determine the emission color and those that govern fluorescence intensity are at different positions from one another. It is expected that DNA shuffling would result in the "de-linking" of the sequences that determine the emission color from those that govern fluorescence intensity. As a consequence, the resultant progeny would be expected to exhibit reassortment of the functional properties of emission color and intensity. Therefore a measure of the extent of the DNA shuffling that had taken place in each reaction could be scored by examining the color and intensity of fluorescence from the bacterial colonies on the corresponding plates. In the zero-nuclease control, only dim green and bright blue colonies were observed. However, on plates with cells transformed with DNAs from the reactions containing either CEL I or RES I, some bright green as well as some dim blue colonies were observed, indicating that shuffling of DNA sequences had taken place. DNA sequence analysis confirmed that this was indeed the case and that on average, the recovery of shuffled clones was greater than 85% for both CEL I and RES I and that the number and distribution of information transfer events was similar for both enzymes. However, it appeared that the activity of RES I in this experiment was several-fold higher than that of CEL I, as indicated by the low transformation efficiency of reactions treated with the higher concentrations of the RES I preparation.

EXAMPLE 15

Molecular Breeding of Highly Divergent Tobamovirus 30K Genes in Viral Vectors using Plasmid-on-Plasmid Genetic Reassortment By DNA Mismatch Resolution (POP GRAMMR)

Example 10 taught the reassortment of movement protein (MP) genes from several divergent strains of tobamovirus (approximately 75% identical; cloned into the pGENEWARE-MP-Avr-Pac vector) using GRAMMR. This example teaches the use of Plasmid-on-plasmid GRAMMR (POP GRAMMR) for reassorting even more highly divergent species.

Starting parental MP genes from the tobamoviruses TMV-Cg (FIG. 6, SEQ ID NO: 18), TMV-Ob (FIG. 7, SEQ ID NO: 19), TMV-U2 (FIG. 8, SEQ ID NO: 20), TMV-U1 (SEQ ID NO: 9), and tomato mosaic virus (ToMV) (SEQ ID NO: 10) were used. The plasmid of pGENEWARE-ToMV MP was linearized by digestion with Sma I. The plasmids of pGENEWARE containing the MP genes from either TMV-Cg, TMV-Ob, TMV-U2, or TMV-U1 were digested with Stu I. The digested pGENEWARE-MP constructs were purified using DNA spin columns. The following heterduplex pairs were generated: pGENEWARE-Cg MP and pGENEWARE-ToMV MP, pGENEWARE-TMV-Ob MP and pGENEWARE-ToMV MP, pGENEWARE-TMV-U2 MP and pGENEWARE-ToMV MP, pGENEWARE-TMV-U1 MP and pGENEWARE-ToMV MP. The heteroduplexes of these MP gene sequences are approximately 54%, 65%, 66%, and 75% identical, respectively. The sequence identity scores were derived by aligning the region containing mismatches in each pair using ClustalX (gap opening penalty of 10 and a gap extension penalty of 2), then dividing the number of identical bases in the alignment by the number of bases in the shorter of the two sequences in the alignment. Heteroduplex DNA was generated by mixing 200 nanograms of each of the two linearized plasmids in 1× SSPE (180 mM NaCl, 10 mM $NaH_2PO_4$, 1 mM EDTA, at pH 7.4) in a volume of 20 microliters. The mixture was incubated at 95 degrees Celsius for 4 minutes, plunged into ice water where it remained for 10 minutes prior to incubation at 37 degrees Celsius. After 30 minutes, the annealed DNA sample was then transferred back to ice where it was held until use in GRAMMR reactions.

Each 10 microliter GRAMMR reaction contained 1 unit of T4 DNA polymerase, 2 units of *E. coli* DNA ligase, and 0.5 mM of each dNTP in 1× NEB *E. coli* DNA ligase buffer supplemented with KCl to 50 mM. A one microliter aliquot of CEL I (diluted 1/3, 1/9, 1/27, 1/81, 1/243, or 1/729) was next added. An endonuclease-free control reaction was also prepared. To each of the reactions, a one microliter aliquot containing 20 nanograms of the annealed DNA heteroduplex substrate was added and the reactions were incubated at room temperature for one hour and on ice for 30 minutes prior to transformation into competent *E. coli.*

DNA sequence analysis was performed from both directions, and the sequence data showed that a significant number of clones derived from the GRAMMR-treated material were reasserted sequences containing information from both parental movement protein gene sequences. The DNA sequences of several exemplary out output pGENEWARE-MP clones from the GRAMMR reaction are shown as follows, TMV-Cg/ToMV clones, FIG. 9, SEQ ID NO: 21, and FIG. 10, SEQ ID NO: 22; TMV-Ob/ToMV clones, FIG. 11, SEQ ID NO: 23, and FIG. 12, SEQ ID NO: 24; TMV-U2/ToMV clones, FIG. 13, SEQ ID NO: 25, and FIG. 14, SEQ ID NO: 26; and TMV-U1/ToMV clones, FIG. 15, SEQ ID NO: 27, and FIG. 16, SEQ ID NO: 28.

EXAMPLE 16

GRAMMR On Linearized DNA Substrate Using Endonucleases That Cleave Within A Selectable Marker This example teaches a GRAMMR reaction where DNA substrate molecules are linearized with restriction endonucleases that cleave within a selectable marker gene.

GRAMMR is performed between the wild-type Aequorea victoria GFP gene (Prasher, et al., Gene111(92)229) in a pBS derivative (Stratagene, La Jolla, Calif.) encoded by pBSWT-GFβ (SEQ ID NO:31) and a variant with mutations to increase fluorescence intensity in *E. coli*, and to alter the emission wavelength to blue light emission (Crameri, et al., Nat Biotechnol 14 (96) 315; Heim et al., PNAS91(94)12501; Yang, et al., J Biol Chem 273(98)8212). This variant gene, encoded by the plasmid pBSC3BFP (SEQ ID NO: 32), encodes a fluorescent protein that emits bright blue light when excited by longwave UV light.

The GRAMMR reactions are performed on GFP/c3BFP heteroduplexes in a circular, double-stranded plasmid DNA context. The circular, whole-plasmid heteroduplex DNA substrates are prepared by first linearizing pBSWTGFP (SEQ ID NO:31) and pBSC3BFP (SEQ ID NO: 32) by digestion with Ahd I and Bcg I, respectively, then purifying the digested DNA using DNA spin columns. Next, 200 nanograms of each of the two linearized plasmids are mixed and brought to 1× SSPE (180 nM NaCl, 10 mM $NaH_2PO4$, 1 mM EDTA at pH 7.4) in a volume of 20 microliters. The mixture is then incubated at 95 degrees Celsius for 4 minutes, plunged into ice-water where it remains for 10 minutes prior to incubation at 37 degrees Celsius. After 30 minutes, the annealed DNA sample is then transferred back to ice where it is held until use in GRAMMR reactions.

Two independent series of reassortment reactions are performed to compare CEL I with RES I in their abilities to facilitate sequence reassortment by GRAMMR. Each reaction is first treated for 10 minutes at room-temperature with 1 unit of T4 DNA polymerase in the presence of 5 nanomoles of each DNTP in 1× NEB *E. coli* ligase buffer supplemented with KCl to 50 mM. Subsequently, 2 units of *E. coli* DNA ligase are added. Two separate enzyme dilution series are then performed. To each of two series of tubes containing aliquots of the above cocktail, one microliter aliquots of GENEWARE®-expressed CEL I or RES I extracts at dilutions of 1/3, 1/9, 1/27, 1/81, or 1/243 are added. An endonuclease-free control reaction is also prepared. To each of the reactions, one microliter aliquots containing 20 nanograms of the annealed DNA heteroduplex substrate are added and the reactions incubated at room temperature for one hour and on ice for 30 minutes prior to transformation into competent *E. coli.*

Green fluorescent protein (GFP) and blue fluorescent protein (BFP) is visualized in the resulting colonies by long wave UV illumination. The parental wild-type GFP gives dim green fluorescence, and the parental c3BFP gives bright blue fluorescence. In the genes encoding these fluorescent proteins, the sequences that determine the emission color and those that govern fluorescence intensity are at different positions from one another.

It is expected that DNA reassortment would result in the "de-linking" of the sequences that determine the emission color from those that govern fluorescence intensity. As a consequence, the resultant progeny would be expected to exhibit reassortment of the functional properties of emission color and intensity. Therefore a measure of the extent of the DNA reassortment that had taken place in each reaction can be scored by examining the color and intensity of fluorescence from the bacterial colonies on the corresponding plates.

Deposits with The American Type Culture Collection (ATCC)

Three deposits have been made in the American Type Culture Collection (ATCC), 10801 University Blvd., Manassas, Va. A deposit has been made of a plasmid DNA construct containing a derivative of tobacco mosaic virus and cDNA of the CEL I mismatch-endonuclease gene from celery, tagged with 6HIS. The construct is internally designated P1177 MP4-CEL I 6HIS, and has been assigned ATCC Number PTA-3927. A deposit has been made of a plasmid DNA construct containing a derivative of tobacco mosaic virus and cDNA of the CEL I mismatch-endonuclease gene from celery. The construct is internally designated P1177 MP4-CEL I Avr, and has been assigned ATCC Number PTA-3926. A deposit has been made of a plasmid DNA construct containing a derivative of tobacco mosaic virus and a cDNA insert encoding a 34 kDa protein from *Selaginella lepidophylla*. The cDNA insert is referred to as RES I-6HIS. RES I is a mismatch endonuclease gene. The construct is internally designated pLSB-2225, and has been assigned ATCC Number PTA-4562.

These deposits were made in accordance with the terms and provisions of the Budapest Treaty relating to deposit of microorganisms and was made for a term of at least thirty (30) years and at least five (05) years after the most recent request for the furnishing of a sample of the deposit is received by the depository, or for the effective term of a patent to issue from this application or a subsequent application citing any of these deposits, whichever is longer. Each deposit will be replaced if it becomes non-viable during that period.

All restrictions on the accessibility of the deposited biological material will be irrevocably removed by the Applicants upon the granting of the patent.

It should be noted that applicant's designations for each of the clones were shortened in the deposit to the aforementioned deposit with the American Type Culture Collection, that is, p1177 MP4-CEL I Avr-B3 is referred to as p1177 MP4-CEL I Avr; and p1177 MP4-CEL I 6His-A9 is referred to as p1177 MP4-CEL I 6His. The clone p1177 MP4-CEL I Avr (SEQ ID NO:01) contained the CEL I open reading frame extending from nucleotide 5765 to 6655 (SEQ ID NO:03); and the clone p1177 MP4-CEL I 6His-A9 (SEQ ID NO:02) contained the CEL I open reading frame extending from nucleotide 5765-6679 (SEQ ID NO:04).

SEQUENCE LISTING

<160> NUMBER OF SEQ ID NOS: 35

<210> SEQ ID NO 1
<211> LENGTH: 10600
<212> TYPE: DNA
<213> ORGANISM: Artificial Sequence
<220> FEATURE:
<223> OTHER INFORMATION: TMV infectious clone containing CEL I gene

<400> SEQUENCE: 1
gtatttttac aacaattacc aacaacaaca aacaacaaac aacattacaa ttactattta 60
caattacaat ggcatacaca cagacagcta ccacatcagc tttgctggac actgtccgag 120
gaaacaactc cttggtcaat gatctagcaa agcgtcgtct ttacgacaca gcggttgaag 180
agtttaacgc tcgtgaccgc aggcccaagg tgaacttttc aaaagtaata agcgaggagc 240
agacgcttat tgctacccgg gcgtatccag aattccaaat tacattttat aacacgcaaa 300
atgccgtgca ttcgcttgca ggtggattgc gatctttaga actggaatat ctgatgatgc 360
aaattcccta cggatcattg acttatgaca taggcgggaa ttttgcatcg catctgttca 420
agggacgagc atatgtacac tgctgcatgc ccaacctgga cgttcgagac atcatgcggc 480
acgaaggcca gaaagacagt attgaactat acctttctag gctagagaga ggggggaaaa 540
cagtccccaa cttccaaaag gaagcatttg acagatacgc agaaattcct gaagacgctg 600
tctgtcacaa tactttccag acaatgcgac atcagccgat gcagcaatca ggcagagtgt 660
atgccattgc gctacacagc atatatgaca taccagccga tgagttcggg gcggcactct 720
tgaggaaaaa tgtccatacg tgctatgccg ctttccactt ctctgagaac ctgcttcttg 780
aagattcata cgtcaatttg gacgaaatca acgcgtgttt ttcgcgcgat ggagacaagt 840
tgaccttttc ttttgcatca gagagtactc ttaattattg tcatagttat tctaatattc 900
ttaagtatgt gtgcaaaact tacttcccgg cctctaatag agaggtttac atgaaggagt 960
ttttagtcac cagagttaat acctggtttt gtaagttttc tagaatagat acttttcttt 1020
tgtacaaagg tgtggcccat aaaagtgtag atagtgagca gttttatact gcaatggaag 1080
acgcatggca ttacaaaaag actcttgcaa tgtgcaacag cgagagaatc ctccttgagg 1140
attcatcatc agtcaattac tggtttccca aaatgaggga tatggtcatc gtaccattat 1200
tcgacatttc tttggagact agtaagagga cgcgcaagga agtcttagtg tccaaggatt 1260
tcgtgtttac agtgcttaac cacattcgaa cataccaggc gaaagctctt acatacgcaa 1320
atgttttgtc ctttgtcgaa tcgattcgat cgagggtaat cattaacggt gtgacagcga 1380
ggtccgaatg ggatgtggac aaatctttgt tacaatcctt gtccatgacg ttttacctgc 1440
atactaagct tgccgttcta aaggatgact tactgattag caagtttagt ctcggttcga 1500
aaacggtgtg ccagcatgtg tgggatgaga tttcgctggc gtttgggaac gcatttccct 1560

-continued

```
ccgtgaaaga gaggctcttg aacaggaaac ttatcagagt ggcaggcgac gcattagaga   1620
tcagggtgcc tgatctatat gtgaccttcc acgacagatt agtgactgag tacaaggcct   1680
ctgtggacat gcctgcgctt gacattagga agaagatgga agaaacggaa gtgatgtaca   1740
atgcactttc agagttatcg gtgttaaggg agtctgacaa attcgatgtt gatgtttttt   1800
cccagatgtg ccaatctttg gaagttgacc caatgacggc agcgaaggtt atagtcgcgg   1860
tcatgagcaa tgagagcggt ctgactctca catttgaacg acctactgag gcgaatgttg   1920
cgctagcttt acaggatcaa gagaaggctt cagaaggtgc tttggtagtt acctcaagag   1980
aagttgaaga accgtccatg aagggttcga tggccagagg agagttacaa ttagctggtc   2040
ttgctggaga tcatccggag tcgtcctatt ctaagaacga ggagatagag tctttagagc   2100
agtttcatat ggcaacggca gattcgttaa ttcgtaagca gatgagctcg attgtgtaca   2160
cgggtccgat taaagttcag caaatgaaaa actttatcga tagcctggta gcatcactat   2220
ctgctgcggt gtcgaatctc gtcaagatcc tcaaagatac agctgctatt gaccttgaaa   2280
cccgtcaaaa gtttggagtc ttggatgttg catctaggaa gtggttaatc aaaccaacgg   2340
ccaagagtca tgcatggggt gttgttgaaa cccacgcgag gaagtatcat gtggcgcttt   2400
tggaatatga tgagcagggt gtggtgacat gcgatgattg gagaagagta gctgtcagct   2460
ctgagtctgt tgtttattcc gacatggcga aactcagaac tctgcgcaga ctgcttcgaa   2520
acggagaacc gcatgtcagt agcgcaaagg ttgttcttgt ggacggagtt ccgggctgtg   2580
ggaaaaccaa agaaattctt tccagggtta attttgatga agatctaatt ttagtacctg   2640
ggaagcaagc cgcggaaatg atcagaagac gtgcgaattc ctcagggatt attgtggcca   2700
cgaaggacaa cgttaaaacc gttgattctt tcatgatgaa ttttgggaaa agcacacgct   2760
gtcagttcaa gaggttattc attgatgaag ggttgatgtt gcatactggt tgtgttaatt   2820
ttcttgtggc gatgtcattg tgcgaaattg catatgttta cggagacaca cagcagattc   2880
catacatcaa tagagtttca ggattcccgt accccgccca ttttgccaaa ttggaagttg   2940
acgaggtgga gacacgcaga actactctcc gttgtccagc cgatgtcaca cattatctga   3000
acaggagata tgagggcttt gtcatgagca cttcttcggt taaaaagtct gtttcgcagg   3060
agatggtcgg cggagccgcc gtgatcaatc cgatctcaaa acccttgcat ggcaagatcc   3120
tgacttttac ccaatcggat aaagaagctc tgctttcaag agggtattca gatgttcaca   3180
ctgtgcatga agtgcaaggc gagacatact ctgatgtttc actagttagg ttaaccccta   3240
caccagtctc catcattgca ggagacagcc cacatgtttt ggtcgcattg tcaaggcaca   3300
cctgttcgct caagtactac actgttgtta tggatccttt agttagtatc attagagatc   3360
tagagaaact tagctcgtac ttgttagata tgtataaggt cgatgcagga acacaatagc   3420
aattacagat tgactcggtg ttcaaaggtt ccaatctttt tgttgcagcg ccaaagactg   3480
gtgatatttc tgatatgcag ttttactatg ataagtgtct cccaggcaac agcaccatga   3540
tgaataattt tgatgctgtt accatgaggt tgactgacat ttcattgaat gtcaaagatt   3600
gcatattgga tatgtctaag tctgttgctg cgcctaagga tcaaatcaaa ccactaatac   3660
ctatggtacg aacggcggca gaaatgccac gccagactgg actattggaa aatttagtgg   3720
cgatgattaa aaggaacttt aacgcacccg agttgtctgg catcattgat attgaaaata   3780
ctgcatcttt agttgtagat aagttttttg atagttattt gcttaaagaa aaaagaaaac   3840
caaataaaaa tgtttctttg ttcagtagag agtctctcaa tagatggtta gaaaagcagg   3900
aacaggtaac aataggccag ctcgcagatt ttgattttgt agatttgcca gcagttgatc   3960
```

-continued agtacagaca catgattaaa gcacaaccca agcaaaaatt ggacacttca atccaaacgg 4020
agtacccggc tttgcagacg attgtgtacc attcaaaaaa gatcaatgca atatttggcc 4080
cgttgtttag tgagcttact aggcaattac tggacagtgt tgattcgagc agatttttgt 4140
ttttcacaag aaagacacca gcgcagattg aggatttctt cggagatctc gacagtcatg 4200
tgccgatgga tgtcttggag ctggatatat caaaatacga caaatctcag aatgaattcc 4260
actgtgcagt agaatacgag atctggcgaa gattgggttt tgaagacttc ttgggagaag 4320
tttggaaaca agggcataga aagaccaccc tcaaggatta taccgcaggt ataaaaactt 4380
gcatctggta tcaaagaaag agcggggacg tcacgacgtt cattggaaac actgtgatca 4440
ttgctgcatg tttggcctcg atgcttccga tggagaaaat aatcaaagga gccttttgcg 4500
gtgacgatag tctgctgtac tttccaaagg gttgtgagtt tccggatgtg caacactccg 4560
cgaatcttat gtggaatttt gaagcaaaac tgtttaaaaa acagtatgga tacttttgcg 4620
gaagatatgt aatacatcac gacagaggat gcattgtgta ttacgatccc ctaaagttga 4680
tctcgaaact tggtgctaaa cacatcaagg attgggaaca cttggaggag ttcagaaggt 4740
ctctttgtga tgttgctgtt tcgttgaaca attgtgcgta ttacacacag ttggacgacg 4800
ctgtatggga ggttcataag accgcccctc caggttcgtt tgtttataaa agtctggtga 4860
agtatttgtc tgataaagtt ctttttagaa gtttgtttat agatggctct agttgttaaa 4920
ggaaaagtga atatcaatga gtttatcgac ctgacaaaaa tggagaagat cttaccgtcg 4980
atgtttaccc ctgtaaagag tgttatgtgt tccaaagttg ataaaataat ggttcatgag 5040
aatgagtcat tgtcagaggt gaaccttctt aaaggagtta agcttattga tagtggatac 5100
gtctgtttag ccggtttggt cgtcacgggc gagtggaact tgcctgacaa ttgcagagga 5160
ggtgtgagcg tgtgtctggt ggacaaaagg atggaaagag ccgacgaggc cactctcgga 5220
tcttactaca cagcagctgc aaagaaaaga tttcagttca aggtcgttcc caattatgct 5280
ataaccaccc aggacgcgat gaaaaacgtc tggcaagttt tagttaatat tagaaatgtg 5340
aagatgtcag cgggtttctg tccgctttct ctggagtttg tgtcggtgtg tattgtttat 5400
agaaataata taaaattagg tttgagagag aagattacaa acgtgagaga cggagggccc 5460
atggaactta cagaagaagt cgttgatgag ttcatggaag atgtccctat gtcgatcagg 5520
cttgcaaagt ttcgatctcg aaccggaaaa aagagtgatg tccgcaaagg gaaaaatagt 5580
agtaatgatc ggtcagtgcc gaacaagaac tatagaaatg ttaaggattt tggaggaatg 5640
agttttaaaa agaataattt aatcgatgat gattcggagg ctactgtcgc cgaatcggat 5700
tcgttttaaa tagatcttac agtatcacta ctccatctca gttcgtgttc ttgtcattaa 5760
ttaaatgacg cgattatatt ctgtgttctt tcttttgttg gctcttgtag ttgaaccggg 5820
tgttagagcc tggagcaaag aaggccatgt catgacatgt caaattgcgc aggatctgtt 5880
ggagccagaa gcagcacatg ctgtaaagat gctgttaccg gactatgcta atggcaactt 5940
atcgtcgctg tgtgtgtggc ctgatcaaat tcgacactgg tacaagtaca ggtggactag 6000
ctctctccat ttcatcgata cacctgatca agcctgttca tttgattacc agagagactg 6060
tcatgatcca catggaggga aggacatgtg tgttgctgga gccattcaaa atttcacatc 6120
tcagcttgga catttccgcc atggaacatc tgatcgtcga tataatatga cagaggcttt 6180
gttattttta tcccacttca tgggagatat tcatcagcct atgcatgttg gatttacaag 6240
tgatatggga ggaaacagta tagatttgcg ctggtttcgc cacaaatcca acctgcacca 6300

-continued tgtttgggat agagagatta ttcttacagc tgcagcagat taccatggta aggatatgca 6360
ctctctccta caagacatac agaggaactt tacagagggt agttggttgc aagatgttga 6420
atcctggaag gaatgtgatg atatctctac ttgcgccaat aagtatgcta aggagagtat 6480
aaaactagcc tgtaactggg gttacaaaga tgttgaatct ggcgaaactc tgtcagataa 6540
atacttcaac acaagaatgc caattgtcat gaaacggata gctcagggtg gaatccgttt 6600
atccatgatt ttgaaccgag ttcttggaag ctccgcagat cattctttgg catgacctag 6660
gccagtagtt tggtttaaac ccaactgcga ggggtagtca agatgcataa taaataacgg 6720
attgtgtccg taatcacacg tggtgcgtac gataacgcat agtgtttttc cctccactta 6780
aatcgaaggg ttgtgtcttg gatcgcgcgg gtcaaatgta tatggttcat atacatccgc 6840
aggcacgtaa taaagcgagg ggttcgggtc gaggtcggct gtgaaactcg aaaaggttcc 6900
ggaaaacaaa aaagagatgg taggtaatag tgttaataat aagaaaataa ataatagtgg 6960
taagaaaggt ttgaaagttg aggaaattga ggataatgta agtgatgacg agtctatcgc 7020
gtcatcgagt acgttttaat caatatgcct tatacaatca actctccgag ccaatttgtt 7080
tacttaagtt ccgcttatgc agatcctgtg cagctgatca atctgtgtac aaatgcattg 7140
ggtaaccagt ttcaaacgca acaagctagg acaacagtcc aacagcaatt tgcggatgcc 7200
tggaaacctg tgcctagtat gacagtgaga tttcctgcat cggatttcta tgtgtataga 7260
tataattcga cgcttgatcc gttgatcacg gcgttattaa atagcttcga tactagaaat 7320
agaataatag aggttgataa tcaacccgca ccgaatacta ctgaaatcgt taacgcgact 7380
cagagggtag acgatgcgac tgtagctata agggcttcaa tcaataattt ggctaatgaa 7440
ctggttcgtg gaactggcat gttcaatcaa gcaagctttg agactgctag tggacttgtc 7500
tggaccacaa ctccggctac ttagctattg ttgtgagatt tcctaaaata aagtcactga 7560
agacttaaaa ttcagggtgg ctgataccaa aatcagcagt ggttgttcgt ccacttaaat 7620
ataacgattg tcatatctgg atccaacagt taaaccatgt gatggtgtat actgtggtat 7680
ggcgtaaaac aacggaaaag tcgctgaaga cttaaaattc agggtggctg ataccaaaat 7740
cagcagtggt tgttcgtcca cttaaaaata acgattgtca tatctggatc caacagttaa 7800
accatgtgat ggtgtatact gtggtatggc gtaaaacaac ggagaggttc gaatcctccc 7860
ctaaccgcgg gtagcggccc aggtacccgg atgtgttttc cgggctgatg agtccgtgag 7920
gacgaaaccc ggcatgcaag cttggcgtaa tcatggtcat agctgtttcc tgtgtgaaat 7980
tgttatccgc tcacaattcc acacaacata cgagccggaa gcataaagtg taaagcctgg 8040
ggtgcctaat gagtgagcta actcacatta attgcgttgc gctcactgcc cgctttccag 8100
tcgggaaacc tgtcgtgcca gctgcattaa tgaatcggcc aacgcgcggg gagaggcggt 8160
ttgcgtattg ggcgctcttc cgcttcctcg ctcactgact cgctgcgctc ggtcgttcgg 8220
ctgcggcgag cggtatcagc tcactcaaag gcggtaatac ggttatccac agaatcaggg 8280
gataacgcag gaaagaacat gtgagcaaaa ggccagcaaa aggccaggaa ccgtaaaaag 8340
gccgcgttgc tggcgttttt ccataggctc cgcccccctg acgagcatca caaaaatcga 8400
cgctcaagtc agaggtggcg aaacccgaca ggactataaa gataccaggc gtttccccct 8460
ggaagctccc tcgtgcgctc tcctgttccg accctgccgc ttaccggata cctgtccgcc 8520
tttctccctt cgggaagcgt ggcgctttct catagctcac gctgtaggta tctcagttcg 8580
gtgtaggtcg ttcgctccaa gctgggctgt gtgcacgaac cccccgttca gcccgaccgc 8640
tgcgccttat ccggtaacta tcgtcttgag tccaacccgg taagacacga cttatcgcca 8700

-continued

```
ctggcagcag ccactggtaa caggattagc agagcgaggt atgtaggcgg tgctacagag   8760

ttcttgaagt ggtggcctaa ctacggctac actagaagga cagtatttgg tatctgcgct   8820

ctgctgaagc cagttacctt cggaaaaaga gttggtagct cttgatccgg caaacaaacc   8880

accgctggta gcggtggttt ttttgtttgc aagcagcaga ttacgcgcag aaaaaaagga   8940

tctcaagaag atcctttgat cttttctacg gggtctgacg ctcagtggaa cgaaaactca   9000

cgttaaggga ttttggtcat gagattatca aaaaggatct tcacctagat ccttttaaat   9060

taaaaatgaa gttttaaatc aatctaaagt atatatgagt aaacttggtc tgacagttac   9120

caatgcttaa tcagtgaggc acctatctca gcgatctgtc tatttcgttc atccatagtt   9180

gcctgactcc ccgtcgtgta gataactacg atacgggagg gcttaccatc tggccccagt   9240

gctgcaatga taccgcgaga cccacgctca ccggctccag atttatcagc aataaaccag   9300

ccagccggaa gggccgagcg cagaagtggt cctgcaactt tatccgcctc catccagtct   9360

attaattgtt gccgggaagc tagagtaagt agttcgccag ttaatagttt gcgcaacgtt   9420

gttgccattg ctacaggcat cgtggtgtca cgctcgtcgt ttggtatggc ttcattcagc   9480

tccggttccc aacgatcaag gcgagttaca tgatccccca tgttgtgcaa aaaagcggtt   9540

agctccttcg gtcctccgat cgttgtcaga agtaagttgg ccgcagtgtt atcactcatg   9600

gttatggcag cactgcataa ttctcttact gtcatgccat ccgtaagatg cttttctgtg   9660

actggtgagt actcaaccaa gtcattctga gaatagtgta tgcggcgacc gagttgctct   9720

tgcccggcgt caatacggga taataccgcg ccacatagca gaactttaaa agtgctcatc   9780

attggaaaac gttcttcggg gcgaaaactc tcaaggatct taccgctgtt gagatccagt   9840

tcgatgtaac ccactcgtgc acccaactga tcttcagcat cttttacttt caccagcgtt   9900

tctgggtgag caaaaacagg aaggcaaaat gccgcaaaaa agggaataag ggcgacacgg   9960

aaatgttgaa tactcatact cttccttttt caatattatt gaagcattta tcagggttat  10020

tgtctcatga gcggatacat atttgaatgt atttagaaaa ataaacaaat aggggttccg  10080

cgcacatttc cccgaaaagt gccacctgac gtctaagaaa ccattattat catgacatta  10140

acctataaaa ataggcgtat cacgaggccc tttcgtctcg cgcgtttcgg tgatgacggt  10200

gaaaacctct gacacatgca gctcccggag acggtcacag cttgtctgta agcggatgcc  10260

gggagcagac aagcccgtca gggcgcgtca gcgggtgttg gcgggtgtcg gggctggctt  10320

aactatgcgg catcagagca gattgtactg agagtgcacc atatgcggtg tgaaataccg  10380

cacagatgcg taaggagaaa ataccgcatc aggcgccatt cgccattcag gctgcgcaac  10440

tgttgggaag ggcgatcggt gcgggcctct tcgctattac gccagctggc gaaaggggga  10500

tgtgctgcaa ggcgattaag ttgggtaacg ccagggtttt cccagtcacg acgttgtaaa  10560

acgacggcca gtgaattcaa gcttaatacg actcactata                        10600
```

```
<210> SEQ ID NO 2
<211> LENGTH: 10624
<212> TYPE: DNA
<213> ORGANISM: Artificial Sequence
<220> FEATURE:
<223> OTHER INFORMATION: TMV infectous clone containing CEL I gene fused
      to a 6HIS encoding sequence

<400> SEQUENCE: 2

gtatttttac aacaattacc aacaacaaca aacaacaaac aacattacaa ttactattta     60

caattacaat ggcatacaca cagacagcta ccacatcagc tttgctggac actgtccgag    120
```

-continued

```
gaaacaactc cttggtcaat gatctagcaa agcgtcgtct ttacgacaca gcggttgaag    180
agtttaacgc tcgtgaccgc aggcccaagg tgaacttttc aaaagtaata agcgaggagc    240
agacgcttat tgctacccgg gcgtatccag aattccaaat tacattttat aacacgcaaa    300
atgccgtgca ttcgcttgca ggtggattgc gatctttaga actggaatat ctgatgatgc    360
aaattcccta cggatcattg acttatgaca taggcgggaa ttttgcatcg catctgttca    420
agggacgagc atatgtacac tgctgcatgc ccaacctgga cgttcgagac atcatgcggc    480
acgaaggcca gaaagacagt attgaactat acctttctag gctagagaga gggggggaaaa    540
cagtccccaa cttccaaaag gaagcatttg acagatacgc agaaattcct gaagacgctg    600
tctgtcacaa tactttccag acaatgcgac atcagccgat gcagcaatca ggcagagtgt    660
atgccattgc gctacacagc atatatgaca taccagccga tgagttcggg gcggcactct    720
tgaggaaaaa tgtccatacg tgctatgccg ctttccactt ctctgagaac ctgcttcttg    780
aagattcata cgtcaatttg gacgaaatca acgcgtgttt ttcgcgcgat ggagacaagt    840
tgaccttttc ttttgcatca gagagtactc ttaattattg tcatagttat tctaatattc    900
ttaagtatgt gtgcaaaact tacttcccgg cctctaatag agaggtttac atgaaggagt    960
ttttagtcac cagagttaat acctggtttt gtaagttttc tagaatagat acttttcttt   1020
tgtacaaagg tgtggcccat aaaagtgtag atagtgagca gttttatact gcaatggaag   1080
acgcatggca ttacaaaaag actcttgcaa tgtgcaacag cgagagaatc ctccttgagg   1140
attcatcatc agtcaattac tggtttccca aaatgaggga tatggtcatc gtaccattat   1200
tcgacatttc tttggagact agtaagagga cgcgcaagga agtcttagtg tccaaggatt   1260
tcgtgtttac agtgcttaac cacattcgaa cataccaggc gaaagctctt acatacgcaa   1320
atgttttgtc ctttgtcgaa tcgattcgat cgagggtaat cattaacggt gtgacagcga   1380
ggtccgaatg ggatgtggac aaatctttgt tacaatcctt gtccatgacg ttttacctgc   1440
atactaagct tgccgttcta aaggatgact tactgattag caagtttagt ctcggttcga   1500
aaacggtgtg ccagcatgtg tgggatgaga tttcgctggc gtttgggaac gcatttccct   1560
ccgtgaaaga gaggctcttg aacaggaaac ttatcagagt ggcaggcgac gcattagaga   1620
tcagggtgcc tgatctatat gtgaccttcc acgacagatt agtgactgag tacaaggcct   1680
ctgtggacat gcctgcgctt gacattagga agaagatgga agaaacggaa gtgatgtaca   1740
atgcactttc agagttatcg gtgttaaggg agtctgacaa attcgatgtt gatgtttttt   1800
cccagatgtg ccaatctttg gaagttgacc caatgacggc agcgaaggtt atagtcgcgg   1860
tcatgagcaa tgagagcggt ctgactctca catttgaacg acctactgag gcgaatgttg   1920
cgctagcttt acaggatcaa gagaaggctt cagaaggtgc tttggtagtt acctcaagag   1980
aagttgaaga accgtccatg aagggttcga tggccagagg agagttacaa ttagctggtc   2040
ttgctggaga tcatccggag tcgtcctatt ctaagaacga ggagatagag tctttagagc   2100
agtttcatat ggcaacggca gattcgttaa ttcgtaagca gatgagctcg attgtgtaca   2160
cgggtccgat taaagttcag caaatgaaaa actttatcga tagcctggta gcatcactat   2220
ctgctgcggt gtcgaatctc gtcaagatcc tcaaagatac agctgctatt gaccttgaaa   2280
cccgtcaaaa gtttggagtc ttggatgttg catctaggaa gtggttaatc aaaccaacgg   2340
ccaagagtca tgcatggggt gttgttgaaa cccacgcgag gaagtatcat gtggcgcttt   2400
tggaatatga tgagcagggt gtggtgacat gcgatgattg gagaagagta gctgtcagct   2460
```

-continued ctgagtctgt tgtttattcc gacatggcga aactcagaac tctgcgcaga ctgcttcgaa 2520
acggagaacc gcatgtcagt agcgcaaagg ttgttcttgt ggacggagtt ccgggctgtg 2580
ggaaaaccaa agaaattctt tccagggtta attttgatga agatctaatt ttagtacctg 2640
ggaagcaagc cgcggaaatg atcagaagac gtgcgaattc ctcagggatt attgtggcca 2700
cgaaggacaa cgttaaaacc gttgattctt tcatgatgaa ttttgggaaa agcacacgct 2760
gtcagttcaa gaggttattc attgatgaag ggttgatgtt gcatactggt tgtgttaatt 2820
ttcttgtggc gatgtcattg tgcgaaattg catatgttta cggagacaca cagcagattc 2880
catacatcaa tagagtttca ggattcccgt accccgccca ttttgccaaa ttggaagttg 2940
acgaggtgga gacacgcaga actactctcc gttgtccagc cgatgtcaca cattatctga 3000
acaggagata tgagggcttt gtcatgagca cttcttcggt taaaaagtct gtttcgcagg 3060
agatggtcgg cggagccgcc gtgatcaatc cgatctcaaa acccttgcat ggcaagatcc 3120
tgacttttac ccaatcggat aaagaagctc tgctttcaag agggtattca gatgttcaca 3180
ctgtgcatga agtgcaaggc gagacatact ctgatgtttc actagttagg ttaaccccta 3240
caccagtctc catcattgca ggagacagcc cacatgtttt ggtcgcattg tcaaggcaca 3300
cctgttcgct caagtactac actgttgtta tggatccttt agttagtatc attagagatc 3360
tagagaaact tagctcgtac ttgttagata tgtataaggt cgatgcagga acacaatagc 3420
aattacagat tgactcggtg ttcaaaggtt ccaatctttt tgttgcagcg ccaaagactg 3480
gtgatatttc tgatatgcag ttttactatg ataagtgtct cccaggcaac agcaccatga 3540
tgaataattt tgatgctgtt accatgaggt tgactgacat ttcattgaat gtcaaagatt 3600
gcatattgga tatgtctaag tctgttgctg cgcctaagga tcaaatcaaa ccactaatac 3660
ctatggtacg aacggcggca gaaatgccac gccagactgg actattggaa aatttagtgg 3720
cgatgattaa aaggaacttt aacgcacccg agttgtctgg catcattgat attgaaaata 3780
ctgcatcttt agttgtagat aagtttttg atagttattt gcttaaagaa aaaagaaaac 3840
caaataaaaa tgtttctttg ttcagtagag agtctctcaa tagatggtta gaaaagcagg 3900
aacaggtaac aataggccag ctcgcagatt ttgattttgt agatttgcca gcagttgatc 3960
agtacagaca catgattaaa gcacaaccca agcaaaaatt ggacacttca atccaaacgg 4020
agtacccggc tttgcagacg attgtgtacc attcaaaaaa gatcaatgca atatttggcc 4080
cgttgtttag tgagcttact aggcaattac tggacagtgt tgattcgagc agatttttgt 4140
ttttcacaag aaagacacca gcgcagattg aggatttctt cggagatctc gacagtcatg 4200
tgccgatgga tgtcttggag ctggatatat caaaatacga caaatctcag aatgaattcc 4260
actgtgcagt agaatacgag atctggcgaa gattgggttt tgaagacttc ttgggagaag 4320
tttggaaaca agggcataga aagaccaccc tcaaggatta taccgcaggt ataaaaactt 4380
gcatctggta tcaaagaaag agcggggacg tcacgacgtt cattggaaac actgtgatca 4440
ttgctgcatg tttggcctcg atgcttccga tggagaaaat aatcaaagga gccttttgcg 4500
gtgacgatag tctgctgtac tttccaaagg gttgtgagtt tccggatgtg caacactccg 4560
cgaatcttat gtggaatttt gaagcaaaac tgtttaaaaa acagtatgga tacttttgcg 4620
gaagatatgt aatacatcac gacagaggat gcattgtgta ttacgatccc ctaaagttga 4680
tctcgaaact tggtgctaaa cacatcaagg attgggaaca cttggaggag ttcagaaggt 4740
ctctttgtga tgttgctgtt tcgttgaaca attgtgcgta ttacacacag ttggacgacg 4800
ctgtatggga ggttcataag accgcccctc caggttcgtt tgtttataaa agtctggtga 4860

-continued

```
agtatttgtc tgataaagtt ctttttagaa gtttgtttat agatggctct agttgttaaa   4920
ggaaaagtga atatcaatga gtttatcgac ctgacaaaaa tggagaagat cttaccgtcg   4980
atgtttaccc ctgtaaagag tgttatgtgt tccaaagttg ataaaataat ggttcatgag   5040
aatgagtcat tgtcagaggt gaaccttctt aaaggagtta agcttattga tagtggatac   5100
gtctgtttag ccggtttggt cgtcacgggc gagtggaact tgcctgacaa ttgcagagga   5160
ggtgtgagcg tgtgtctggt ggacaaaagg atggaaagag ccgacgaggc cactctcgga   5220
tcttactaca cagcagctgc aaagaaaaga tttcagttca aggtcgttcc caattatgct   5280
ataaccaccc aggacgcgat gaaaaacgtc tggcaagttt tagttaatat tagaaatgtg   5340
aagatgtcag cgggtttctg tccgctttct ctggagtttg tgtcggtgtg tattgtttat   5400
agaaataata taaaattagg tttgagagag aagattacaa acgtgagaga cggagggccc   5460
atggaactta cagaagaagt cgttgatgag ttcatggaag atgtccctat gtcgatcagg   5520
cttgcaaagt ttcgatctcg aaccggaaaa aagagtgatg tccgcaaagg gaaaaatagt   5580
agtaatgatc ggtcagtgcc gaacaagaac tatagaaatg ttaaggattt tggaggaatg   5640
agttttaaaa agaataattt aatcgatgat gattcggagg ctactgtcgc cgaatcggat   5700
tcgttttaaa tagatcttac agtatcacta ctccatctca gttcgtgttc ttgtcattaa   5760
ttaaatgacg cgattatatt ctgtgttctt tcttttgttg gctcttgtag ttgaaccggg   5820
tgttagagcc tggagcaaag aaggccatgt catgacatgt caaattgcgc aggatctgtt   5880
ggagccagaa gcagcacatg ctgtaaagat gctgttaccg gactatgcta atggcaactt   5940
atcgtcgctg tgtgtgtggc ctgatcaaat tcgacactgg tacaagtaca ggtggactag   6000
ctctctccat ttcatcgata cacctgatca agcctgttca tttgattacc agagagactg   6060
tcatgatcca catggaggga aggacatgtg tgttgctgga gccattcaaa atttcacatc   6120
tcagcttgga catttccgcc atggaacatc tgatcgtcga tataatatga cagaggcttt   6180
gttattttta tcccacttca tgggagatat tcatcagcct atgcatgttg gatttacaag   6240
tgatatggga ggaaacagta tagatttgcg ctggtttcgc cacaaatcca acctgcacca   6300
tgtttgggat agagagatta ttcttacagc tgcagcagat taccatggta aggatatgca   6360
ctctctccta caagacatac agaggaactt tacagagggt agttggttgc aagatgttga   6420
atcctggaag gaatgtgatg atatctctac ttgcgccaat aagtatgcta aggagagtat   6480
aaaactagcc tgtaactggg gttacaaaga tgttgaatct ggcgaaactc tgtcagataa   6540
atacttcaac acaagaatgc caattgtcat gaaacggata gctcagggtg gaatccgttt   6600
atccatgatt ttgaaccgag ttcttggaag ctccgcagat cattctttgg caggaggtca   6660
ccatcaccat caccattgac ctaggccagt agtttggttt aaacccaact gcgaggggta   6720
gtcaagatgc ataataaata acggattgtg tccgtaatca cacgtggtgc gtacgataac   6780
gcatagtgtt tttccctcca cttaaatcga agggttgtgt cttggatcgc gcgggtcaaa   6840
tgtatatggt tcatatacat ccgcaggcac gtaataaagc gaggggttcg ggtcgaggtc   6900
ggctgtgaaa ctcgaaaagg ttccggaaaa caaaaaagag atggtaggta atagtgttaa   6960
taataagaaa ataaataata gtggtaagaa aggtttgaaa gttgaggaaa ttgaggataa   7020
tgtaagtgat gacgagtcta tcgcgtcatc gagtacgttt taatcaatat gccttataca   7080
atcaactctc cgagccaatt tgtttactta agttccgctt atgcagatcc tgtgcagctg   7140
atcaatctgt gtacaaatgc attgggtaac cagtttcaaa cgcaacaagc taggacaaca   7200
```

-continued

```
gtccaacagc aatttgcgga tgcctggaaa cctgtgccta gtatgacagt gagatttcct   7260
gcatcggatt tctatgtgta tagatataat tcgacgcttg atccgttgat cacggcgtta   7320
ttaaatagct tcgatactag aaatagaata atagaggttg ataatcaacc cgcaccgaat   7380
actactgaaa tcgttaacgc gactcagagg gtagacgatg cgactgtagc tataagggct   7440
tcaatcaata atttggctaa tgaactggtt cgtggaactg gcatgttcaa tcaagcaagc   7500
tttgagactg ctagtggact tgtctggacc acaactccgg ctacttagct attgttgtga   7560
gatttcctaa aataaagtca ctgaagactt aaaattcagg gtggctgata ccaaaatcag   7620
cagtggttgt tcgtccactt aaatataacg attgtcatat ctggatccaa cagttaaacc   7680
atgtgatggt gtatactgtg gtatggcgta aaacaacgga aagtcgctg aagacttaaa   7740
attcagggtg gctgatacca aaatcagcag tggttgttcg tccacttaaa aataacgatt   7800
gtcatatctg gatccaacag ttaaaccatg tgatggtgta tactgtggta tggcgtaaaa   7860
caacggagag gttcgaatcc tcccctaacc gcgggtagcg gcccaggtac ccggatgtgt   7920
tttccgggct gatgagtccg tgaggacgaa acccggcatg caagcttggc gtaatcatgg   7980
tcatagctgt ttcctgtgtg aaattgttat ccgctcacaa ttccacacaa catacgagcc   8040
ggaagcataa agtgtaaagc ctggggtgcc taatgagtga gctaactcac attaattgcg   8100
ttgcgctcac tgcccgcttt ccagtcggga aacctgtcgt gccagctgca ttaatgaatc   8160
ggccaacgcg cggggagagg cggtttgcgt attgggcgct cttccgcttc ctcgctcact   8220
gactcgctgc gctcggtcgt tcggctgcgg cgagcggtat cagctcactc aaaggcggta   8280
atacggttat ccacagaatc aggggataac gcaggaaaga acatgtgagc aaaaggccag   8340
caaaaggcca ggaaccgtaa aaaggccgcg ttgctggcgt ttttccatag gctccgcccc   8400
cctgacgagc atcacaaaaa tcgacgctca agtcagaggt ggcgaaaccc gacaggacta   8460
taaagatacc aggcgtttcc ccctggaagc tccctcgtgc gctctcctgt tccgaccctg   8520
ccgcttaccg gatacctgtc cgcctttctc ccttcgggaa gcgtggcgct ttctcatagc   8580
tcacgctgta ggtatctcag ttcggtgtag gtcgttcgct ccaagctggg ctgtgtgcac   8640
gaaccccccg ttcagcccga ccgctgcgcc ttatccggta actatcgtct tgagtccaac   8700
ccggtaagac acgacttatc gccactggca gcagccactg gtaacaggat tagcagagcg   8760
aggtatgtag gcggtgctac agagttcttg aagtggtggc ctaactacgg ctacactaga   8820
aggacagtat ttggtatctg cgctctgctg aagccagtta ccttcggaaa aagagttggt   8880
agctcttgat ccggcaaaca aaccaccgct ggtagcggtg gtttttttgt ttgcaagcag   8940
cagattacgc gcagaaaaaa aggatctcaa gaagatcctt tgatcttttc tacggggtct   9000
gacgctcagt ggaacgaaaa ctcacgttaa gggattttgg tcatgagatt atcaaaaagg   9060
atcttcacct agatcctttt aaattaaaaa tgaagtttta aatcaatcta aagtatatat   9120
gagtaaactt ggtctgacag ttaccaatgc ttaatcagtg aggcacctat ctcagcgatc   9180
tgtctatttc gttcatccat agttgcctga ctccccgtcg tgtagataac tacgatacgg   9240
gagggcttac catctggccc cagtgctgca atgataccgc gagacccacg ctcaccggct   9300
ccagatttat cagcaataaa ccagccagcc ggaagggccg agcgcagaag tggtcctgca   9360
actttatccg cctccatcca gtctattaat tgttgccggg aagctagagt aagtagttcg   9420
ccagttaata gtttgcgcaa cgttgttgcc attgctacag gcatcgtggt gtcacgctcg   9480
tcgtttggta tggcttcatt cagctccggt tcccaacgat caaggcgagt tacatgatcc   9540
cccatgttgt gcaaaaaagc ggttagctcc ttcggtcctc cgatcgttgt cagaagtaag   9600
```

-continued

```
ttggccgcag tgttatcact catggttatg gcagcactgc ataattctct tactgtcatg   9660
ccatccgtaa gatgcttttc tgtgactggt gagtactcaa ccaagtcatt ctgagaatag   9720
tgtatgcggc gaccgagttg ctcttgcccg gcgtcaatac gggataatac cgcgccacat   9780
agcagaactt taaaagtgct catcattgga aaacgttctt cggggcgaaa actctcaagg   9840
atcttaccgc tgttgagatc cagttcgatg taacccactc gtgcacccaa ctgatcttca   9900
gcatctttta ctttcaccag cgtttctggg tgagcaaaaa caggaaggca aaatgccgca   9960
aaaaagggaa taagggcgac acggaaatgt tgaatactca tactcttcct ttttcaatat  10020
tattgaagca tttatcaggg ttattgtctc atgagcggat acatatttga atgtatttag  10080
aaaaataaac aaataggggt tccgcgcaca tttccccgaa aagtgccacc tgacgtctaa  10140
gaaaccatta ttatcatgac attaacctat aaaaataggc gtatcacgag gccctttcgt  10200
ctcgcgcgtt tcggtgatga cggtgaaaac ctctgacaca tgcagctccc ggagacggtc  10260
acagcttgtc tgtaagcgga tgccgggagc agacaagccc gtcagggcgc gtcagcgggt  10320
gttggcgggt gtcggggctg gcttaactat gcggcatcag agcagattgt actgagagtg  10380
caccatatgc ggtgtgaaat accgcacaga tgcgtaagga gaaaataccg catcaggcgc  10440
cattcgccat tcaggctgcg caactgttgg gaagggcgat cggtgcgggc ctcttcgcta  10500
ttacgccagc tggcgaaagg gggatgtgct gcaaggcgat taagttgggt aacgccaggg  10560
ttttcccagt cacgacgttg taaaacgacg gccagtgaat tcaagcttaa tacgactcac  10620
tata                                                               10624
```

<210> SEQ ID NO 3
<211> LENGTH: 891
<212> TYPE: DNA
<213> ORGANISM: Apium graveolens

<400> SEQUENCE: 3

```
atgacgcgat tatattctgt gttctttctt ttgttggctc ttgtagttga accgggtgtt     60
agagcctgga gcaaagaagg ccatgtcatg acatgtcaaa ttgcgcagga tctgttggag    120
ccagaagcag cacatgctgt aaagatgctg ttaccggact atgctaatgg caacttatcg    180
tcgctgtgtg tgtggcctga tcaaattcga cactggtaca agtacaggtg gactagctct    240
ctccatttca tcgatacacc tgatcaagcc tgttcatttg attaccagag agactgtcat    300
gatccacatg gagggaagga catgtgtgtt gctggagcca ttcaaaattt cacatctcag    360
cttggacatt tccgccatgg aacatctgat cgtcgatata atatgacaga ggctttgtta    420
tttttatccc acttcatggg agatattcat cagcctatgc atgttggatt tacaagtgat    480
atgggaggaa acagtataga tttgcgctgg tttcgccaca aatccaacct gcaccatgtt    540
tgggatagag agattattct tacagctgca gcagattacc atggtaagga tatgcactct    600
ctcctacaag acatacagag gaactttaca gagggtagtt ggttgcaaga tgttgaatcc    660
tggaaggaat gtgatgatat ctctacttgc gccaataagt atgctaagga gagtataaaa    720
ctagcctgta actggggtta caaagatgtt gaatctggcg aaactctgtc agataaatac    780
ttcaacacaa gaatgccaat tgtcatgaaa cggatagctc agggtggaat ccgtttatcc    840
atgattttga accgagttct tggaagctcc gcagatcatt ctttggcatg a             891
```

<210> SEQ ID NO 4
<211> LENGTH: 915
<212> TYPE: DNA

-continued

<213> ORGANISM: Apium graveolens

<400> SEQUENCE: 4
atgacgcgat tatattctgt gttctttctt ttgttggctc ttgtagttga accgggtgtt 60
agagcctgga gcaaagaagg ccatgtcatg acatgtcaaa ttgcgcagga tctgttggag 120
ccagaagcag cacatgctgt aaagatgctg ttaccggact atgctaatgg caacttatcg 180
tcgctgtgtg tgtggcctga tcaaattcga cactggtaca agtacaggtg gactagctct 240
ctccatttca tcgatacacc tgatcaagcc tgttcatttg attaccagag agactgtcat 300
gatccacatg gagggaagga catgtgtgtt gctggagcca ttcaaaattt cacatctcag 360
cttggacatt tccgccatgg aacatctgat cgtcgatata atatgacaga ggctttgtta 420
tttttatccc acttcatggg agatattcat cagcctatgc atgttggatt tacaagtgat 480
atgggaggaa acagtataga tttgcgctgg tttcgccaca aatccaacct gcaccatgtt 540
tgggatagag agattattct tacagctgca gcagattacc atggtaagga tatgcactct 600
ctcctacaag acatacagag gaactttaca gagggtagtt ggttgcaaga tgttgaatcc 660
tggaaggaat gtgatgatat ctctacttgc gccaataagt atgctaagga gagtataaaa 720
ctagcctgta actggggtta caaagatgtt gaatctggcg aaactctgtc agataaatac 780
ttcaacacaa gaatgccaat tgtcatgaaa cggatagctc agggtggaat ccgtttatcc 840
atgattttga accgagttct tggaagctcc gcagatcatt ctttggcagg aggtcaccat 900
caccatcacc attga 915

<210> SEQ ID NO 5
<211> LENGTH: 717
<212> TYPE: DNA
<213> ORGANISM: Artificial Sequence
<220> FEATURE:
<223> OTHER INFORMATION: This construct was derived by GRAMMR shuffling in accordance with the methodogy of the present invention.

<400> SEQUENCE: 5
atgagtaaag gagaagaact tttcactgga gttgtcccaa ttcttgttga attagatggt 60
gatgttaatg ggcacaaatt ttctgtcagt ggagagggtg aaggtgatgc aacatacgga 120
aaacttaccc ttaaatttat ttgcactact ggaaaactac ctgttccatg gccaacactt 180
gtcactactt tctcttatgg tgttcaatgc ttttcaagat acccagatca tatgaaacgg 240
catgactttt tcaagagtgc catgcccgaa ggttatgtac aggaacgcac tatatttttc 300
aaggatgacg ggaactacaa gacacgtgct gaagtcaagt ttgaaggtga tacccttgtt 360
aatagaatcg agttaaaagg tattgatttt aaagaagatg gaaacattct tggacacaaa 420
ttggaataca actataactc acacaatgta tacatcatgg cagacaaaca aaagaatgga 480
atcaaagtta acttcaaaat tagacacaac attgaagatg gaagcgttca actagcagac 540
cattatcaac aaaatactcc aattggcgat ggccctgtcc ttttaccaga caaccattac 600
ctgtccacac aatctgccct ttcgaaagat cccaacgaaa agagagacca catggtcctt 660
cttgagtttg taacagctgc tgggattaca catggcatgg atgaactata caaataa 717

<210> SEQ ID NO 6
<211> LENGTH: 717
<212> TYPE: DNA
<213> ORGANISM: Artificial Sequence
<220> FEATURE:
<223> OTHER INFORMATION: This construct was derived by GRAMMR shuffling in accordance with the methodogy of the present invention.

-continued

<400> SEQUENCE: 6

```
atgagtaaag gagaagaact tttcactgga gttgtcccaa ttcttgttga attagatggt     60
gatgttaatg ggcacaaatt ttctgtcagt ggagagggtg aaggtgatgc tacatacgga    120
aagcttaccc ttaaatttat ttgcactact ggaaaactac ctgttccatg gccaacactt    180
gtcactactt tctcttatgg tgttcaatgc ttttcaagat acccagatca tatgaaacgg    240
catgactttt tcaagagtgc catgcccgaa ggttatgtac aggaacgcac tatatctttc    300
aaagatgacg ggaactacaa gacacgtgct gaagtcaagt ttgaaggtga tacccttgtt    360
aatagaatcg agttaaaagg tattgatttt aaagaagatg gaaacattct tggacacaaa    420
ctcgagtaca actataactc acacaatgta tacatcatgg cagacaaaca aaagaatgga    480
atcaaagtta acttcaaaat tagacacaac attgaagatg gaagcgttca actagcagac    540
cattatcaac aaaatactcc aattggcgat ggccctgtcc ttttaccaga caaccattac    600
ctgtccacac aatctgccct ttcgaaagat cccaacgaaa agagagacca catggtcctt    660
cttgagtttg taacagctgc tgggattaca catggcatgg atgaactata caaataa       717
```

<210> SEQ ID NO 7
<211> LENGTH: 717
<212> TYPE: DNA
<213> ORGANISM: Artificial Sequence
<220> FEATURE:
<223> OTHER INFORMATION: This construct was derived by GRAMMR shuffling in accordance with the methodogy of the present invention.

<400> SEQUENCE: 7

```
atgagtaaag gagaagaact tttcactgga gttgtcccaa ttcttgttga attagatggt     60
gatgttaatg ggcacaaatt ttctgtcagt ggagagggtg aaggtgatgc tacatacgga    120
aagcttaccc ttaaatttat ttgcactact ggaaaactac ctgttccatg gccaacactt    180
gtcactactt tctcttatgg tgttcaatgc ttttcccgtt atccggatca tatgaaacgg    240
catgactttt tcaagagtgc catgcccgaa ggttatgtac aggaacgcac tatatctttc    300
aaagatgacg ggaactacaa gacgcgtgct gaagtcaagt ttgaaggtga tacccttgtt    360
aatagaatcg agttaaaagg tattgatttt aaagaagatg gaaacattct cggacacaaa    420
ttggaataca actataactc acacaatgta tacatcacgg cagacaaaca aaagaatgga    480
atcaaagcta acttcaaaat tcgccacaac attgaagatg gatccgttca actagcagac    540
cattatcaac aaaatactcc aattggcgat ggccctgtcc ttttaccaga caaccattac    600
ctgtcgacac aatctgccct ttcgaaagat cccaacgaaa agcgtgacca catggtcctt    660
cttgagtttg taactgctgc tgggattaca catggcatgg atgaactata caaataa       717
```

<210> SEQ ID NO 8
<211> LENGTH: 717
<212> TYPE: DNA
<213> ORGANISM: Artificial Sequence
<220> FEATURE:
<223> OTHER INFORMATION: This construct was derived by GRAMMR shuffling in accordance with the methodogy of the present invention

<400> SEQUENCE: 8

```
atgagtaaag gagaagaact tttcactgga gttgtcccaa ttcttgttga attagatggt     60
gatgttaatg ggcacaaatt ttctgtcagt ggagagggtg aaggtgatgc aacatacgga    120
aaacttaccc ttaaatttat ttgcactact ggaaaactac ctgttccatg gccaacactt    180
```

-continued

```
gtcactactt tctcttatgg tgttcaatgc ttttcaagat acccagatca tatgaaacgg    240

catgactttt tcaagagtgc catgcccgaa ggttatgtac aggaaagaac tatatttttc    300

aaggatgacg ggaactacaa gacacgtgct gaagtcaagt ttgaaggtga tacccttgtt    360

aatagaatcg agttaaaagg tattgatttt aaagaagatg gaaacattct cggacacaaa    420

ctcgagtaca actataactc acacaatgta tacatcatgg cagacaaaca aaagaatgga    480

atcaaagtta acttcaaaat tcgccacaac attgaagatg gatccgttca actagcagac    540

cattatcaac aaaatactcc aattggcgat ggccctgtcc ttttaccaga caaccattac    600

ctgtccacac aatctgccct ttcgaaagat cccaacgaaa agagagacca catggtcctt    660

cttgagtttg taacagctgc tgggattaca catggcatgg atgaactata caaataa       717
```

<210> SEQ ID NO 9
<211> LENGTH: 807
<212> TYPE: DNA
<213> ORGANISM: Tobacco mosaic virus

<400> SEQUENCE: 9

```
atggctctag ttgttaaagg aaaagtgaat atcaatgagt ttatcgacct gacaaaaatg     60

gagaagatct taccgtcgat gtttacccct gtaaagagtg ttatgtgttc caaagttgat    120

aaaataatgg ttcatgagaa tgagtcattg tcaggggtga accttcttaa aggagttaag    180

cttattgata gtggatacgt ctgtttagcc ggtttggtcg tcacgggcga gtggaacttg    240

cctgacaatt gcagaggagg tgtgagcgtg tgtctggtgg acaaaaggat ggaaagagcc    300

gacgaggcca ctctcggatc ttactacaca gcagctgcaa agaaaagatt tcagttcaag    360

gtcgttccca attatgctat aaccacccag gacgcgatga aaaacgtctg gcaagtttta    420

gttaatatta gaaatgtgaa gatgtcagcg ggtttctgtc cgctttctct ggagtttgtg    480

tcggtgtgta ttgtttatag aaataatata aaattaggtt tgagagagaa gattacaaac    540

gtgagagacg gagggcccat ggaacttaca gaagaagtcg ttgatgagtt catggaagat    600

gtccctatgt cgatcaggct tgcaaagttt cgatctcgaa ccggaaaaaa gagtgatgtc    660

cgcaaaggga aaaatagtag tagtgatcgg tcagtgccga acaagaacta tagaaatgtt    720

aaggattttg gaggaatgag ttttaaaaag aataatttaa tcgatgatga ttcggaggct    780

actgtcgccg aatcggattc gttttaa                                        807
```

<210> SEQ ID NO 10
<211> LENGTH: 793
<212> TYPE: DNA
<213> ORGANISM: Tomato mosaic virus

<400> SEQUENCE: 10

```
atggctctag ttgttaaagg taaggtaaat attaatgagt ttatcgatct gtcaaagtct     60

gagaaacttc tcccgtcgat gttcacgcct gtaaagagtg ttatggtttc aaaggttgat    120

aagattatgg tccatgaaaa tgaatcattg tctgaagtaa atctcttaaa aggtgtaaaa    180

cttatagaag gtgggtatgt ttgcttagtt ggtcttgttg tgtccggtga gtggaattta    240

ccagataatt gccgtggtgg tgtgagtgtc tgcatggttg acaagagaat ggaaagagcg    300

gacgaagcca cactggggtc atattacact gctgctgcta aaaagcggtt tcagtttaaa    360

gtggtcccaa attacggtat tactacaaag gatgcagaaa agaacatatg gcaggtctta    420

gtaaatatta aaaatgtaaa aatgagtgcg ggctactgcc ctttgtcatt agaatttgtg    480

tctgtgtgta ttgtttataa aaataatata aaattgggtt tgagggagaa agtaacgagt    540
```

-continued

```
gtgaacgatg gaggacccat ggaactttca gaagaagttg ttgatgagtt catggagaat    600

gttccaatgt cggttagact cgcaaagttt cgaaccaaat cctcaaaaag aggtccgaaa    660

aataataata atttaggtaa ggggcgttca ggcggaaggc ctaaaccaaa aagttttgat    720

gaagttgaaa aagagtttga taatttgatt gaagatgaag ccgagacgtc ggtcgcggat    780

tctgattcgt att                                                       793


<210> SEQ ID NO 11
<211> LENGTH: 795
<212> TYPE: DNA
<213> ORGANISM: Artificial Sequence
<220> FEATURE:
<223> OTHER INFORMATION: This construct was derived by GRAMMR shuffling
      in accordance with the methodogy of the present invention

<400> SEQUENCE: 11

atggctctag ttgttaaagg taaggtaaat attaatgagt ctatcgatct gtcaaagtct     60

gagaaacttc tcccgtcgat gttcacgcct gtaaagagtg ttatggtttc aaaggttgat    120

aagattatgg tccatgaaaa tgaatcattg tctgaagtaa atctcttaaa aggtgtaaaa    180

cttatagaag gtgggtatgt ttgcttagtt ggtcttgttg tgtccggtga gtggaattta    240

ccagataatt gccgtggtgg tgtgagtgtc tgcatggttg acaagagaat ggaaagagcg    300

gacgaagcca cactggggtc atattacact gctgctgcta aaaagcggtt tcagttcaag    360

gtcgttccca attatgctat aaccacccag gatgcagaaa agaacatatg gcaggtctta    420

gtaaatatta aaaatgtaaa aatgagtgcg ggctactacc ctttgtcatt agaatttgtg    480

tctgtgtgta ttgtttataa aaataatata aaattgggtt tgagggagaa agtaacgagt    540

gtgaacgatg gaggacccat ggaactttca gaagaagttg ttgatgagtt catggagaat    600

gttccaatgt cgatcaggct tgcaaagttt cgaaccaaat cctcaaaaag aggtccgaaa    660

aataataata atttaggtaa ggggcgttca ggcggaaggc ctaaaccaag aagttttgat    720

gaagttgaaa aagagtttga taatttgatt gaagatgaag ccgagacgtc ggtcgcggat    780

tctgattcgt attaa                                                     795


<210> SEQ ID NO 12
<211> LENGTH: 795
<212> TYPE: DNA
<213> ORGANISM: Artificial Sequence
<220> FEATURE:
<223> OTHER INFORMATION: This construct was derived by GRAMMR shuffling
      in accordance with the methodogy of the present invention.

<400> SEQUENCE: 12

atggctctag ttgttaaagg taaggtaaat attaatgagt ttatcgatct gtcaaagtct     60

gagaaacttc tcccgtcgat gttcacgcct gtaaagagtg ttatggtttc aaaggttgat    120

aagattatgg tccatgaaaa tgaatcattg tctgaagtaa atctcttaaa aggtgtaaaa    180

cttatagaag gtgggtatgt ttgcttagtt ggtcttgttg tgtccggtgt gtggaattta    240

ccagataatt gccgtggtgg tgtgagtgtc tgcatggttg acaagagaat ggaaagagcg    300

gacgaggcca cactcggatc ttactacact gctgctgcta aaaagcggtt tcagttcaag    360

gtcgttccca attatgctat aaccacccag gatgcagaaa agaacatatg gcaggtctta    420

gtaaatatta aaaatgtaaa aatgagtgcg ggctactgcc ctttgtcatt agaatttgtg    480

tctgtgtgta ttgtttataa aaataatata aaattgggtt tgagggagaa agtaacgagt    540
```

-continued

```
gtgaacgatg gaggacccat ggaactttca gaagaagttg ttgatgagtt catggagaat    600

gttccaatgt cggttagact cgcaaagttt cgaaccaaat cctcaaaaag aggtccgaaa    660

aataataata atttaggtaa ggggcgttca ggcggaaggc ctaaaccaaa aagttttgat    720

gaagttggaa aagagtttga taatttgatt gaagatgaag ccgagacgtc ggtcgcggat    780

tctgattcgt attaa                                                     795
```

<210> SEQ ID NO 13
<211> LENGTH: 795
<212> TYPE: DNA
<213> ORGANISM: Artificial Sequence
<220> FEATURE:
<223> OTHER INFORMATION: This construct was derived by GRAMMR shuffling in accordance with the methodogy of the present invention.

<400> SEQUENCE: 13

```
atggctctag ttgttaaagg taaggtaaat attaatgagt ttatcgatct gtcaaagtct     60

gagaaacttc tcccgtcgat gttcacgcct gtaaggagtg ttatggtttc aaaggttgat    120

aagattatgg tccatgaaaa tgaatcattg tctgaagtaa atctcttaaa aggtgtaaaa    180

cttatagaag gtgggtatgt ttgcttagtt ggtcttgttg tgtccggtga gtggaattta    240

ccagataatt gccgtggtgg tgtgagtgtc tgcatggttg acaagagaat ggaaagagcg    300

gacgaagcca cactggggtc atattacact gctgctgcta aaaagcggtt tcagtttaaa    360

gtggtcccaa attacggtat tactacccag gacgcgatga aaaacgtctg gcaggtctta    420

gtaaatatta aaaatgtaaa aatgagtgcg ggctactgcc ctttgtcatt agaatttgtg    480

tctgtgtgta ttgtttataa aaataatata aaattgggtt tgagggagaa agtaacgagt    540

gtgaacgatg gaggacccat ggaactttca gaagaagttg ttgatgagtt catggagaat    600

gttccaatgt cgatcagact cgcaaagttt cgaaccaaat cctcaaaaag aggtccgaaa    660

aataataata atttaggtaa ggggcgttca ggcggaaggc ctaaaccaaa aagttttgat    720

gaagttgaaa aagagtttga taatttgatt gaagatgaag ccgagacgtc ggtcgcggat    780

tctgattcgt attaa                                                     795
```

<210> SEQ ID NO 14
<211> LENGTH: 796
<212> TYPE: DNA
<213> ORGANISM: Artificial Sequence
<220> FEATURE:
<223> OTHER INFORMATION: This construct was derived by GRAMMR shuffling in accordance with the methodogy of the present invention.

<400> SEQUENCE: 14

```
atggctctag ttgttaaagg taaggtaaat attaatgagt ttatcgatct gtcaaagtct     60

gagaaacttc tcccgtcgat gttcacgcct gtaaagagtg ttatggtttc aaaggttgat    120

aagattatgg tccatgaaaa tgaatcattg tctgaagtaa atctcttaaa aggtgttaag    180

cttattgata gtggatacgt ctgtttagcc ggtttggtcg tcacgggcga gtggaattta    240

ccagataatt gccgtggtgg tgtgagtgtc tgcatggttg acaagagaat ggaaagagcg    300

gacgaagcca cactggggtc atattacact gctgctgcta aaaagcggtt tcagttcaag    360

gtcgttccca aattacggta ttactaccca ggatgcagaa aagaacatat ggcaggtctt    420

agtaaatatt aaaaatgtaa aaatgagtgc gggctactgc ccgctttctc tggagtttgt    480

gtctgtgtgt attgtttata aaaataatat aaaattgggt ttgagggaga aagtaacgag    540

tgtgaacgat ggaggaccca tggaactttc agaagaagtt gttgatgagt tcatggagaa    600
```

-continued

```
tgttccaatg tcggttagac tcgcaaagtt tcgaaccaaa tcctcaaaaa gaggtccgaa    660

aaataataat aatttaggta aggggcgttc aggcggaagg cctaaaccaa aaagttttga    720

tgaagttgaa aaagagtttg ataatttgat tgaggatgat tcggaggcta ctgtcgccga    780

ttctgattcg tattaa                                                    796


<210> SEQ ID NO 15
<211> LENGTH: 795
<212> TYPE: DNA
<213> ORGANISM: Artificial Sequence
<220> FEATURE:
<223> OTHER INFORMATION: This construct was derived by GRAMMR shuffling
      in accordance with the methodogy of the present invention.

<400> SEQUENCE: 15

atggctctag ttgttaaagg aaaagtgaat attaatgagt ttatcgatct gtcaaagtct     60

gagaaacttc tcccgtcgat gttcacgcct gtaaagagtg ttatggtttc aaaggttgat    120

aagattatgg tccatgaaaa tgaatcattg tctgaagtaa atctcttaaa aggtgtaaaa    180

cttatagaag gtgggtatgt ttgcttagtt ggtcttgttg tgtccggcga gtggaattta    240

ccagataatt gccgtggtgg tgtgagtgtc tgcatggttg acaagagaat ggaaagagcg    300

gacgaagcca cactggggtc atattacact gctgctgcaa agaaaagatt tcagttcaag    360

gtcgttccca attatgctat aaccacccag gatgcagaaa agaacatatg gcgggtctta    420

gtaaatatta aaaatgtaaa aatgagtgcg ggctactgcc cgctttctct ggagtttgtg    480

tctgtgtgta ttgtttataa aaataatata aaattgggtt tgagggagaa agtaacgagt    540

gtgaacgatg aaggacccat ggaactttca gaagaagttg ttgatgagtt catggagaat    600

gttccaatgt cgatcaggct cgcaaagttt cgaaccaaat cctcaaaaag aggtccgaaa    660

aataataata atttaggtaa ggggcgttca ggcggaaggc ctaaaccaaa aagttttgat    720

gaagttgaaa aagagtttga taatttgatt gaagatgaag ccgagacgtc ggtcgcggat    780

tctgattcgt actaa                                                     795


<210> SEQ ID NO 16
<211> LENGTH: 888
<212> TYPE: DNA
<213> ORGANISM: Selaginella lepidophylla

<400> SEQUENCE: 16

atggcaacga ccaagacgag cgggatggcg ctggctttgc tcctcgtcgc cgccctggcc     60

gtgggagctg cggcctgggg gaaagagggc catcgcctca cttgtatggt cgccgagccc    120

tttctaagct ctgaatccaa gcaagctgtg gaggagcttc tctctggaag agatctcccg    180

gacttgtgtt catgggccga tcagattcga agatcgtata agtttagatg gactggtcct    240

ttgcactaca tcgatactcc agacaacctc tgcacctatg actatgatcg tgactgccac    300

gattcccatg ggaagaagga cgtgtgtgtc gctggtggga tcaacaatta ctcgtcgcag    360

ctggaaacgt ttctagattc agagagctcg tcgtataact tgaccgaggc gctgctcttc    420

ctggctcact ttgtcgggga tatacaccag cccttgcacg tagcatttac gagtgatgcc    480

ggaggcaatg gcgtgcacgt ccgctggttt ggacgaaagg ccaacttgca tcacgtctgg    540

gatacagaat ttatttctag agccaatcgt gtgtactacc acgacatttc caagatgctc    600

cggaacatta ccaggagcat aactaagaag aatttcaata gttggagcag atgtaagact    660

gatccggcgg cttgtattga tagttatgcg acagaaagta tagatgcttc ttgcaactgg    720
```

-continued

```
gcatacaaag acgcacccga cggaagctct ctagatgatg attacttctc ttcacgcctt    780

ccaattgttg agcagcgtct tgctcaaggg ggcgtcaggc tggcgtcaat actcaacagg    840

atttttggag gagcaaagtc gaacaggtcc agtcgctcaa gcatgtag                 888
```

<210> SEQ ID NO 17
<211> LENGTH: 3637
<212> TYPE: DNA
<213> ORGANISM: Artificial Sequence
<220> FEATURE:
<223> OTHER INFORMATION: Encodes cycle 3 GFP

<400> SEQUENCE: 17

```
gtggcacttt tcggggaaat gtgcgcggaa cccctatttg tttatttttc taaatacatt     60

caaatatgta tccgctcatg agacaataac cctgataaat gcttcaataa tattgaaaaa    120

ggaagagtat gagtattcaa catttccgtg tcgcccttat tccctttttt gcggcatttt    180

gccttcctgt ttttgctcac ccagaaacgc tggtgaaagt aaaagatgct gaagatcagt    240

tgggtgcacg agtgggttac atcgaactgg atctcaacag cggtaagatc cttgagagtt    300

ttcgccccga agaacgtttt ccaatgatga gcacttttaa agttctgcta tgtggcgcgg    360

tattatcccg tattgacgcc gggcaagagc aactcggtcg ccgcatacac tattctcaga    420

atgacttggt tgagtactca ccagtcacag aaaagcatct tacggatggc atgacagtaa    480

gagaattatg cagtgctgcc ataaccatga gtgataacac tgcggccaac ttacttctga    540

caacgatcgg aggaccgaag gagctaaccg cttttttgca caacatgggg gatcatgtaa    600

ctcgccttga tcgttgggaa ccggagctga atgaagccat accaaacgac gagcgtgaca    660

ccacgatgcc tgtagcaatg gcaacaacgt tgcgcaaact attaactggc gaactactta    720

ctctagcttc ccggcaacaa ttaatagact ggatggaggc ggataaagtt gcaggaccac    780

ttctgcgctc ggcccttccg gctggctggt ttattgctga taaatctgga gccggtgagc    840

gtgggtctcg cggtatcatt gcagcactgg ggccagatgg taagccctcc cgtatcgtag    900

ttatctacac gacggggagt caggcaacta tggatgaacg aaatagacag atcgctgaga    960

taggtgcctc actgattaag cattggtaac tgtcagacca agtttactca tatatacttt   1020

agattgattt aaaacttcat ttttaattta aaaggatcta ggtgaagatc ctttttgata   1080

atctcatgac caaaatccct taacgtgagt tttcgttcca ctgagcgtca gaccccgtag   1140

aaaagatcaa aggatcttct tgagatcctt tttttctgcg cgtaatctgc tgcttgcaaa   1200

caaaaaaacc accgctacca gcggtggttt gtttgccgga tcaagagcta ccaactcttt   1260

ttccgaaggt aactggcttc agcagagcgc agataccaaa tactgtcctt ctagtgtagc   1320

cgtagttagg ccaccacttc aagaactctg tagcaccgcc tacatacctc gctctgctaa   1380

tcctgttacc agtggctgct gccagtggcg ataagtcgtg tcttaccggg ttggactcaa   1440

gacgatagtt accggataag gcgcagcggt cgggctgaac ggggggttcg tgcacacagc   1500

ccagcttgga gcgaacgacc tacaccgaac tgagatacct acagcgtgag ctatgagaaa   1560

gcgccacgct tcccgaaggg agaaaggcgg acaggtatcc ggtaagcggc agggtcggaa   1620

caggagagcg cacgagggag cttccagggg gaaacgcctg gtatctttat agtcctgtcg   1680

ggtttcgcca cctctgactt gagcgtcgat ttttgtgatg ctcgtcaggg gggcggagcc   1740

tatggaaaaa cgccagcaac gcggcctttt tacggttcct ggccttttgc tggccttttg   1800

ctcacatgtt ctttcctgcg ttatcccctg attctgtgga taaccgtatt accgcctttg   1860
```

-continued agtgagctga taccgctcgc cgcagccgaa cgaccgagcg cagcgagtca gtgagcgagg 1920
aagcggaaga gcgcccaata cgcaaaccgc ctctccccgc gcgttggccg attcattaat 1980
gcagctggca cgacaggttt cccgactgga aagcgggcag tgagcgcaac gcaattaatg 2040
tgagttagct cactcattag gcaccccagg ctttacactt tatgcttccg gctcgtatgt 2100
tgtgtggaat tgtgagcgga taacaatttc acacaggaaa cagctatgac catgattacg 2160
ccaagcgcgc aattaaccct cactaaaggg aacaaaagct gggtaccgat gagtaaagga 2220
gaagaacttt tcactggagt tgtcccaatt cttgttgaat tagatggtga tgttaatggg 2280
cacaaatttt ctgtcagtgg agagggtgaa ggtgatgcta catacggaaa gcttaccctt 2340
aaatttattt gcactactgg aaaactacct gttccatggc caacacttgt cactactttc 2400
tcttatggtg ttcaatgctt ttcccgttat ccggatcata tgaaacggca tgactttttc 2460
aagagtgcca tgcccgaagg ttatgtacag gaacgcacta tatctttcaa agatgacggg 2520
aactacaaga cgcgtgctga agtcaagttt gaaggtgata cccttgttaa tcgtatcgag 2580
ttaaaaggta ttgattttaa agaagatgga aacattctcg gacacaaact cgagtacaac 2640
tataactcac acaatgtata catcacggca gacaaacaaa agaatggaat caaagctaac 2700
ttcaaaattc gccacaacat tgaagatgga tccgttcaac tagcagacca ttatcaacaa 2760
aatactccaa ttggcgatgg ccctgtcctt ttaccagaca accattacct gtcgacacaa 2820
tctgcccttt cgaaagatcc caacgaaaag cgtgaccaca tggtccttct tgagtttgta 2880
actgctgctg ggattacaca tggcatggat gaactataca aataagaatt cctgcagccc 2940
gggggatcca ctagttctag agcggccgcc accgcggtgg agctccaatt cgccctatag 3000
tgagtcgtat tacgcgcgct cactggccgt cgttttacaa cgtcgtgact gggaaaaccc 3060
tggcgttacc caacttaatc gccttgcagc acatccccct ttcgccagct ggcgtaatag 3120
cgaagaggcc cgcaccgatc gcccttccca acagttgcgc agcctgaatg gcgaatggga 3180
cgcgccctgt agcggcgcat taagcgcggc gggtgtggtg gttacgcgca gcgtgaccgc 3240
tacacttgcc agcgccctag cgcccgctcc tttcgctttc ttcccttcct ttctcgccac 3300
gttcgccggc tttccccgtc aagctctaaa tcgggggctc cctttagggt tccgatttag 3360
tgctttacgg cacctcgacc ccaaaaaact tgattagggt gatggttcac gtagtgggcc 3420
atcgccctga tagacggttt ttcgcccttt gacgttggag tccacgttct ttaatagtgg 3480
actcttgttc caaactggaa caacactcaa ccctatctcg gtctattctt ttgatttata 3540
agggattttg ccgatttcgg cctattggtt aaaaaatgag ctgatttaac aaaaatttaa 3600
cgcgaatttt aacaaaatat taacgcttac aatttag 3637

<210> SEQ ID NO 18
<211> LENGTH: 796
<212> TYPE: DNA
<213> ORGANISM: Tobamovirus Cg

<400> SEQUENCE: 18
atgtcttacg agcctaaagt gagcgacttc cttgctctta cgaaaaagga ggaaatttta 60
cccaaggctc ttacgaggtt aaagactgtc tctattagta ctaaggatgt tatatctgtt 120
aaggattctg agtccctgtg tgatatagat ttactagtta atgtgccatt agataagtat 180
agatatgtgg gtgttttagg tgttgttttt accggtgagt ggttagtgcc ggatttcgtt 240
aaaggtggag taacagtgag cgtgattgac aaacggcttg agaactccaa agagtgcata 300
attggtacgt acagagctgc tgcgaaagac aaaaggttcc agttcaagct ggttccaaat 360

-continued

```
tacttcgtgt ctgttgcaga tgccaagcga aaaccgtggc aagttcatgt gcgtattcaa    420

aatttaagga ttgaagctgg atggcaacct ctggccttag aggtggtttc tgttgctatg    480

gtcactaata acgtggttgt taagggtttg agagaaaagg tcatcgcagt gaatgatccg    540

aatgtcgaag gtttcgaagg cgtggttgac gatttcgtcg attcggtcgc agcattcaag    600

gcggttgaca ctttcagaaa gaaaaagaaa aggattggag gaaaggatgt aaataataat    660

aagtttagat atagaccgga gagatacgcc ggtcaggatt cgttaaatta taaagaagaa    720

aacgtcttac aacatcacga actcgaatca gtaccagtat ttcgcagcga cgtgggcaga    780

gcccacagcg atgctt                                                    796
```

<210> SEQ ID NO 19
<211> LENGTH: 823
<212> TYPE: DNA
<213> ORGANISM: Tobamovirus Ob

<400> SEQUENCE: 19

```
atgtcaaagg ctattgtcaa gatcgatgaa ttcattaaat tatccaagtc tgaagaggtt     60

ttaccttctg cattcacaag aatgaagtcg gtcagagtct caacagtgga taagataatg    120

gccaaagaga atgacaatat ttccgaagta gatttactta agggtgttaa gttagttaaa    180

aatggttatg tttgtttagt aggtcttgtg gtgtcaggag agtggaattt acccgacaac    240

tgcagaggtg gtgtaagtat ctgtctgata gacaaacgta tgcaacgtca taacgaagct    300

actttaggtt cgtacactac caaagccagc aagaaaaact tttcgttcaa gcttataccg    360

aattactcga taacctctca agatgctgaa aggcgtcctt gggaagttat ggtaaatatt    420

cgtggtgtgg ctatgtccga aggttggtgt ccattatcct tagagttcgt ttctgtttgt    480

attgttcata aaaacaatgt tagaaagggt ctaagagaga aggtgactgc cgtgtccgaa    540

gacgacgcta tagaactcac agaagaggtt gttgatgagt ttatagaagc cgtaccgatg    600

gcgcgacgtt tgcagaactt gagaaaaccc aagtacaaca aagaaaaaga aaataaaaat    660

ttgaataata aaaatagtat aggagtttcc aaacctgtcg gtttggaaag aaataaagta    720

aggagtgtag ttagaaaagg ggttaggagt gatagtagtt taggtgtgac tgatatgagt    780

caggacggta gctcaagcga gatatcatcc gattcgttta ttt                      823
```

<210> SEQ ID NO 20
<211> LENGTH: 769
<212> TYPE: DNA
<213> ORGANISM: Tobacco mosaic virus-U2

<400> SEQUENCE: 20

```
atggctgtta gtctcagaga tactgtcaaa attagcgagt tcattgatct ttcgaaacag     60

gatgagatac ttccggcatt catgactaag gtcaagagcg tcagaatatc gactgtggac    120

aagattatgg ctgttaagaa tgatagtctt tctgatgtag atttacttaa aggtgttaag    180

ttagttaaga atgggtacgt gtgcttagct ggtttggtag tgtctgggga gtggaatctc    240

ccggacaact gccgtggtgg tgtcagtgtt tgtattgtag ataagagaat gaaaaggagt    300

aaggaggcaa cgctgggtgc gtatcacgcc cctgcttgca aaaagaattt ttcctttaag    360

ctaatcccta attattcaat aacatccgag gatgctgaga agcacccatg gcaagtatta    420

gtgaatatca aaggagtggc tatggaagaa ggatactgtc ctttatcttt ggagttcgtt    480

tcaatttgtg tagtacataa aaataatgta agaaaaggtt tgagggaacg tattttgaga    540
```

-continued

```
gtaacagacg gctcgccaat tgaactcact gaaaaagttg ttgaggagtt catagatgaa    600

gtaccaatgg ctgtgaaact cgaaaggttc cggaaaacaa aaaagagagt ggtaggtaat    660

agtgttaata ataagaaaat aaataatagt ggtaagaaag gtttgaaagt tgaggaaatt    720

gaggataatg taagtgatga cgagtctatc gcgtcatcga gtacgtttt                769


<210> SEQ ID NO 21
<211> LENGTH: 808
<212> TYPE: DNA
<213> ORGANISM: Artificial Sequence
<220> FEATURE:
<223> OTHER INFORMATION: This construct was derived by GRAMMR shuffling
      in accordance with the methodogy of the present invention.

<400> SEQUENCE: 21

atggctctag ttgttaaagg taaggtaaat attaatgagt ttatcgatct gtcaaagtct     60

gagaaacttc tcccgtcgat gttcacgcct gtaaagagtg ttatggtttc aaaggttgat    120

aagattatgg tccatgaaaa tgaatcattg tctgaagtaa atctcttaaa aggtgtaaaa    180

cttatagaag gtgggtatgt ttgcttagtt ggtcttgttg tgtccggtga gtggaattta    240

ccagataatt gccgtggtgg tgtgagtgtc tgcatggttg acaagagaat ggaaagagcg    300

gacgaagcca cactggggtc atattacact gctgctgcta aaaagcggtt tcagtttaaa    360

gtggtcccaa attacggtat tactacaaag gatgcagaaa agaacatatg gcaagttcat    420

gtgcgtattc aaaatttaag gattgaagct ggatggcaac ctctggcctt agaggtggtt    480

tctgttgcta tggtcactaa taacgtggtt gttaagggtt tgagagaaaa ggtcatcgca    540

gtgaatgatc cgaatgtcga aggtttcgaa ggcgtggttg acgatttcgt cgattcggtc    600

gcagcattca aggcggttga cactttcaga aagaaaaaga aaaggattgg aggaaaggat    660

gtaaataata ataagtttag atatagaccg gagagatacg ccggtcagga ttcgttaaat    720

tataaagaag aaaacgtctt acaacatcac gaactcgaat cagtaccagt atttcgcagc    780

gacgtgggca gagcccacag cgatgctt                                       808


<210> SEQ ID NO 22
<211> LENGTH: 799
<212> TYPE: DNA
<213> ORGANISM: Artificial Sequence
<220> FEATURE:
<223> OTHER INFORMATION: This construct was derived by GRAMMR shuffling
      in accordance with the methodogy of the present invention.

<400> SEQUENCE: 22

atgtcttacg agcctaaagt gagcgacttc cttgctctta cgaaaaagga ggaaatttta     60

cccaaggctc ttacgaggtt aaagactgtc tctattagta ctaaggatgt tatatctgtt    120

aaggattctg agtccctgtg tgatatagat ttactagtta atgtgccatt agataagtat    180

agatatgtgg gtgttttagg tgttgttttt accggtgagt ggaatttacc agataattgc    240

cgtggtggtg tgagtgtctg catggttgac aagagaatgg aaagagcgga cgaagccaca    300

ctggggtcat attacactgc tgctgcgaaa gacaaaaggt tccagttcaa gctggttcca    360

aattacttcg tgtctgttgc agatgccaag cgaaaaccgt ggcaagttca tgtgcgtatt    420

caaaatttaa ggattgaagc tggatggcaa cctctggcct tagaggtggt ttctgttgct    480

atggtcacta ataacgtggt tgttaagggt ttgagagaaa aggtcatcgc agtgaatgat    540

ccgaatgtcg aaggtttcga aggcgtggtt gacgatttcg tcgattcggt cgcagcattc    600

aaggcggttg acactttcag aaagaaaaag aaaaggattg gaggaaagga tgtaaataat    660
```

-continued

```
aataagttta gatatagacc ggagagatac gccggtcagg attcgttaaa ttataaagaa    720

gaaaacgtct tacaacatca cgaactcgaa tcagtaccag tatttcgcag cgacgtgggc    780

agagcccaca gcgatgctt                                                 799
```

<210> SEQ ID NO 23
<211> LENGTH: 823
<212> TYPE: DNA
<213> ORGANISM: Artificial Sequence
<220> FEATURE:
<223> OTHER INFORMATION: This construct was derived by GRAMMR shuffling in accordance with the methodogy of the present invention.

<400> SEQUENCE: 23

```
aaataaacga atcggatgat atctcgcttg agctaccgtc ctgactcata tcagtcacac     60

ctaaactact atcactccta accccttttc taactacact ccttacttta tttctttcca    120

aaccgacagg tttggaaact cctatactat ttttattatt caaattttta ttttcttttt    180

ctttgttgta cttgggtttt ctcaagttct gcaaacgtcg cgccatcggt acggcttcta    240

taaactcatc aacaacctct tctgtgagtt ctatagcgtc gtcttcggac acggcagtca    300

ccttctctct tagacccttt ctaacattgt ttttatgaac aatacaaaca gaaacgaact    360

ctaaggataa tggacaccaa ccttcggaca tagccacacc acgaatattt accataactt    420

cccaaggacg cctttcagca tcttgagagg ttatcgagta attcggtata agcttgaacg    480

aaaagttttt cttgctggct ttggtagtgt acgaacctaa agtagcttcg ttatgacgtt    540

gcatacgttt gtctatcaga cagatactta caccacctct gcagttgtcg ggtaaattcc    600

actctcctga caccacaaga cctactaaac aaacataacc accttctata agttttacac    660

cttttaagag atttacttca gacaatgatt cattctcttt ggccattatc ttatccactg    720

ttgagactct gaccgacttc attcttgtga atgcagaagg taaaacctct tcagacttgg    780

ataatttaat gaattcatcg atcttgacaa tagcctttga cat                      823
```

<210> SEQ ID NO 24
<211> LENGTH: 792
<212> TYPE: DNA
<213> ORGANISM: Artificial Sequence
<220> FEATURE:
<223> OTHER INFORMATION: This construct was derived by GRAMMR shuffling in accordance with the methodogy of the present invention.

<400> SEQUENCE: 24

```
aatacgaatc agaatccgcg accgacgtct cggcttcatc ttcaatcaaa ttatcaaact     60

ctttttcaac ttcatcaaaa ctttttggtt taggccttcc gcctgaacgc cccttaccta    120

aattattatt atttttcgga cctctttttg aggatttggt tcgaaacttt gcgagtctaa    180

ccgacattgg aacattctcc atgaactcat caacaacctc ttctgtgagt tctatagcgt    240

cgtcttcgga cacggcagtc accttctctc ttagaccctt tctaacattg tttttatgaa    300

caatacaaac agaaacgaac tctaatgaca aagggcagta gcccgcactc atttttacat    360

ttttaatatt tactaagacc tgccatatgt tcttttctgc atcctttgta gtaataccgt    420

aatttgggac cactttaaac tgaaaccgct ttttagcagc agcagtgtaa tatgacccca    480

gtgtggcttc gtccgctctt tccattctct tgtcaaccat gcagacactc acaccaccac    540

ggcaattatc tggtaaattc cactctcctg acaccacaag acctactaaa caaacataac    600

catttttaac taacttaaca cccttaagag atttacttcg gacaatgatt cattttcatg    660
```

-continued

```
gaccataatc ttatcaacct ttgaaaccat aacactcttt acaggcgtga atgcagaagg    720

taaaacctct tcagactttg acagatcgat aaactcatta atatttacct tacctttaac    780

aactagagcc at                                                         792


<210> SEQ ID NO 25
<211> LENGTH: 769
<212> TYPE: DNA
<213> ORGANISM: Artificial Sequence
<220> FEATURE:
<223> OTHER INFORMATION: This construct was derived by GRAMMR shuffling
      in accordance with the methodogy of the present invention.

<400> SEQUENCE: 25

aatacgaatc agaatccgcg atagactcgt catcacttac attatcctca atttcctcaa     60

ctttcaaacc tttcttacca ctattattta ttttcttatt attaacacta ttacctacca    120

ctctcttttt tgttttccgg aacctttcga gtttcacagc cattggtact tcatctatga    180

actcatcaac aacttcttct gaaagttcca tgggtcctcc atcgttcaca ctcgttactt    240

tctccctcaa acccaatttt atattatttt tataaacaat acacacagac acaaattcta    300

aagataaagg gcagtatcct tcttccatag ccactccttt gatattcact aatacttgcc    360

atgggtgctt ttctgcatcc tcggatgtta ttgaataatt agggaccact ttaaactgaa    420

accgcttttt agcagcaggg gcgtgatacg cacccagcgt tgcctcctta ctcctttcca    480

ttctcttgtc aaccatgcag acactcacac caccacggca gttgtccggg agattccact    540

caccggacac aacaagacca actaagcaaa catacccacc ttctataagt tttacacctt    600

ttaagagatt tacttcagac aatgattcat tttcatggac cataatctta tcaacctttg    660

aaaccataac actctttaca ggcgtgaaca tcgacgggag aagtttctca gactttgaca    720

gatcgataaa ctcattaata tttaccttac ctttaacaac tagagccat                 769


<210> SEQ ID NO 26
<211> LENGTH: 772
<212> TYPE: DNA
<213> ORGANISM: Artificial Sequence
<220> FEATURE:
<223> OTHER INFORMATION: This construct was derived by GRAMMR shuffling
      in accordance with the methodogy of the present invention.

<400> SEQUENCE: 26

aatacgaatc agaatccgcg accgacgtct cggcttcact tacattatcc tcaatttcct     60

caactttcaa aactttctta ccactattat ttattttctt attattaaca ctattaccta    120

ccactctctt ttttgttttc cggaaccttt cgagtttcac agccattggt acttcatcta    180

tgaactcatc aacaactttt tcagtgagtt caattggcga gccgtctgtt actctcaaaa    240

tacgttccct caaacccaat tttatattat ttttataaac aatacacaca gacacaaatt    300

ctaatgacaa agggcagtag cccgcactca tttttacatt tttaatattt actaagacct    360

gccatgggtg cttctcagca tcctcggatg ttattgaata attagggatt agcttaaagg    420

aaaaattctt tttgcaagca ggggcgtgat acgcacccag tgtggcttcg tccgctcttt    480

ccattctctt gtcaaccatg cagacactca caccaccacg gcagttgtcc gggagattcc    540

actcaccgga cacaacaaga ccaactaagc acacgtaccc attcttaact aacttaacac    600

ctttaagtaa atctacatca gacaatgatt cattttcatg gaccataatc ttatcaacct    660

ttgaaaccat aacactcttt acaggcgtga acatcgacgg gagaagtttc tcagactttg    720

acagatcgat aaactcgcta attttgacag tatctctgag actaacagcc at            772
```

-continued

<210> SEQ ID NO 27
<211> LENGTH: 805
<212> TYPE: DNA
<213> ORGANISM: Artificial Sequence
<220> FEATURE:
<223> OTHER INFORMATION: This construct was derived by GRAMMR shuffling
in accordance with the methodogy of the present invention.

<400> SEQUENCE: 27
atggctctag ttgttaaagg aaaagtgaat attaatgagt ttatcgatct gtcaaagtct 60
gagaaacttc tcccgtcgat gttcacgcct gtaaagagtg ttatggtttc aaaggttgat 120
aagattatgg tccatgaaaa tgaatcattg tctgaagtaa atctcttaaa aggtgtaaaa 180
cttatagaag gtgggtatgt ttgcttagtt ggtcttgttg tgtccggtga gtggaattta 240
ccagataatt gccgtggtgg tgtgagtgtc tgcatggttg acaagagaat ggaaagagcg 300
gacgaagcca ctctcggatc ttactacaca gcagctgcaa agaaaagatt tcagttcaag 360
gtcgttccca attatgctat aaccacccag gacgcgatga aaaacgtctg gcaagtttta 420
gttaatatta gaaatgtgaa gatgtcagcg ggtttctgtc cgctttctct ggagtttgtg 480
tctgtgtgta ttgtttataa aaataatata aaattgggtt tgagggagaa agtaacgagt 540
gtgaacgatg gaggacccat ggaactttca gaagaagttg ttgatgagtt catggaagat 600
gtcccaatgt cggttagact cgcaaagttt cgatctcgaa ccggaaaaaa gagtgatgtc 660
cgcaaaggga aaaatagtag tagtgatcgg tcagtgccga acaagaacta tagaaatgtt 720
aaggattttg gaggaatgag ttttaaaaag aataatttaa tcgatgatga ttcggagacg 780
tcggtcgcgg attctgattc gtatt 805

<210> SEQ ID NO 28
<211> LENGTH: 804
<212> TYPE: DNA
<213> ORGANISM: Artificial Sequence
<220> FEATURE:
<223> OTHER INFORMATION: This construct was derived by GRAMMR shuffling
in accordance with the methodogy of the present invention.

<400> SEQUENCE: 28
atggctctag ttgttaaagg aaaagtgaat atcaatgagt ttatcgacct gacaaagtct 60
gagaaacttc tcccgtcgat gtttacccct gtaaagagtg ttatggttcc aaagttgata 120
agattatggt tcatgagaat gagtcattgt caggggtgaa ccttcttaaa ggagttaagc 180
ttattgatag tggatacgtc tgtttagccg gtttggtcgt cacgggcgag tggaacttgc 240
ctgacaattg ccgtggtggt gtgagcgtgt gtctggtgga caagagaatg gaaagagcgg 300
acgaagccac actggggtca tattacactg ctgctgctaa aaagcggttt cagttcaagg 360
tcgttcccaa ttatgctata accacccagg atgcagaaaa gaacatatgg caggtcttag 420
taaatattaa aaatgtgaag atgagtgcgg gctactgccc tttgtcatta gaatttgtgt 480
cggtgtgtat tgtttataga aataatataa aattgggttt gagagagaaa gtaacgagtg 540
tgaacgatgg agggcccatg gaacttacag aagaagtcgt tgatgagttc atggaagatg 600
tccctatgtc gatcaggctt gcaaagtttc gatctcgaat cctcaaaaag agtgatgtcc 660
gcaaagggaa aaatagtagt agtgatcggt cagtgccgaa caagaactat agaaatgtta 720
aggattttgg aggaatgagt tttaaaaaga ataatttaat cgatgatgat tcggaggcta 780
ctgtcgcgga ttctgattcg tttt 804

-continued

<210> SEQ ID NO 29
<211> LENGTH: 717
<212> TYPE: DNA
<213> ORGANISM: Aequorea victoria GFP ORF

<400> SEQUENCE: 29
atgagtaaag gagaagaact tttcactgga gttgtcccaa ttcttgttga attagatggt 60
gatgttaatg ggcacaaatt ttctgtcagt ggagagggtg aaggtgatgc aacatacgga 120
aaacttaccc ttaaatttat ttgcactact ggaaaactac ctgttccatg gccaacactt 180
gtcactactt tctcttatgg tgttcaatgc ttttcaagat acccagatca tatgaaacgg 240
catgactttt tcaagagtgc catgcccgaa ggttatgtac aggaaagaac tatatttttc 300
aaggatgacg ggaactacaa gacacgtgct gaagtcaagt ttgaaggtga tacccttgtt 360
aatagaatcg agttaaaagg tattgatttt aaagaagatg gaaacattct tggacacaaa 420
ttggaataca actataactc acacaatgta tacatcatgg cagacaaaca aaagaatgga 480
atcaaagtta acttcaaaat tagacacaac attgaagatg gaagcgttca actagcagac 540
cattatcaac aaaatactcc aattggcgat ggccctgtcc ttttaccaga caaccattac 600
ctgtccacac aatctgccct ttcgaaagat cccaacgaaa agagagacca catggtcctt 660
cttgagtttg taacagctgc tgggattaca catggcatgg atgaactata caaataa 717

<210> SEQ ID NO 30
<211> LENGTH: 717
<212> TYPE: DNA
<213> ORGANISM: Aequorea victoria GFP Cycle 3 ORF

<400> SEQUENCE: 30
atgagtaaag gagaagaact tttcactgga gttgtcccaa ttcttgttga attagatggt 60
gatgttaatg ggcacaaatt ttctgtcagt ggagagggtg aaggtgatgc tacatacgga 120
aagcttaccc ttaaatttat ttgcactact ggaaaactac ctgttccatg gccaacactt 180
gtcactactt tctcttatgg tgttcaatgc ttttcccgtt atccggatca tatgaaacgg 240
catgactttt tcaagagtgc catgcccgaa ggttatgtac aggaacgcac tatatctttc 300
aaagatgacg ggaactacaa gacgcgtgct gaagtcaagt ttgaaggtga tacccttgtt 360
aatcgtatcg agttaaaagg tattgatttt aaagaagatg gaaacattct cggacacaaa 420
ctcgagtaca actataactc acacaatgta tacatcacgg cagacaaaca aaagaatgga 480
atcaaagcta acttcaaaat tcgccacaac attgaagatg gatccgttca actagcagac 540
cattatcaac aaaatactcc aattggcgat ggccctgtcc ttttaccaga caaccattac 600
ctgtcgacac aatctgccct ttcgaaagat cccaacgaaa agcgtgacca catggtcctt 660
cttgagtttg taactgctgc tgggattaca catggcatgg atgaactata caaataa 717

<210> SEQ ID NO 31
<211> LENGTH: 3637
<212> TYPE: DNA
<213> ORGANISM: Artificial Sequence
<220> FEATURE:
<223> OTHER INFORMATION: Plasmid encoding wild type Aequorea victoria
GFP Cycle 3 ORF

<400> SEQUENCE: 31
gtggcacttt tcggggaaat gtgcgcggaa cccctatttg tttatttttc taaatacatt 60
caaatatgta tccgctcatg agacaataac cctgataaat gcttcaataa tattgaaaaa 120

-continued

```
ggaagagtat gagtattcaa catttccgtg tcgcccttat tccctttttt gcggcatttt    180
gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct gggtaccgat gagtaaagga   2220
gaagaacttt tcactggagt tgtcccaatt cttgttgaat tagatggtga tgttaatggg   2280
cacaaatttt ctgtcagtgg agagggtgaa ggtgatgcaa catacggaaa acttaccctt   2340
aaatttattt gcactactgg aaaactacct gttccatggc caacacttgt cactactttc   2400
tcttatggtg ttcaatgctt ttcaagatac ccagatcata tgaaacggca tgactttttc   2460
aagagtgcca tgcccgaagg ttatgtacag gaaagaacta tatttttcaa ggatgacggg   2520
```

-continued aactacaaga cacgtgctga agtcaagttt gaaggtgata cccttgttaa tagaatcgag 2580
ttaaaaggta ttgattttaa agaagatgga aacattcttg gacacaaatt ggaatacaac 2640
tataactcac acaatgtata catcatggca gacaaacaaa agaatggaat caaagttaac 2700
ttcaaaatta gacacaacat tgaagatgga agcgttcaac tagcagacca ttatcaacaa 2760
aatactccaa ttggcgatgg ccctgtcctt ttaccagaca accattacct gtccacacaa 2820
tctgcccttt cgaaagatcc caacgaaaag agagaccaca tggtccttct tgagtttgta 2880
acagctgctg ggattacaca tggcatggat gaactataca aataagaatt cctgcagccc 2940
gggggatcca ctagttctag agcggccgcc accgcggtgg agctccaatt cgccctatag 3000
tgagtcgtat tacgcgcgct cactggccgt cgttttacaa cgtcgtgact gggaaaaccc 3060
tggcgttacc caacttaatc gccttgcagc acatccccct ttcgccagct ggcgtaatag 3120
cgaagaggcc cgcaccgatc gcccttccca acagttgcgc agcctgaatg gcgaatggga 3180
cgcgccctgt agcggcgcat taagcgcggc gggtgtggtg gttacgcgca gcgtgaccgc 3240
tacacttgcc agcgccctag cgcccgctcc tttcgctttc ttcccttcct ttctcgccac 3300
gttcgccggc tttccccgtc aagctctaaa tcgggggctc cctttagggt tccgatttag 3360
tgctttacgg cacctcgacc ccaaaaaact tgattagggt gatggttcac gtagtgggcc 3420
atcgccctga tagacggttt ttcgcccttt gacgttggag tccacgttct ttaatagtgg 3480
actcttgttc caaactggaa caacactcaa ccctatctcg gtctattctt ttgatttata 3540
agggattttg ccgatttcgg cctattggtt aaaaaatgag ctgatttaac aaaaatttaa 3600
cgcgaatttt aacaaaatat taacgcttac aatttag 3637

<210> SEQ ID NO 32
<211> LENGTH: 3637
<212> TYPE: DNA
<213> ORGANISM: Artificial Sequence
<220> FEATURE:
<223> OTHER INFORMATION: Encodes Cycle 3 BFP gene

<400> SEQUENCE: 32
gtggcacttt tcggggaaat gtgcgcggaa cccctatttg tttatttttc taaatacatt 60
caaatatgta tccgctcatg agacaataac cctgataaat gcttcaataa tattgaaaaa 120
ggaagagtat gagtattcaa catttccgtg tcgcccttat tccctttttt gcggcatttt 180
gccttcctgt ttttgctcac ccagaaacgc tggtgaaagt aaaagatgct gaagatcagt 240
tgggtgcacg agtgggttac atcgaactgg atctcaacag cggtaagatc cttgagagtt 300
ttcgccccga agaacgtttt ccaatgatga gcacttttaa agttctgcta tgtggcgcgg 360
tattatcccg tattgacgcc gggcaagagc aactcggtcg ccgcatacac tattctcaga 420
atgacttggt tgagtactca ccagtcacag aaaagcatct tacggatggc atgacagtaa 480
gagaattatg cagtgctgcc ataaccatga gtgataacac tgcggccaac ttacttctga 540
caacgatcgg aggaccgaag gagctaaccg cttttttgca caacatgggg gatcatgtaa 600
ctcgccttga tcgttgggaa ccggagctga atgaagccat accaaacgac gagcgtgaca 660
ccacgatgcc tgtagcaatg gcaacaacgt tgcgcaaact attaactggc gaactactta 720
ctctagcttc ccggcaacaa ttaatagact ggatggaggc ggataaagtt gcaggaccac 780
ttctgcgctc ggcccttccg gctggctggt ttattgctga taaatctgga gccggtgagc 840
gtgggtctcg cggtatcatt gcagcactgg ggccagatgg taagccctcc cgtatcgtag 900

-continued

```
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct gggtaccgat gagtaaagga   2220
gaagaacttt tcactggagt tgtcccaatt cttgttgaat tagatggtga tgttaatggg   2280
cacaaatttt ctgtcagtgg agagggtgaa ggtgatgcta catacggaaa gcttacactt   2340
aaatttattt gcactactgg aaaactacct gttccatggc caacacttgt cactactttc   2400
tctcatggtg ttcaatgctt ttctcgttat ccggatcata tgaaacggca tgacttttc    2460
aagagtgcca tgcccgaagg ttatgtacag gaacgcacta tatctttcaa agatgacggg   2520
aactacaaga cgcgtgctga agtcaagttt gaaggtgata cccttgttaa tcgtatcgag   2580
ttaaaaggta ttgattttaa agaagatgga aacattctcg gacacaaact cgagtacaac   2640
tttaactcac acaatgtata catcacggca gacaaacaaa agaatggaat caaagctaac   2700
ttcaaaattc gccacaacat tgaagatgga tccgttcaac tagcagacca ttatcaacaa   2760
aatactccaa ttggcgatgg ccctgtcctt ttaccagaca accattacct gtcgacacaa   2820
tctgcccttt cgaaagatcc caacgaaaag cgtgaccaca tggtccttct tgagtttgta   2880
actgctgctg ggattacaca tggcatggat gaactataca aataagaatt cctgcagccc   2940
gggggatcca ctagttctag agcggccgcc accgcggtgg agctccaatt cgccctatag   3000
tgagtcgtat tacgcgcgct cactggccgt cgttttacaa cgtcgtgact gggaaaaccc   3060
tggcgttacc caacttaatc gccttgcagc acatccccct ttcgccagct ggcgtaatag   3120
cgaagaggcc cgcaccgatc gcccttccca acagttgcgc agcctgaatg gcgaatggga   3180
cgcgccctgt agcggcgcat taagcgcggc gggtgtggtg gttacgcgca gcgtgaccgc   3240
tacacttgcc agcgccctag cgcccgctcc tttcgctttc ttcccttcct ttctcgccac   3300
```

-continued

```
gttcgccggc tttccccgtc aagctctaaa tcgggggctc cctttagggt tccgatttag   3360

tgctttacgg cacctcgacc ccaaaaaact tgattagggt gatggttcac gtagtgggcc   3420

atcgccctga tagacggttt ttcgcccttt gacgttggag tccacgttct ttaatagtgg   3480

actcttgttc caaactggaa caacactcaa ccctatctcg gtctattctt ttgatttata   3540

agggattttg ccgatttcgg cctattggtt aaaaaatgag ctgatttaac aaaaatttaa   3600

cgcgaatttt aacaaaatat taacgcttac aatttag                            3637
```

<210> SEQ ID NO 33
<211> LENGTH: 717
<212> TYPE: DNA
<213> ORGANISM: Aequorea victoria BFP Cycle 3 ORF

<400> SEQUENCE: 33

```
atgagtaaag gagaagaact tttcactgga gttgtcccaa ttcttgttga attagatggt     60

gatgttaatg ggcacaaatt ttctgtcagt ggagagggtg aaggtgatgc tacatacgga    120

aagcttacac ttaaatttat ttgcactact ggaaaactac ctgttccatg gccaacactt    180

gtcactactt tctctcatgg tgttcaatgc ttttctcgtt atccggatca tatgaaacgg    240

catgactttt tcaagagtgc catgcccgaa ggttatgtac aggaacgcac tatatctttc    300

aaagatgacg ggaactacaa gacgcgtgct gaagtcaagt ttgaaggtga tacccttgtt    360

aatcgtatcg agttaaaagg tattgatttt aaagaagatg gaaacattct cggacacaaa    420

ctcgagtaca actttaactc acacaatgta tacatcacgg cagacaaaca aaagaatgga    480

atcaaagcta acttcaaaat tcgccacaac attgaagatg gatccgttca actagcagac    540

cattatcaac aaaatactcc aattggcgat ggccctgtcc ttttaccaga caaccattac    600

ctgtcgacac aatctgccct ttcgaaagat cccaacgaaa agcgtgacca catggtcctt    660

cttgagtttg taactgctgc tgggattaca catggcatgg atgaactata caaataa       717
```

<210> SEQ ID NO 34
<211> LENGTH: 295
<212> TYPE: PRT
<213> ORGANISM: Selaginella lepidophylla

<400> SEQUENCE: 34

```
Met Ala Thr Thr Lys Thr Ser Gly Met Ala Leu Ala Leu Leu Leu Val
1               5                   10                  15

Ala Ala Leu Ala Val Gly Ala Ala Ala Trp Gly Lys Glu Gly His Arg
            20                  25                  30

Leu Thr Cys Met Val Ala Glu Pro Phe Leu Ser Ser Glu Ser Lys Gln
        35                  40                  45

Ala Val Glu Glu Leu Leu Ser Gly Arg Asp Leu Pro Asp Leu Cys Ser
    50                  55                  60

Trp Ala Asp Gln Ile Arg Arg Ser Tyr Lys Phe Arg Trp Thr Gly Pro
65                  70                  75                  80

Leu His Tyr Ile Asp Thr Pro Asp Asn Leu Cys Thr Tyr Asp Tyr Asp
                85                  90                  95

Arg Asp Cys His Asp Ser His Gly Lys Lys Asp Val Cys Val Ala Gly
            100                 105                 110

Gly Ile Asn Asn Tyr Ser Ser Gln Leu Glu Thr Phe Leu Asp Ser Glu
        115                 120                 125

Ser Ser Ser Tyr Asn Leu Thr Glu Ala Leu Leu Phe Leu Ala His Phe
    130                 135                 140
```

-continued

```
Val Gly Asp Ile His Gln Pro Leu His Val Ala Phe Thr Ser Asp Ala
145                 150                 155                 160

Gly Gly Asn Gly Val His Val Arg Trp Phe Gly Arg Lys Ala Asn Leu
                165                 170                 175

His His Val Trp Asp Thr Glu Phe Ile Ser Arg Ala Asn Arg Val Tyr
            180                 185                 190

Tyr His Asp Ile Ser Lys Met Leu Arg Asn Ile Thr Arg Ser Ile Thr
        195                 200                 205

Lys Lys Asn Phe Asn Ser Trp Ser Arg Cys Lys Thr Asp Pro Ala Ala
    210                 215                 220

Cys Ile Asp Ser Tyr Ala Thr Glu Ser Ile Asp Ala Ser Cys Asn Trp
225                 230                 235                 240

Ala Tyr Lys Asp Ala Pro Asp Gly Ser Ser Leu Asp Asp Asp Tyr Phe
                245                 250                 255

Ser Ser Arg Leu Pro Ile Val Glu Gln Arg Leu Ala Gln Gly Gly Val
            260                 265                 270

Arg Leu Ala Ser Ile Leu Asn Arg Ile Phe Gly Gly Ala Lys Ser Asn
        275                 280                 285

Arg Ser Ser Arg Ser Ser Met
    290                 295


<210> SEQ ID NO 35
<211> LENGTH: 19
<212> TYPE: PRT
<213> ORGANISM: Apium graveolens fragment of Cel I expressed by TMV

<400> SEQUENCE: 35

Asp Met Cys Val Ala Gly Ala Ile Gln Asn Phe Thr Ser Gln Leu Gly
1               5                   10                  15

His Phe Arg
```

What is claimed is:

1. An in vitro method of redistributing sequence variations between non-identical polynucleotides wherein each step is performed outside of living cells, comprising:

a) making a heteroduplex polynucleotide from two non-identical polynucleotides having 96% or more sequence identity, the heteroduplex having first and second strands;

b) mixing the heteroduplex polynucleotide with an effective amount of mismatch-directed strand cleavage activity, proofreading activity, and ligase activity wherein said mismatch-directed strand cleavage activity consists of a single enzyme that recognizes a mismatch directly; and c) allowing sufficient time for at least two non-complementary nucleotide base pairs to be converted to complementary base pairs wherein a population of polynucleotide strands not identical to either of said first and second strands results and wherein the polynucleotide strands of the population have an average of 1 or more crossovers per 120 basepairs relative to the distance between the first and last mismatches.

2. A method according to claim 1 wherein the mismatch-directed strand cleavage activity is supplied by a mismatch endonuclease, proofreading activity is supplied by a proofreading enzyme, and ligase activity is supplied by a ligase enzyme.

3. An in vitro method of making a population containing sequence variants from a heteroduplex polynucleotide wherein each step is performed outside of living cells, comprising:

a) making a heteroduplex polynucleotide from two non-identical polynucleotides having 54% or more sequence identity;

b) mixing copies of the heteroduplex polynucleotide with an effective amount of a mismatch-directed mismatch endonuclease, a proofreading enzyme, and a ligase enzyme wherein said mismatch-directed mismatch endonuclease consists of a single enzyme that recognizes a mismatch directly; and c) allowing sufficient time for a number of non-complementary nucleotide base pairs to be converted to complementary base pairs, wherein a population containing polynucleotide sequence variants results and wherein at least 20% of the population has undergone reassortment of sequence information and the sequence variants have an average of 1 or more crossovers per 250 basepairs of heteroduplex polynucleotide sequence.

4. An in vitro method of obtaining a polynucleotide encoding a desired functional property, comprising:

a) preparing at least one heteroduplex polynucleotide outside of living cells;

b) mixing copies of the heteroduplex polynucleotide with an effective amount of a mismatch-directed mismatch endonuclease, a proofreading enzyme, and a ligase enzyme outside of living cells wherein said mismatch-directed mismatch endonuclease consists of a single enzyme that recognizes a mismatch directly;

c) allowing sufficient time for a number of non-complementary nucleotide base pairs to be converted to complementary base pairs, wherein a population of at least 85% sequence variants results outside of living cells, and wherein the increased sequence diversity in said population of sequence variants is larger than the increased sequence diversity resulting from a control reaction lacking said mismatch endonuclease; and d) screening or selecting a population of sequence variants for the desired functional property.

5. A method according to claim 4 further comprising:

e) denaturing the population of sequence variants in claim 4 or a subpopulation of variants obtained by screening or selecting to obtain a population of single stranded polynucleotide variants;

f) annealing said population of single stranded polynucleotide variants to form a diverse population of heteroduplex polynucleotide sequences;

g) mixing copies of the heteroduplex polynucleotide sequences with an effective amount of a mismatch endonuclease, a proofreading enzyme, and a ligase enzyme;

h) allowing sufficient time for a number of non-complementary nucleotide base pairs to be converted to complementary base pairs, wherein a second population of polynucleotide sequence variants result; and i) screening or selecting for a polynucleotide encoding a desired functional property.

6. The method of claim 4 or 5 further comprising converting DNA to RNA prior to screening.

7. The method of claim 1 wherein said heteroduplex polynucleotide is either circular or linear.

8. The method of claim 1 wherein said heteroduplex polynucleotide is a replicon.

9. The method of claim 3 wherein said polynucleotide sequence variants have at least two but less than all of said non-complementary nucleotide base pairs converted to complementary base pairs.

10. The method of claim 1 wherein said mismatch-directed strand cleavage activity, proofreading activity, or ligase activity is mixed sequentially to or concurrently with at least one of the other two activities.

11. The method of claim 3 wherein parental molecules of the heteroduplex polynucleotide are greater than 65% identical, and wherein at least 27% of the population has undergone reassortment of sequence information and the sequence variants have an average of 1 or more crossovers per 157 basepairs of heteroduplex polynucleotide sequence.

12. The method of claim 3 wherein parental molecules of the heteroduplex polynucleotide sequence are greater than 66% identical, and wherein at least 33% of the population has undergone reassortment of sequence information and the sequence variants have an average of 1 or more crossovers per 130 basepairs of heteroduplex polynucleotide sequence.

13. The method of claim 3 wherein parental molecules of the heteroduplex polynucleotide sequence are greater than 75% identical, wherein at least 44% of the population has undergone reassortment of sequence information and the sequence variants have an average of 1 or more crossovers per 95 basepairs of heteroduplex polynucleotide sequence.

14. The method of claim 2 wherein the heteroduplex polynucleotide is about 1000 bp.

15. The method of claim 2 wherein the heteroduplex polynucleotide is about 10,000 bp.

16. The method of claim 2 wherein the heteroduplex polynucleotide is about 100,000 bp.

17. A method of identifying a reassorted DNA molecule encoding a protein with a desired functional property, comprising:

a) providing at least one single-stranded uracil-containing DNA molecule, which single-stranded uracil-containing molecule, or a complementary strand thereto, encodes a protein;

b) providing one or a plurality of non-identical single-stranded DNA molecules capable of hybridizing to the single-stranded uracil-containing molecule, wherein said DNA molecules encode at least one additional variant of the protein;

c) contacting the single-stranded uracil-containing molecule with at least one single-stranded DNA molecule of step (b), thereby producing an annealed DNA molecule;

d) incubating the annealed DNA molecule with a mismatch-directed mismatch endonuclease, proofreading enzyme and a ligase outside of living cells wherein said mismatch-directed mismatch endonuclease consists of a single enzyme that recognizes a mismatch directly, thereby producing a reassorted DNA strand annealed to the uracil-containing DNA molecule;

e) amplifying the reassorted DNA strand under conditions wherein the uracil-containing DNA molecule is not amplified, thereby producing a population of reassorted DNA molecules wherein at least 44% of the population has undergone reassortment of sequence information; and, f) screening or selecting the population of reassorted DNA molecules to identify those that encode a polypeptide having the desired functional property, thereby identifying one or more DNA molecules(s) that encode a polypeptide with the desired functional property.

* * * * *